US006808894B1

(12) United States Patent
Nicolaides et al.

(10) Patent No.: US 6,808,894 B1
(45) Date of Patent: Oct. 26, 2004

(54) METHODS FOR GENERATING GENETICALLY ALTERED ANTIBODY PRODUCING CELL LINES WITH IMPROVED ANTIBODY CHARACTERISTICS

(75) Inventors: Nicholas C. Nicolaides, Boothwyn, PA (US); Luigi Grasso, Philadelphia, PA (US); Philip M. Sass, Audubon, PA (US)

(73) Assignee: Morphotek, Inc., Exton, PA (US)

( * ) Notice: Subject to any disclaimer, the term of this patent is extended or adjusted under 35 U.S.C. 154(b) by 251 days.

(21) Appl. No.: 09/707,468

(22) Filed: Nov. 7, 2000

(51) Int. Cl.[7] .......... C12N 15/00

(52) U.S. Cl. .......... 435/69.1; 435/325; 435/320.1; 536/23.5; 536/24.5; 424/130.1

(58) Field of Search .......... 435/69.1, 320.1, 435/325; 424/130.1; 536/23.5, 24.5, 23.1, 23.2

(56) References Cited

U.S. PATENT DOCUMENTS

| | | | | |
|---|---|---|---|---|
| 5,530,101 A | 6/1996 | Queen et al. | 530/387.3 |
| 5,907,079 A | 5/1999 | Mak et al. | 800/2 |
| 6,146,894 A | 11/2000 | Nicolaides et al. | 435/440 |
| 6,191,268 B1 | 2/2001 | Liskay et al. | 536/23.5 |
| 6,287,862 B1 | 9/2001 | delCardayre et al. | |

FOREIGN PATENT DOCUMENTS

| | | |
|---|---|---|
| CA | 2240609 | 10/1999 |
| WO | WO 97/05268 | 2/1997 |
| WO | 99/19492 | 4/1999 |

OTHER PUBLICATIONS

Verma et al. Gene therapy promises, problems and prospects pp. 239–242 vol. 389 1997.*

Russell et al. Structural features can be unconserved in proteins with similar folds pp. 332–350 1994.*

Ngo et al. Computational complexity, protein structure prediction, and the levinthal paradox pp. 491–495 1994.*

Aronshtam, A., et al. "Dominant negative mutator mutations in the mutl gene of *Escherichia coli", Nucleic Acids Research*, 1996, 24(13), pp 2498–2504.

Cascalho M, et al. "Mismatch repair co–opted by hypermutation", *Science*, 1998, 279(20), pp 1207–1210.

Polaczek, P., et al. "Functional genetic tests of DNA mismatch repair protein activity in Saccharomyces cerevisiae", *Gene*, 1998, 213(1–2), pp 159–167.

Culligan, K.M., et al., "DNA mismatch repair in plants," *Plant Physiol.*, 1997, 15, XP–002099372, 833–839.

Jean, M., et al., "Isolation and characterization of *AtMLH1, a MutL* homologue from *Arabidopsis thaliana," Mol. Gen. Genet.*, 1999, 262, XP–000986138, 633–642.

Lipkin, S.M., et al., "MLH3: a DNA mismatch repair gene associated with mammalian microsatellite instability," *Nature Genetics*, 2000, 24, XP–002165243, 27–35.

Chakravarti, D. et al., "Relating aromatic hydrocarbon–induced DNA adducts and c–H–ras mutations in mouse skin papillomas: The role of apurinic sites", *Proc. Natl. Acad. Sci. USA*, Oct. 1995, vol. 92, pp. 10422–10426.

(List continued on next page.)

*Primary Examiner*—Dave T. Nguyen
(74) *Attorney, Agent, or Firm*—Woodcock Washburn LLP

(57) ABSTRACT

Dominant negative alleles of human mismatch repair genes can be used to generate hypermutable cells and organisms. By introducing these genes into cells and transgenic animals, new cell lines and animal varieties with novel and useful properties can be prepared more efficiently than by relying on the natural rate of mutation. These methods are useful for generating genetic diversity within immunoglobulin genes directed against an antigen of interest to produce altered antibodies with enhanced biochemical activity. Moreover, these methods are useful for generating antibody-producing cells with increased level of antibody production.

21 Claims, 7 Drawing Sheets

HBvec HB134
\- + - + RT
-PMS134
\- housekeeping gene

OTHER PUBLICATIONS

Quian, Y. et al., "Molecular events after antisense inhibition of hMSH2 in a HeLa cell line", *Mutation Research*, Oct. 12, 1998, vol. 418, pp. 61–71.

Yu, Y. et al., "Adriamycin inducсs large deletions as a major type of mutation in CHO cells", *Mutation Research*, Nov. 1994, vol. 325, pp. 91–98.

Liu et al., "Analysis of Mismatch Repair Genes in Hereditary Non–polyposis Colorectal Cancer Patients", *Nature Medicine*, Feb. 1996, 2(2), 169–174.

Ma et al., "Dominant Negative Expression of hPMS2 Creates Isogenic Mismatch Repair Deficient Human Colon Cancer Cell Lines", *Proc. Am. Assoc. Cancer Res.*, Mar. 1998, 39, p. 460 (Abstract #3130).

Weiner, L.M., "Monoclonal Antibody Therapy of Cancer", *Semin. Oncol.*, Oct. 1999, vol. 26, No. 5, Suppl. 14, pp. 43–51.

Fiedler, U. et al., "High–Level Production and Long–Term Storage of Engineered Antibodies in Transgenic Tobacco Seeds", *Bio/Technology*, 1995, 13, 1090–1093.

Frigerio, L. et al., "Assembly, Secretion, and Vacuolar Delivery of a Hybrid Immunoglobin in Plants", *Plant Physiol*, 2000, 123, 1483–1494.

Galio, L., et al., "ATP hydrolysis–dependent formation of a dynamic ternary nucleoprotein complex with MutS and MutL," *Nucleic Acids Research*, 1999, 27(11), 2325–2331.

Glaser, V., "Gene Therapy's Other Investment Window", *Nat. Biotechnol.*, 1996, 14, 1216–1217.

Harfe, B.D., "DNA mismatch repair and genetic instability," *Annu. Rev. Genet.*, 2000, 34, 359–399.

Hoang J., et al., "BAT–26, an Indicator of the Replication Error Phenotype in Colorectal Cancers and Cell Lnes", *Cancer Res.*, 1997, 57, 300–303.

Honma, M. et al., "Cytotoxic and Mutagenic Responses to X–rays and Chemical Mutagens in Normal and p53–mutated Human Lymphoblastoid Cells", *Mut. Res.*, 1997, 374, 89–98.

Jiricny, J., et al., "Mismatch repair defects in cancer," *Curr. Opin. Genet. Dev.*, 2000, 10, 157–161.

Karran, P., et al., "Genomic instability and tolerance to alkylating agents," *Cancer Surveys*, 1996, 28, 69–71.

Khazaeli, M.B. et al., "Huamn Immune Response to Monoclonal Antibodies", *J. Immunother.*, 1994, 15, 42–52.

Kong, Q., et al., "PMS2–deficiency diminishes hypermutation of a lamdal transgene in young but not older mice", *Mol. Immunol.*, 1999, 36, 83–91.

Leach, F.S., et al., "Mutations of a mutS homolog in hereditary nonpolyposis colorectal cancer," *Cell*, 1993, 75, 1215–1225.

Liu, T., et al., "Microsatellite instability as a predictor of a mutation in a DNA mismatch repair gene in familial colorectal cancer," *Genes, Chromosomes & Cancer*, 2000, 27, 17–25.

McCallum, C.M., "Targeted screening for induced mutations," *Nature Biotechnology*, 2000, 18, 455–457.

Modrich, P., "Mismatch repair, genetic stability, and cancer," *Science*, 1994, 266, 1959–1960.

Neuberger, M., et al., "Mice perform a human repertoire," *Nature*, 1997, 386, 25–26.

Nicolaides, N.C., et al., "The jun family members, c–jun and junD, transactivate the human c–myb, promoter via an Ap1–like element," *J. Biological Chemistry*, 1992, 267(27), 19655–19672.

Nicolaides, N.C., et al., "Genomic organization of the human PMS2 gene family," *Genomics*, 1995, 30, 195–206.

Nicolaides, N.C., et al., "Positive autoregulation of c–myb, expression via Myb binding sites in the 5' flanking region of the human c–myb gene," *Molecular and Cellular Biology*, 1991, 11(12), 6166–6176.

Nicolaides, N.C., "A naturally occurring hPMS2 mutation can confer a dominant negative nutator phenotype," *Mol. Cell. Biol.*, 1998, 18(3), 1635–1641.

Nicolaides, N.C., et al., "Analysis of the 5' region of PMS2 reveals heterogeneous transcripts and a novel overlapping gene," *Genomics*, 1995, 29, 329–334.

Nicolaides, N.C., et al., "Mutations of two PMS homologues in hereditary nonpolyposis colon cancer," *Nature*, 1994, 371, 75–80.

Palombo, F., et al., "Mismatch repair and cancer," *Nature*, 1994, 367, 417.

Papadopoulos, N., et al., "Mutation of a mutL homolog in hereditary colon cancer," *Science*, 1994, 263, 1625–1629.

Papadopoulos, N., et al., "Mutations of GTBP in genetically unstable cells," *Science*, 1995, 268, 1915–1917.

Parsons, R., et al., "hypermutability and mismatch repair deficiency in RER+ tumor cells," *Cell*, 1993, 75, 1227–1236.

Peinado, M.A., et al., "Isolation and characterization of allelic lossesand gains in colorectal tumors by arbitrarily primed polymerase chain reaction," *Proc. Natl. Acad. Sci. USA*, 1992, 89, 10065–10069.

Perucho, M., et al., "Cancer of the microsatellite mutator phenotype," *Biol. Chem.*, 1996, 377, 675–684.

Prolla, T.A., et al., "MLH1, PMS1, and MSH2 interactions during the initiation of DNA mismatch repair in yeast," *Science*, 1994, 265, 1091–1093.

Reff, M.E., "High–level production of recombinant immunoglobulins in mammalian cells", *Curr. Opin. Biotechnol.*, 1993, 4, 573–576.

Saez–Llorens, X.E. et al., "Safety and pharmacokinetics of an intramuscular humanized monoclonal antibody to respiratory syncytial virus in premature infants and infants with bronchopulmonary dysplasia", *Pediat. Infect. Dis. J.*, 1998, 17(9), 787–791.

Schrader, C.E. et al., "Reduced Isotype Switching in Splenic B Cells from Mice Deficient in Mismatch Repair Enzymes", *Journal of Experimental Medicine*, 1999, 190(3), 323–330.

Shield, C.F. et al., "A Cost–Effectiveness Analysis of OKT3 Induction Therapy in Cadaveric Kidney Transplantation", *Am. J. Kidney Dis.*, 1996, 27, 855–864.

Shields, R.L. et al., "Anti–IgE Monoclonal Antibodies that Inhibit Allergen–Specific Histamine Release", *Int. Arch. Allergy Immunol.*, 1995, 107, 412–413.

Spampinato, C., et al., "The MutL ATPase is required for mismatch repair," *J. Biological Chemistry*, 2000, 275(13 ), 9863–9869.

Strand, M., et al., "Destabilization of tracts of simple repetitive DNA in yeast by mutations affecting DNA mismatch repair," *Nature*, 1993, 365, 274–276.

Su, S., et al., "Mispair specificity of methyl–directed DNA mismatch correction In Vitro," *J. Biologicl Chemistyr*, 1988, 263(14), 6829–6835.

Vora, K.A. et al., "Severe Attenuation of the B Cell Immune Response in Msh2–deficient Mice", *Journal of Experimental Medicien*, Feb. 1999, 189(3), 471–481.

Wheeler, J.M.D., et al., "The role of hypermethylation of the hMLH1 promoter region in HNPCC verus MSI+sporadic colorectal cancers," *J. Med. Gent.*, 2000, 588–592.

Winter, D.B. et al., "Altered spectra of hypermutation in antibodies from mice deficient for the DNA mismatch repair protein PMS2", *Proc. Natl. Acad. Sci., USA*, Jun. 1998, 95, 6953–6958.

* cited by examiner

* = clones with a significant difference in antigen binding

METHODS FOR GENERATING GENETICALLY ALTERED ANTIBODY PRODUCING CELL LINES WITH IMPROVED ANTIBODY CHARACTERISTICS

TECHNICAL FIELD OF THE INVENTION

The invention is related to the area of antibody maturation and cellular production. In particular, it is related to the field of mutagenesis.

BACKGROUND OF THE INVENTION

The use of antibodies to block the activity of foreign and/or endogenous polypeptides provides an effective and selective strategy for treating the underlying cause of disease. In particular is the use of monoclonal antibodies (MAb) as effective therapeutics such as the FDA approved ReoPro (Glaser, V. (1996) Can ReoPro repolish tarnished monoclonal therapeutics? *Nat. Biotechnol.* 14: 1216–1217), an anti-platelet MAb from Centocor; Herceptin (Weiner, L. M. (1999) Monoclonal antibody therapy of cancer. *Semin. Oncol.* 26:43–51), an anti-Her2/neu MAb from Genentech; and Synagis (Saez-Llorens, X. E., et al. (1998) Safety and pharmacokinetics of an intramuscular humanized monoclonal antibody to respiratory syncytial virus in premature infants and infants with bronchopulmonary dysplasia. *Pediat. Infect. Dis. J.* 17:787–791), an anti-respiratory syncytial virus MAb produced by Medimmune.

Standard methods for generating MAbs against candidate protein targets are known by those skilled in the art. Briefly, rodents such as mice or rats are injected with a purified antigen in the presence of adjuvant to generate an immune response (Shield, C. F., et al (1996) A cost-effective analysis of OKT3 induction therapy in cadaveric kidney transplantation. *Am. J. Kidney Dis.* 27:855–864). Rodents with positive immune sera are sacrificed and splenocytes are isolated. Isolated splenocytes are fused to melanomas to produce immortalized cell lines that are then screened for antibody production. Positive lines are isolated and characterized for antibody production. The direct use of rodent MAbs as human therapeutic agents were confounded by the fact that human anti-rodent antibody (HARA) responses occurred in a significant number of patients treated with the rodent-derived antibody (Khazaeli, M. B., et al., (1994) Human immune response to monoclonal antibodies. *J. Immunother.* 15:42–52). In order to circumvent the problem of HARA, the grafting of the complementarity determining regions (CDRs), which are the critical motifs found within the heavy and light chain variable regions of the immunoglobulin (Ig) subunits making up the antigen binding domain, onto a human antibody backbone found these chimeric molecules are able to retain their binding activity to antigen while lacking the HARA response (Emery, S. C., and Harris, W. J. “Strategies for humanizing antibodies” In: ANTIBODY ENGINEERING C. A. K. Borrebaeck (Ed.) Oxford University Press, N.Y. 1995. pp. 159–183. A common problem that exists during the “humanization” of rodent-derived MAbs (referred to hereon as HAb) is the loss of binding affinity due to conformational changes in the 3 dimensional structure of the CDR domain upon grafting onto the human Ig backbone (U.S. Pat. No. 5,530,101 to Queen et al.). To overcome this problem, additional HAb vectors are usually needed to be engineered by inserting or deleting additional amino acid residues within the framework region and/or within the CDR coding region itself in order to recreate high affinity HAbs (U.S. Pat. No. 5,530,101 to Queen et al.). This process is a very time consuming procedure that involves the use of expensive computer modeling programs to predict changes that may lead to a high affinity HAb. In some instances the affinity of the HAb is never restored to that of the MAb, rendering them of little therapeutic use.

Another problem that exists in antibody engineering is the generation of stable, high yielding producer cell lines that is required for manufacturing of the molecule for clinical materials. Several strategies have been adopted in standard practice by those skilled in the art to circumvent this problem. One method is the use of Chinese Hamster Ovary (CHO) cells transfected with exogenous Ig fusion genes containing the grafted human light and heavy chains to produce whole antibodies or single chain antibodies, which are a chimeric molecule containing both light and heavy chains that form an antigen-binding polypeptide (Reff, M. E. (1993) High-level production of recombinant immunoglobulins in mammalian cells. *Curr. Opin. Biotechnol.* 4:573–576). Another method employs the use of human lymphocytes derived from transgenic mice containing a human grafted immune system or transgenic mice containing a human Ig gene repertoire. Yet another method employs the use of monkeys to produce primate MAbs, which have been reported to lack a human anti-monkey response (Neuberger, M., and Gruggermann, M. (1997) Monoclonal antibodies. Mice perform a human repertoire. *Nature* 386:25–26). In all cases, the generation of a cell line that is capable of generating sufficient amounts of high affinity antibody poses a major limitation for producing sufficient materials for clinical studies. Because of these limitations, the utility of other recombinant systems such as plants are currently being explored as systems that will lead to the stable, high-level production of humanized antibodies (Fiedler, U., and Conrad, U. (1995) High-level production and long-term storage of engineered antibodies in transgenic tobacco seeds. *Bio/Technology,* 13:1090–1093).

A method for generating diverse antibody sequences within the variable domain that results in HAbs and MAbs with high binding affinities to antigens would be useful for the creation of more potent therapeutic and diagnostic reagents respectively. Moreover, the generation of randomly altered nucleotide and polypeptide residues throughout an entire antibody molecule will result in new reagents that are less antigenic and/or have beneficial pharmacokinetic properties. The invention described herein is directed to the use of random genetic mutation throughout an antibody structure in vivo by blocking the endogenous mismatch repair (MMR) activity of a host cell producing immunoglobulins that encode biochemically active antibodies. The invention also relates to methods for repeated in vivo genetic alterations and selection for antibodies with enhanced binding and pharmacokinetic profiles.

In addition, the ability to develop genetically altered host cells that are capable of secreting increased amounts of antibody will also provide a valuable method for creating cell hosts for product development. The invention described herein is directed to the creation of genetically altered cell hosts with increased antibody production via the blockade of MMR.

The invention facilitates the generation of high affinity antibodies and the production of cell lines with elevated levels of antibody production. Other advantages of the present invention are described in the examples and figures described herein.

SUMMARY OF THE INVENTION

The invention provides methods for generating genetically altered antibodies (including single chain molecules)

and antibody producing cell hosts in vitro and in vivo, whereby the antibody possess a desired biochemical property(s), such as, but not limited to, increased antigen binding, increased gene expression, and/or enhanced extracellular secretion by the cell host. One method for identifying antibodies with increased binding activity or cells with increased antibody production is through the screening of MMR defective antibody producing cell clones that produce molecules with enhanced binding properties or clones that have been genetically altered to produce enhanced amounts of antibody product.

The antibody producing cells suitable for use in the invention include, hut are not limited to rodent, primate, or human hybridomas or lymphoblastoids; mammalian cells transfected and expressing exogenous Ig subunits or chimeric single chain molecules; plant cells, yeast or bacteria transfected and expressing exogenous Ig subunits or chimeric single chain molecules.

Thus, the invention provides methods for making hypermutable antibody-producing cells by introducing a polynucleotide comprising a dominant negative allele of a mismatch repair gene into cells that are capable of producing antibodies. The cells that are capable of producing antibodies include cells that naturally produce antibodies, and cells that are engineered to produce antibodies through the introduction of immunoglobulin encoding sequences. Conveniently, the introduction of polynucleotide sequences into cells is accomplished by transfection.

The invention also provides methods of making hypermutable antibody producing cells by introducing a dominant negative mismatch repair (MMR) gene such as PMS2 (preferably human PMS2), MLH1, PMS1, MSH2, or MSH2 into cells that are capable of producing antibodies. The dominant negative allele of a mismatch repair gene may be a truncation mutation of a mismatch repair gene (preferably a truncation mutation at codon 134, or a thymidine at nucleotide 424 of wild-type PMS2). The invention also provides methods in which mismatch repair gene activity is suppressed. This may be accomplished, for example, using antisense molecules directed against the mismatch repair gene or transcripts.

Other embodiments of the invention provide methods for making a hypermutable antibody producing cells by introducing a polynucleotide comprising a dominant negative allele of a mismatch repair gene into fertilized eggs of animals. These methods may also include subsequently implanting the eggs into pseudo-pregnant females whereby the fertilized eggs develop into a mature transgenic animal. The mismatch repair genes may include, for example, PMS2 (preferably human PMS2), MLH1, PMS1, MSH2, or MSH2. The dominant negative allele of a mismatch repair gene may be a truncation mutation of a mismatch repair gene (preferably a truncation mutation at codon 134, or a thymidine at nucleotide 424 of wild-type PMS2).

The invention further provides homogeneous compositions of cultured, hypermutable, mammalian cells that are capable of producing antibodies and contain a dominant negative allele of a mismatch repair gene. The mismatch repair genes may include, for example, PMS2 (preferably human PMS2), MLH1, PMS1, MSH2, or MSH2. The dominant negative allele of a mismatch repair gene may be a truncation mutation of a mismatch repair gene (preferably a truncation mutation at codon 134, or a thymidine at nucleotide 424 of wild-type PMS2). The cells of the culture may contain PMS2, (preferably human PMS2), MLH1, or PMS1; or express a human mutL homolog, or the first 133 amino acids of hPMS2.

The invention further provides methods for generating a mutation in an immunoglobulin gene of interest by culturing an immunoglobulin producing cell selected for an immunoglobulin of interest wherein the cell contains a dominant negative allele of a mismatch repair gene. The properties of the immunoglobulin produced from the cells can be assayed to ascertain whether the immunoglobulin gene harbors a mutation. The assay may be directed to analyzing a polynucleotide encoding the immunoglobulin, or may be directed to the immunoglobulin polypeptide itself.

The invention also provides methods for generating a mutation in a gene affecting antibody production in an antibody-producing cell by culturing the cell expressing a dominant negative allele of a mismatch repair gene, and testing the cell to determine whether the cell harbors mutations within the gene of interest, such that a new biochemical feature (e.g., over-expression and/or secretion of immunoglobulin products) is generated. The testing may include analysis of the steady state expression of the immunoglobulin gene of interest, and/or analysis of the amount of secreted protein encoded by the immunoglobulin gene of interest. The invention also embraces prokaryotic and eukaryotic transgenic cells made by this process, including cells from rodents, non-human primates and humans.

Other aspects of the invention encompass methods of reversibly altering the hypermutability of an antibody producing cell, in which an inducible vector containing a dominant negative allele of a mismatch repair gene operably linked to an inducible promoter is introduced into an antibody-producing cell. The cell is treated with an inducing agent to express the dominant negative mismatch repair gene (which can be PMS2 (preferably human PMS2), MLH1, or PMS1). Alternatively, the cell may be induced to express a human mutL homolog or the first 133 amino acids of hPMS2. In another embodiment, the cells may be rendered capable of producing antibodies by co-transfecting a preselected immunoglobulin gene of interest. The immunoglobulin genes of the hypermutable cells, or the proteins produced by these methods may be analyzed for desired properties, and induction may be stopped such that the genetic stability of the host cell is restored.

The invention also embraces methods of producing genetically altered antibodies by transfecting a polynucleotide encoding an immunoglobulin protein into a cell containing a dominant negative mismatch repair gene (either naturally or in which the dominant negative mismatch repair gene was introduced into the cell), culturing the cell to allow the immunoglobulin gene to become mutated and produce a mutant immunoglobulin, screening for a desirable property of said mutant immunoglobulin protein, isolating the polynucleotide molecule encoding the selected mutant immunoglobulin possessing the desired property, and transfecting said mutant polynucleotide into a genetically stable cell, such that the mutant antibody is consistently produced without further genetic alteration. The dominant negative mismatch repair gene may be PMS2 (preferably human PMS2), MLH1, or PMS1. Alternatively, the cell may express a human mutL homolog or the first 133 amino acids of hPMS2.

The invention further provides methods for generating genetically altered cell lines that express enhanced amounts of an antigen binding polypeptide. These antigen-binding polyeptides may be, for example, immunoglobulins. The methods of the invention also include methods for generating genetically altered cell lines that secrete enhanced amounts of an antigen binding polypeptide. The cell lines are rendered hypermutable by dominant negative mismatch repair genes that provide an enhanced rate of genetic hypermutation in a cell producing antigen-binding polypeptides such as antibodies. Such cells include, but are not limited to hybridomas. Expression of enhanced amounts of antigen binding polypeptides may be through enhanced transcription or translation of the polynucleotides encoding the antigen binding polypeptides, or through the enhanced secretion of the antigen binding polypeptides, for example.

Methods are also provided for creating genetically altered antibodies in vivo by blocking the MMR activity of the cell host, or by transfecting genes encoding for immunoglobulin in a MMR defective cell host.

Antibodies with increased binding properties to an antigen due to genetic changes within the variable domain are provided in methods of the invention that block endogenous MMR of the cell host. Antibodies with increased binding properties to an antigen due to genetic changes within the CDR regions within the light and/or heavy chains are also provided in methods of the invention that block endogenous MMR of the cell host.

The invention provides methods of creating genetically altered antibodies in MMR defective Ab producer cell lines with enhanced pharmacokinetic properties in host organisms including but not limited to rodents, primates, and man.

These and other aspects of the invention are provided by one or more of the embodiments described below. In one embodiment of the invention, a method for making an antibody producing cell line hypermutable is provided. A polynucleotide encoding a dominant negative allele of a MMR gene is introduced into an antibody-producing cell. The cell becomes hypermutable as a result of the introduction of the gene.

In another embodiment of the invention, a method is provided for introducing a mutation into an endogenous gene encoding for an immunoglobulin polypeptide or a single chain antibody. A polynucleotide encoding a dominant negative allele of a MMR gene is introduced into a cell. The cell becomes hypermutable as a result of the introduction and expression of the MMR gene allele. The cell further comprises an immunoglobulin gene of interest. The cell is grown and tested to determine whether the gene encoding for an immunoglobulin or a single chain antibody of interest harbors a mutation. In another aspect of the invention, the gene encoding the mutated immunoglobulin polypeptide or single chain antibody may be isolated and expressed in a genetically stable cell. In a preferred embodiment, the mutated antibody is screened for at least one desirable property such as, but not limited to, enhanced binding characteristics.

In another embodiment of the invention, a gene or set of genes encoding for Ig light and heavy chains or a combination therein are introduced into a mammalian cell host that is MMR defective. The cell is grown, and clones are analyzed for antibodies with enhanced binding characteristics.

In another embodiment of the invention, a method will he provided for producing new phenotypes of a cell. A polynucleotide encoding a dominant negative allele of a MMR gene is introduced into a cell. The cell becomes hypermutable as a result of the introduction of the gene. The cell is grown. The cell is tested for the expression of new phenotypes where the phenotype is enhanced secretion of a polypeptide.

These and other embodiments of the invention provide the art with methods that can generate enhanced mutability in cells and animals as well as providing cells and animals harboring potentially useful mutations for the large-scale production of high affinity antibodies with beneficial pharmacokinetic profiles.

Figure 1:
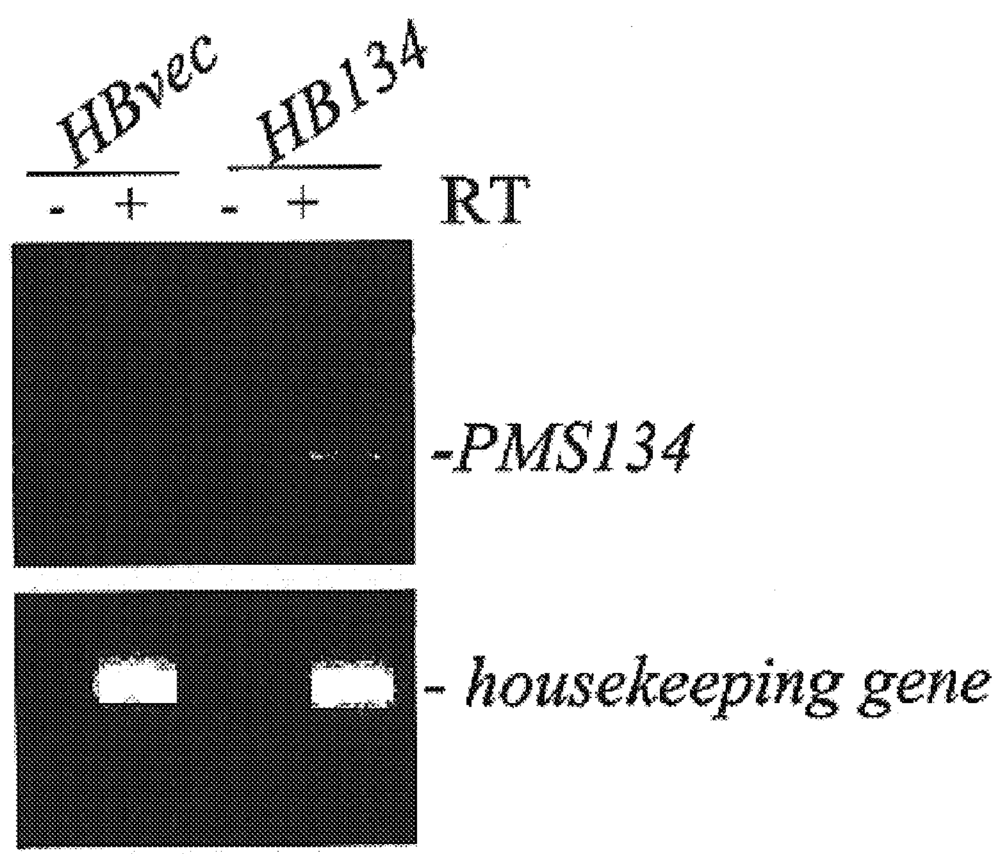
FIG. 1. Hybridoma cells stably expressing PMS2 and PMS134 MMR genes. Shown is steady state mRNA expression of MMR genes transfected into a murine hybridoma cell line. Stable expression was found after 3 months of continuous growth. The (−) lanes represent negative controls where no reverse transcriptase was added, and the (+) lanes represent samples reverse transcribed and PCR amplified for the MMR genes and an internal housekeeping gene as a control.

Lane 2: H36 cell; Lane 3: HB134 clone with elevated MAb levels; Lane 4: HB 134 clone with elevated MAb levels; Lane 5: HB134 clone with elevated MAb levels.

Methods have been discovered for developing hypermutable antibody-producing cells by taking advantage of the conserved mismatch repair (MMR) process of host cells. Dominant negative alleles of such genes, when introduced into cells or transgenic animals, increase the rate of spontaneous mutations by reducing the effectiveness of DNA repair and thereby render the cells or animals hypermutable. Hypermutable cells or animals can then be utilized to develop new mutations in a gene of interest. Blocking MMR in antibody-producing cells such as but not limited to: hybridomas; mammalian cells transfected with genes encoding for Ig light and heavy chains; mammalian cells transfected with genes encoding for single chain antibodies; eukaryotic cells transfected with Ig genes, can enhance the rate of mutation within these cells leading to clones that have enhanced antibody production and/or cells containing genetically altered antibodies with enhanced biochemical properties such as increased antigen binding. The process of MMR, also called mismatch proofreading, is carried out by protein complexes in cells ranging from bacteria to mammalian cells. A MMR gene is a gene that encodes for one of the proteins of such a mismatch repair complex. Although not wanting to be bound by any particular theory of mechanism of action, a MMR complex is believed to detect distortions of the DNA helix resulting from non-complementary pairing of nucleotide bases. The non-complementary base on the newer DNA strand is excised, and the excised base is replaced with the appropriate base, which is complementary to the older DNA strand. In this way, cells eliminate many mutations that occur as a result of mistakes in DNA replication.

Dominant negative alleles cause a MMR defective phenotype even in the presence of a wild-type allele in the same cell. An example of a dominant negative allele of a MMR gene is the human gene hPMS2-134, which carries a truncating mutation at codon 134 (SEQ ID NO:15). The mutation causes the product of this gene to abnormally terminate at the position of the 134th amino acid, resulting in a shortened polypeptide containing the N-terminal 133 amino acids. Such a mutation causes an increase in the rate of mutations, which accumulate in cells after DNA replication. Expression of a dominant negative allele of a mismatch repair gene results in impairment of mismatch repair activity, even in the presence of the wild-type allele. Any allele which produces such effect can be used in this invention. Dominant negative alleles of a MMR gene can be obtained from the cells of humans, animals, yeast, bacteria, or other organisms. Such alleles can be identified by screening cells for defective MMR activity. Cells from animals or humans with cancer can be screened for defective mismatch repair. Cells from colon cancer patients may be particularly useful. Genomic DNA, cDNA, or mRNA from any cell encoding a MMR protein can be analyzed for variations from the wild type sequence. Dominant negative alleles of a MMR gene can also be created artificially, for example, by producing variants of the hPMS2-134 allele or other MMR genes. Various techniques of site-directed mutagenesis can be used. The suitability of such alleles, whether natural or artificial, for use in generating hypermutable cells or animals can be evaluated by testing the mismatch repair activity caused by the allele in the presence of one or more wild-type alleles, to determine if it is a dominant negative allele.

A cell or an animal into which a dominant negative allele of a mismatch repair gene has been introduced will become hypermutable. This means that the spontaneous mutation rate of such cells or animals is elevated compared to cells or animals without such alleles. The degree of elevation of the spontaneous mutation rate can he at least 2-fold, 5-fold, 10-fold, 20-fold, 50-fold, 100-fold, 200-fold, 500-fold, or 1000-fold that of the normal cell or animal. The use of chemical mutagens such as but limited to methane sulfonate, dimethyl sulfonate, O6-methyl benzadine. MNU, ENU, etc. can be used in MMR defective cells to increase the rates an additional 10 to 100 fold that of the MMR deficiency itself According to one aspect of the invention, a polynucleotide encoding for a dominant negative form of a MMR protein is introduced into a cell. The gene can be any dominant negative allele encoding a protein, which is part of a MMR complex, for example, PMS2, PMS1, MLH1, or MSH2. The dominant negative allele can be naturally occurring or made in the laboratory. The polynucleotide can be in the form of genomic DNA, cDNA, RNA, or a chemically synthesized polynucleotide.

The polynucleotide can be cloned into an expression vector containing a constitutively active promoter segment (such as but not limited to CMV, SV40, Elongation Factor or LTR sequences) or to inducible promoter sequences such as the steroid inducible pIND vector (Invitrogen), where the expression of the dominant negative MMR gene can be regulated. The polynucleotide can be introduced into the cell by transfection.

According to another aspect of the invention, an immunoglobulin (Ig) gene, a set of Ig genes or a chimeric gene containing whole or parts of an Ig gene can be transfected into MMR deficient cell hosts, the cell is grown and screened for clones containing genetically altered Ig genes with new biochemical features. MMR defective cells may be of human, primates, mammals, rodent, plant, yeast or of the prokaryotic kingdom. The mutated gene encoding the Ig with new biochemical features may be isolated from the respective clones and introduced into genetically stable cells (i.e., cells with normal MMR) to provide clones that consistently produce Ig with the new biochemical features. The method of isolating the Ig gene encoding Ig with new biochemical features may be any method known in the art. Introduction of the isolated polynucleotide encoding the Ig with new biochemical features may also be performed using any method known in the art, including, but not limited to transfection of an expression vector containing the polynucleotide encoding the Ig with new biochemical features. As an alternative to transfecting an Ig gene, a set of Ig genes or a chimeric gene containing whole or parts of an Ig gene into an MMR deficient host cell, such Ig genes may be transfected simultaneously with a gene encoding a dominant negative mismatch repair gene into a genetically stable cell to render the cell hypermutable.

Transfection is any process whereby a polynucleotide is introduced into a cell. The process of transfection can be carried out in a living animal, e.g., using a vector for gene therapy, or it can be carried out in vitro, e.g., using a suspension of one or more isolated cells in culture. The cell can be any type of eukaryotic cell, including, for example, cells isolated from humans or other primates, mammals or other vertebrates, invertebrates, and single celled organisms such as protozoa, yeast, or bacteria.

In general, transfection will be carried out using a suspension of cells, or a single cell, but other methods can also be applied as long as a sufficient fraction of the treated cells or tissue incorporates the polynucleotide so as to allow transfected cells to be grown and utilized. The protein product of the polynucleotide may be transiently or stably expressed in the cell. Techniques for transfection are well known. Available techniques for introducing polynucleotides include but are not limited to electroporation, transduction, cell fusion, the use of calcium chloride, and packaging of the polynucleotide together with lipid for fusion with the cells of interest. Once a cell has been transfected with the MMR gene, the cell can be grown and reproduced in culture. If the transfection is stable, such that the gene is expressed at a consistent level for many cell generations, then a cell line results.

An isolated cell is a cell obtained from a tissue of humans or animals by mechanically separating out individual cells and transferring them to a suitable cell culture medium, either with or without pretreatment of the tissue with enzymes. e.g., collagenase or trypsin. Such isolated cells are typically cultured in the absence of other types of cells. Cells selected for the introduction of a dominant negative allele of a mismatch repair gene may be derived from a eukaryotic organism in the form of a primary cell culture or an immortalized cell line, or may be derived from suspensions of single-celled organisms.

A polynucleotide encoding for a dominant negative form of a MMR protein can be introduced into the genome of an animal by producing a transgenic animal. The animal can be any species for which suitable techniques are available to produce transgenic animals. For example, transgenic animals can be prepared from domestic livestock, e.g., bovine, swine, sheep, goats, horses, etc.; from animals used for the production of recombinant proteins, e.g., bovine, swine, or goats that express a recombinant polypeptide in their milk; or experimental animals for research or product testing, e.g., mice, rats, guinea pigs, hamsters, rabbits, etc. Cell lines that are determined to be MMR defective can then be used as a source for producing genetically altered immunoglobulin genes in vitro by introducing whole, intact immunoglobulin genes and/or chimeric genes encoding for single chain antibodies into MMR defective cells from any tissue of the MMR defective animal.

Once a transfected cell line or a colony of transgenic animals has been produced, it can be used to generate new mutations in one or more gene(s) of interest. A gene of interest can be any gene naturally possessed by the cell line or transgenic animal or introduced into the cell line or transgenic animal. An advantage of using such cells or animals to induce mutations is that the cell or animal need not be exposed to mutagenic chemicals or radiation, which may have secondary harmful effects, both on the object of the exposure and on the workers. However, chemical mutagens may be used in combination with MMR deficiency, which renders such mutagens less toxic due to an undetermined mechanism. Hypermutable animals can then be bred and selected for those producing genetically variable B-cells that may be isolated and cloned to identify new cell lines that are useful for producing genetically variable cells. Once a new trait is identified, the dominant negative MMR gene allele can be removed by directly knocking out the allele by technologies used by those skilled in the art or by breeding to mates lacking the dominant negative allele to select for offspring with a desired trait and a stable genome. Another alternative is to use a CRE-LOX expression system, whereby the dominant negative allele is spliced from the animal genome once an animal containing a genetically diverse immunoglobulin profile has been established. Yet another alternative is the use of inducible vectors such as the steroid induced pIND (Invitrogen) or pMAM (Clonetech) vectors which express exogenous genes in the presence of corticosteroids.

Mutations can be detected by analyzing for alterations in the genotype of the cells or animals, for example by examining the sequence of genomic DNA, cDNA, messenger RNA, or amino acids associated with the gene of interest. Mutations can also be detected by screening for the production of antibody titers. A mutant polypeptide can be detected by identifying alterations in electrophoretic mobility, spectroscopic properties, or other physical or structural characteristics of a protein encoded by a mutant gene. One can also screen for altered function of the protein in situ, in isolated form, or in model systems. One can screen for alteration of any property of the cell or animal associated with the function of the gene of interest, such as but not limited to Ig secretion.

Examples of mismatch repair proteins and nucleic acid sequences include the following:

```
PMS2 (mouse) (SEQ ID NO:5)
MEQTEGVSTE CAKAIKPIDG KSVHQICSGQ VILSLSTAVK ELIENSVDAG ATTIDLRLKD    60

YGVDLIEVSD NGCGVEEENF EGLALKHHTS KIQEFADLTQ VETFGFRGEA LSSLCALSDV   120

TISTCHGSAS VGTRLVFDHN GKITQKTPYP RPKGTTVSVQ HLFYTLPVRY KEFQRNIKKE   180

YSKMVQVLQA YCIISAGVRV SCTNQLGQGK RHAVVCTSGT SGMKENIGSV FGQKQLQSLI   240

PFVQLPPSDA VCEEYGLSTS GRHKTFSTFR ASFHSARTAP GGVQQTGSFS SSIRGPVTQQ   300

RSLSLSMRFY HMYNRHQYPF VVLNVSVDSE CVDINVTPDK RQILLQEEKL LLAVLKTSLI   360

GMFDSDANKL NVNQQPLLDV EGNLVKLHTA ELEKPVPGKQ DNSPSLKSTA DEKRVASISR   420

LREAFSLHPT KEIKSRGPET AELTRSFPSE KRGVLSSYPS DVISYRGLRG SQDKLVSPTD   480

SPGDCMDREK IEKDSGLSST SAGSEEEFST PEVASSFSSD YNVSSLEDRP SQETINCGDL   540

DCRPPGTGQS LKPEDHGYQC KALPLARLSP TNAKRFKTEE RPSNVNISQR LPGPQSTSAA   600

EVDVAIKMNK RIVLLEFSLS SLAKRMKQLQ HLKAQNKHEL SYRKFRAKIC PGENQAAEDE   660

LRKEISKSMF AEMEILGQFN LGFIVTKLKE DLFLVDQHAA DEKYNFEMLQ QHTVLQAQRL   720

ITPQTLNLTA VNEAVLIENL EIFRKNGFDF VIDEDAPVTE RAKLISLPTS KNWTFGPQDI   780
```

-continued

DELIFMLSDS PGVMCRPSRV RQHFASRACR KSVMIGTALN ASEMKKLITH HGEMDHPWNC 840

PHGRPTMRHV ANLDVISQN 859

PMS2 (mouse cDNA) (SEQ ID NO:6)

gaattccggt gaaggtcctg aagaatttcc agattcctga gtatcattgg aggagacaga 60
taacctgtcg tcaggtaacg atggtgtata tgcaacagaa atgggtgttc ctggagacgc 120
gtcttttccc gagagcggca ccgcaactct cccgcggtga ctgtgactgg aggagtcctg 180
catccatgga gcaaaccgaa ggcgtgagta cagaatgtgc taaggccatc aagcctattg 240
atgggaagtc agtccatcaa atttgttctg ggcaggtgat actcagttta agcaccgctg 300
tgaaggagtt gatagaaaat agtgtagatg ctggtgctac tactattgat ctaaggctta 360
aagactatgg ggtggacctc attgaagttt cagacaatgg atgtggggta gaagaagaaa 420
actttgaagg tctagctctg aaacatcaca catctaagat tcaagagttt gccgacctca 480
cgcaggttga aactttcggc tttcgggggg aagctctgag ctctctgtgt gcactaagtg 540
atgtcactat atctacctgc cacgggtctg caagcgttgg gactcgactg gtgtttgacc 600
ataatgggaa aatcacccag aaaactccct acccccgacc taaaggaacc acagtcagtg 660
tgcagcactt attttataca ctacccgtgc gttacaaaga gtttcagagg aacattaaaa 720
aggagtattc caaaatggtg caggtcttac aggcgtactg tatcatctca gcaggcgtcc 780
gtgtaagctg cactaatcag ctcggacagg ggaagcggca cgctgtggtg tgcacaagcg 840
gcacgtctgg catgaaggaa aatatcgggt ctgtgtttgg ccagaagcag ttgcaaagcc 900
tcattccttt tgttcagctg ccccctagtg acgctgtgtg tgaagagtac ggcctgagca 960
cttcaggacg cccacaaaacc ttttctacgt ttcgggcttc atttcacagt gcacgcacgg 1020
cgccgggagg agtgcaacag acaggcagtt tttcttcatc aatcagaggc cctgtgaccc 1080
agcaaaggtc tctaagcttg tcaatgaggt tttatcacat gtataaccgg catcagtacc 1140
catttgtcgt ccttaacgtt tccgttgact cagaatgtgt ggatattaat gtaactccag 1200
ataaaaggca aattctacta caagaagaga agctattgct ggccgtttta aagacctcct 1260
tgataggaat gtttgacagt gatgcaaaca agcttaatgt caaccagcag ccactgctag 1320
atgttgaagg taacttagta aagctgcata ctgcagaact agaaaagcct gtgccaggaa 1380
agcaagataa ctctccttca ctgaagagca cagcagacga gaaaagggta gcatccatct 1440
ccaggctgag agaggccttt tctcttcatc ctactaaaga gatcaagtct aggggtccag 1500
agactgctga actgacacgg agttttccaa gtgagaaaag ggcgtgttta tcctcttatc 1560
cttcagacgt catctcttac agaggcctcc gtggctcgca ggacaaattg gtgagtccca 1620
cggacagccc tggtgactgt atggacagag agaaaataga aaaagactca gggctcagca 1680
gcacctcagc tggctctgag gaagagttca gcaccccaga agtggccagt agctttagca 1740
gtgactataa cgtgagctcc ctagaagaca gaccttctca ggaaaccata aactgtggtg 1800
acctggactg ccgtcctcca ggtacaggac agtccttgaa gccagaagac catggatatc 1860
aatgcaaagc tctacctcta gctcgtctgt cacccacaaa tgccaagcgc ttcaagacag 1920
aggaaagacc ctcaaatgtc aacatttctc aaagattgcc tggtcctcag agcacctcag 1980
cagctgaggt cgatgtagcc ataaaaatga ataagagaat cgtgctcctc gagttctctc 2040
tgagttctct agctaagcga atgaagcagt tacagcacct aaaggcgcag aacaaacatg 2100
aactgagtta cagaaaattt agggccaaga tttgccctgg agaaaaccaa gcagcagaag 2160
atgaactcag aaaagagatt agtaaatcga tgtttgcaga gatggagatc ttgggtcagt 2220

-continued

```
ttaacctggg atttatagta accaaactga aagaggacct cttcctggtg gaccagcatg      2280
ctgcggatga gaagtacaac tttgagatgc tgcagcagca cacggtgctc caggcgcaga      2340
ggctcatcac accccagact ctgaacttaa ctgctgtcaa tgaagctgta ctgatagaaa      2400
atctggaaat attcagaaag aatggctttg actttgtcat tgatgaggat gctccagtca      2460
ctgaaagggc taaattgatt tccttaccaa ctagtaaaaa ctggaccttt ggaccccaag      2520
atatagatga actgatcttt atgttaagtg acagccctgg ggtcatgtgc cggccctcac      2580
gagtcagaca gatgtttgct tccagagcct gtcggaagtc agtgatgatt ggaacggcgc      2640
tcaatgcgag cgagatgaag aagctcatca cccacatggg tgagatggac cacccctgga      2700
actgccccca cggcaggcca accatgaggc acgttgccaa tctggatgtc atctctcaga      2760
actgacacac cccttgtagc atagagttta ttacagattg ttcggtttgc aaagagaagg      2820
ttttaagtaa tctgattatc gttgtacaaa aattagcatg ctgctttaat gtactggatc      2880
catttaaaag cagtgttaag gcaggcatga tggagtgttc ctctagctca gctacttggg      2940
tgatccggtg ggagctcatg tgagcccagg actttgagac cactccgagc cacattcatg      3000
agactcaatt caaggacaaa aaaaaaaaga tatttttgaa gccttttaaa aaaaaa          3056
```

PMS2 (human) (SEQ ID NO:7)

```
MERAESSSTE PAKAIKPIDR KSVHQICSGQ VVLSLSTAVK ELVENSLDAG ATNIDLKLKD        60
YGVDLTEVSD NGCGVEEENF EGLTLKHHTS KIQEFADLTQ VETFGFRGEA LSSLCALSDV       120
TISTCHASAK VGTRLMFDHN GKIIQKTPYP RPRGTTVSVQ QLFSTLPVRH KEFQRNIKKE       180
YAKMVQVLHA YCIISAGIRV SCTNQLGQGK RQPVVCTGGS PSIKENIGSV FGQKQLQSLI       240
PFVQLPPSDS VCEEYGLSCS DALHNLFYIS GFISQCTHGV GRSSTDRQFF FINRRPCDPA       300
KVCRLVNEVY HMYNRHQYPF VVLNISVDSE CVDINVTPDK RQILLQEEKL LLAVLKTSLI       360
GMFDSDVNKL NVSQQPLLDV EGNLIKMHAA DLEKPMVEKQ DQSPSLRTGE EKKDVSISRL       420
REAFSLRHTT ENKPHSPKTP EPRRSPLGQK RGMLSSSTSG AISDKGVLRP QKEAVSSSHG       480
PSDPTDRAEV EKDSGHGSTS VDSEGFSIPD TGSHCSSEYA ASSPGDRGSQ EHVDSQEKAP       540
ETDDSFSDVD CHSNQEDTGC KFRVLPQPTN LATPNTKRFK KEEILSSSDI CQKLVNTQDM       600
SASQVDVAVK INKKVVPLDF SMSSLAKRIK QLHHEAQQSE GEQNYRKFRA KICPGENQAA       660
EDELRKEISK TMFAEMEIIG QFNLGFIITK LNEDIFIVDQ HATDEKYNFE MLQQHTVLQG       720
QRLIAPQTLN LTAVNEAVLI ENLEIFRKNG FDFVIDENAP VTERAKLISL PTSKNWTFGP       780
QDVDELIFML SDSPGVMCRP SRVKQMFASR ACRKSVMIGT ALNTSEMKKL ITHMGEMDHP       840
WNCPHGRPTM RHIANLGVIS QN                                                862
```

PMS2 (human cDNA) (SEQ ID NO:8)

```
cgaggcggat cgggtgttgc atccatggag cgagctgaga gctcgagtac agaacctgct        60
aaggccatca aacctattga tcggaagtca gtccatcaga tttgctctgg gcaggtggta       120
ctgagtctaa gcactgcggt aaaggagtta gtagaaaaca gtctggatgc tggtgccact       180
aatattgatc taaagcttaa ggactatgga gtggatctta ttgaagtttc agacaatgga       240
tgtggggtag aagaagaaaa cttcgaaggc ttaactctga aacatcacac atctaagatt       300
caagagtttg ccgacctaac tcaggttgaa acttttggct ttcgggggga agctctgagc       360
tcactttgtg cactgagcga tgtcaccatt tctacctgcc acgcatcggc gaaggttgga       420
actcgactga tgtttgatca caatgggaaa attatccaga aaacccccta cccccgcccc       480
agagggacca cagtcagcgt gcagcagtta ttttccacac tacctgtgcg ccataaggaa       540
```

-continued

```
tttcaaagga atattaagaa ggagtatgcc aaaatggtcc aggtcttaca tgcatactgt     600
atcatttcag caggcatccg tgtaagttgc accaatcagc ttggacaagg aaaacgacag     660
cctgtggtat gcacaggtgg aagccccagc ataaaggaaa atatcggctc tgtgtttggg     720
cagaagcagt tgcaaagcct cattcctttt gttcagctgc cccctagtga ctccgtgtgt     780
gaagagtacg gtttgagctg ttcggatgct ctgcataatc ttttttacat ctcaggtttc     840
atttcacaat gcacgcatgg agttggaagg agttcaacag acagacagtt tttctttatc     900
aaccggcggc cttgtgaccc agcaaaggtc tgcagactcg tgaatgaggt ctaccacatg     960
tataatcgac accagtatcc atttgttgtt cttaacattt ctgttgattc agaatgcgtt    1020
gatatcaatg ttactccaga taaaaggcaa attttgctac aagaggaaaa gcttttgttg    1080
gcagttttaa agacctcttt gataggaatg tttgatagtg atgtcaacaa gctaaatgtc    1140
agtcagcagc cactgctgga tgttgaaggt aacttaataa aaatgcatgc agcggatttg    1200
gaaaagccca tggtagaaaa gcaggatcaa tccccttcat taaggactgg agaagaaaaa    1260
aaagacgtgt ccatttccag actgcgagag gccttttctc ttcgtcacac aacagagaac    1320
aagcctcaca gcccaaagac tccagaacca agaaggagcc ctctaggaca gaaaaggggt    1380
atgctgtctt ctagcacttc aggtgccatc tctgacaaag gcgtcctgag acctcagaaa    1440
gaggcagtga gttccagtca cggacccagt gaccctacgg acagagcgga ggtggagaag    1500
gactcggggc acggcagcac ttccgtggat tctgaggggt tcagcatccc agacacgggc    1560
agtcactgca gcagcgagta tgcggccagc tccccagggg acaggggctc gcaggaacat    1620
gtggactctc acgagaaagc gcctgaaact gacgactctt tttcagatgt ggactgccat    1680
tcaaaccagg aagataccgg atgtaaattt cgagttttgc ctcagccaac taatctcgca    1740
accccaaaca caaagcgttt taaaaaagaa gaaattcttt ccagttctga catttgtcaa    1800
aagttagtaa atactcagga catgtcagcc tctcaggttg atgtagctgt gaaaattaat    1860
aagaaagttg tgcccctgga cttttctatg agttctttag ctaaacgaat aaagcagtta    1920
catcatgaag cacagcaaag tgaaggggaa cagaattaca ggaagtttag ggcaaagatt    1980
tgtcctggag aaaatcaagc agccgaagat gaactaagaa aagagataag taaaacgatg    2040
tttgcagaaa tggaaatcat tggtcagttt aacctgggat ttataataac caaactgaat    2100
gaggatatct tcatagtgga ccagcatgcc acggacgaga agtataactt cgagatgctg    2160
cagcagcaca ccgtgctcca ggggcagagg ctcatagcac ctcagactct caacttaact    2220
gctgttaatg aagctgttct gatagaaaat ctggaaatat ttagaaagaa tggctttgat    2280
tttgttatcg atgaaaatgc tccagtcact gaaagggcta aactgatttc cttgccaact    2340
agtaaaaact ggaccttcgg accccaggac gtcgatgaac tgatcttcat gctgagcgac    2400
agccctgggg tcatgtgccg gccttcccga gtcaagcaga tgtttgcctc cagagcctgc    2460
cggaagtcgg tgatgattgg gactgctctt aacacaagcg agatgaagaa actgatcacc    2520
cacatggggg agatggacca cccctggaac tgtccccatg gaaggccaac catgagacac    2580
atcgccaacc tgggtgtcat ttctcagaac tgaccgtagt cactgtatgg aataattggt    2640
tttatcgcag atttttatgt tttgaaagac agagtcttca ctaacctttt ttgttttaaa    2700
atgaaacctg ctacttaaaa aaaatacaca tcacacccat ttaaaagtga tcttgagaac    2760
cttttcaaac c                                                         2771
```

PMS1 (human) (SEQ ID NO:9)

```
MKQLPAATVR LLSSSQIITS VVSVVKELIE NSLDAGATSV DVKLENYGFD KIEVRDNGEG      60
```

-continued

```
IKAVDAPVMA MKYYTSKINS HEDLENLTTY GFRGEALGSI CCIAEVLITT RTAADNFSTQ        120
YVLDGSGHIL SQKPSHLGQG TTVTALRLFK NLPVRKQFYS TAKKCKDEIK KIQDLLMSFG        180
ILKPDLRIVF VHNKAVIWQK SRVSDHKMAL MSVLGTAVMN NMESFQYHSE ESQIYLSGFL        240
PKCDADHSFT SLSTPERSFI FINSRPVHQK DILKLIRHHY NLKCLKESTR LYPVFFLKID        300
VPTADVDVNL TPDKSQVLLQ NKESVLIALE NLMTTCYGPL PSTNSYENNK TDVSAADIVL        360
SKTAETDVLF NKVESSGKNY SNVDTSVIPF QNDMHNDESG KNTDDCLNHQ ISIGDFGYGH        420
CSSEISNIDK NTKNAFQDIS MSNVSWENSQ TEYSKTCFIS SVKHTQSENG NKDHIDESGE        480
NEEEAGLENS SEISADEWSR GNILKNSVGE NIEPVKILVP EKSLPCKVSN NNYPIFEQMN        540
LNEDSCNKKS NVIDNKSGKV TAYDLLSNRV IKKPMSASAL FVQDHRPQFL IENPKTSLED        600
ATLQIEELWK TLSEEEKLKY EEKATKDLER YNSQMKRAIE QESQMSLKDG RKKIKPTSAW        660
NLAQKKKLKT SLSNQPKLDE LLQSQIEKRR SQNIKMVQIP FSMKNLKINF KKQNKVDLEE        720
KDEPCLIHNL RFPDAWLMTS KTEVMLLNPY RVEEALLFKR LLENHKLPAE PLEKPIMLTE        780
SLFNGSHYLD VLYKMTADDQ RYSGSTYLSD PRLTANGFKI KLIPGVSITE NYLEIEGMAN        840
CLPFYGVADL KEILNAILNR NAKEVYECRP RKVISYLEGE AVRLSRQLPM YLSKEDIQDI        900
IYRMKHQFGN EIKECVHGRP FFHHLTYLPE TT                                      932
```

PMS1 (human) (SEQ ID NO:10)

```
ggcacgagtg gctgcttgcg gctagtggat ggtaattgcc tgcctcgcgc tagcagcaag         60
ctgctctgtt aaaagcgaaa atgaaacaat tgcctgcggc aacagttcga ctcctttcaa        120
gttctcagat catcacttcg gtggtcagtg ttgtaaaaga gcttattgaa aactccttgg        180
atgctggtgc cacaagcgta gatgttaaac tggagaacta tggatttgat aaaattgagg        240
tgcgagataa cggggagggt atcaaggctg ttgatgcacc tgtaatggca atgaagtact        300
acacctcaaa aataaatagt catgaagatc ttgaaaattt gacaacttac ggtttttcgtg        360
gagaagcctt ggggtcaatt tgttgtatag ctgaggtttt aattacaaca agaacggctg        420
ctgataattt tagcacccag tatgttttag atggcagtgg ccacatactt tctcagaaac        480
cttcacatct tggtcaaggt acaactgtaa ctgctttaag attatttaag aatctacctg        540
taagaaagca gttttactca actgcaaaaa aatgtaaaga tgaaataaaa aagatccaag        600
atctcctcat gagctttggt atccttaaac ctgacttaag gattgtcttt gtacataaca        660
aggcagttat ttggcagaaa agcagagtat cagatcacaa gatggctctc atgtcagttc        720
tggggactgc tgttatgaac aatatggaat cctttcagta ccactctgaa gaatctcaga        780
tttatctcag tggatttctt ccaaagtgtg atgcagacca ctctttcact agtctttcaa        840
caccagaaag aagtttcatc ttcataaaca gtcgaccagt acatcaaaaa gatatcttaa        900
agttaatccg acatcattac aatctgaaat gcctaaagga atctactcgt ttgtatcctg        960
ttttctttct gaaaatcgat gttcctacag ctgatgttga tgtaaattta acaccagata       1020
aaagccaagt attattacaa aataaggaat ctgttttaat tgctcttgaa aatctgatga       1080
cgacttgtta tggaccatta cctagtacaa attcttatga aaataataaa acagatgttt       1140
ccgcagctga catcgttctt agtaaaacag cagaaacaga tgtgcttttt aataaagtgg       1200
aatcatctgg aaagaattat tcaaatgttg atacttcagt cattccattc caaaatgata       1260
tgcataatga tgaatctgga aaaaacactg atgattgttt aaatcaccag ataagtattg       1320
gtgactttgg ttatggtcat tgtagtagtg aaatttctaa cattgataaa aacactaaga       1380
atgcatttca ggacatttca atgagtaatg tatcatggga gaactctcag acggaatata       1440
```

-continued

```
gtaaaacttg ttttataagt tccgttaagc acacccagtc agaaaatggc aataaagacc      1500
atatagatga gagtggggaa aatgaggaag aagcaggtct tgaaaactct tcggaaattt      1560
ctgcagatga gtggagcagg ggaaatatac ttaaaaattc agtgggagag aatattgaac      1620
ctgtgaaaat tttagtgcct gaaaaaagtt taccatgtaa agtaagtaat aataattatc      1680
caatccctga acaaatgaat cttaatgaag attcatgtaa caaaaaatca aatgtaatag      1740
ataataaatc tggaaaagtt acagcttatg atttacttag caatcgagta atcaagaaac      1800
ccatgtcagc aagtgctctt tttgttcaag atcatcgtcc tcagtttctc atagaaaatc      1860
ctaagactag tttagaggat gcaacactac aaattgaaga actgtggaag acattgagtg      1920
aagaggaaaa actgaaatat gaagagaagg ctactaaaga cttggaacga tacaatagtc      1980
aaatgaagag agccattgaa caggagtcac aaatgtcact aaaagatggc agaaaaaaga      2040
taaaacccac cagcgcatgg aatttggccc agaagcacaa gttaaaaacc tcattatcta      2100
atcaaccaaa acttgatgaa ctccttcagt cccaaattga aaaaagaagg agtcaaaata      2160
ttaaaatggt acagatcccc ttttctatga aaaacttaaa aataaatttt aagaaacaaa      2220
acaaagttga cttagaagag aaggatgaac cttgcttgat ccacaatctc aggtttcctg      2280
atgcatggct aatgacatcc aaaacagagg taatgttatt aaatccatat agagtagaag      2340
aagccctgct atttaaaaga cttcttgaga atcataaact tcctgcagag ccactggaaa      2400
agccaattat gttaacagag agtcttttta atggatctca ttatttagac gttttatata      2460
aaatgacagc agatgaccaa agatacagtg gatcaactta cctgtctgat cctcgtctta      2520
cagcgaatgg tttcaagata aaattgatac caggagtttc aattactgaa aattacttgg      2580
aaatagaagg aatggctaat tgtctcccat tctatggagt agcagattta aaagaaattc      2640
ttaatgctat attaaacaga aatgcaaagg aagtttatga atgtagacct cgcaaagtga      2700
taagttattt agagggagaa gcagtgcgtc tatccagaca attacccatg tacttatcaa      2760
aagaggacat ccaagacatt atctacagaa tgaagcacca gtttggaaat gaaattaaag      2820
agtgtgttca tggtcgccca ttttttcatc atttaaccta tcttccagaa actacatgat      2880
taaatatgtt taagaagatt agttaccatt gaaattggtt ctgtcataaa acagcatgag      2940
tctggtttta aattatcttt gtattatgtg tcacatggtt attttttaaa tgaggattca      3000
ctgacttgtt tttatattga aaaaagttcc acgtattgta gaaaacgtaa ataaactaat      3060
aac                                                                    3063
```

MSH2 (human) (SEQ ID NO:11)

```
MAVQPKETLQ LESAAEVGFV RFFQGMPEKP TTTVRLFDRG DFYTAHGEDA LLAAREVFKT        60
QGVIKYMGPA GAKNLQSVVL SKMNFESFVK DLLLVRQYRV EVYKNRAGNK ASKENDWYLA       120
YKASPGNLSQ FEDILFGNND MSASIGVVGV KMSAVDGQRQ VGVGYVDSIQ RKLGLCEFPD       180
NDQFSNLEAL LIQIGPKECV LPGGETAGDM GKLRQIIQRG GILITERKKA DFSTKDIYQD       240
LNRLLKGKKG EQMNSAVLPE MENQVAVSSL SAVIKFLELL SDDSNFGQFE LTTFDFSQYM       300
KLDIAAVRAL NLFQGSVEDT TGSQSLAALL NKCKTPQGQR LVNQWIKQPL MDKNRIEERL       360
NLVEAFVEDA ELRQTLQEDL LRRFPDLNRL AKKFQRQAAN LQDCYRLYQG INQLPNVIQA       420
LEKHEGKHQK LLLAVFVTPL TDLRSDFSKF QEMIETTLDM DQVENHEFLV KPSFDPNLSE       480
LREIMNDLEK KMQSTLISAA RDLGLDPGKQ IKLDSSAQFG YYFRVTCKEE KVLRNNKNFS       540
TVDIQKNGVK FTNSKLTSLN EEYTKNKTEY EEAQDAIVKE IVNISSGYVE PMQTLNDVLA       600
QLDAVVSFAH VSNGAPVPYV RPAILEKGQG RIILKASRHA CVEVQDEIAF IPNDVYFEKD       660
```

-continued

```
KQMFHIITGP NMGGKSTYIR QTGVIVLHAQ IGCFVPCESA EVSIVDCILA RVGAGDSQLK        720
GVSTFMAEML ETASILRSAT KDSLIIIDEL GRGTSTYDGF GLAWAISEYI ATKIGAFCMF        780
ATHFHELTAL ANQIPTVNNL HVTALTTEET LTMLYQVKKG VCDQSFGIHV AELANFPKHV        840
IECAKQKALE LEEFQYIGES QGYDIMEPAA KKCYLEREQG EKIIQEFLSK VKQMPFTEMS        900
EENITIKLKQ LKAEVIAKNN SFVNEIISRI KVTT                                    934
```

MSH2 (human cDNA) (SEQ ID NO:12)

```
ggcgggaaac agcttagtgg gtgtggggtc gcgcattttc ttcaaccagg aggtgaggag         60
gtttcgacat ggcggtgcag ccgaaggaga cgctgcagtt ggagagcgcg gccgaggtcg        120
gcttcgtgcg cttctttcag ggcatgccgg agaagccgac caccacagtg cgccttttcg        180
accggggcga cttctatacg gcgcacggcg aggacgcgct gctggccgcc cgggaggtgt        240
tcaagaccca gggggtgatc aagtacatgg ggccggcagg agcaaagaat ctgcagagtg        300
ttgtgcttag taaaatgaat tttgaatctt ttgtaaaaga tcttcttctg gttcgtcagt        360
atagagttga agtttataag aatagagctg gaaataaggc atccaaggag aatgattggt        420
atttggcata taaggcttct cctggcaatc tctctcagtt tgaagacatt ctctttggta        480
acaatgatat gtcagcttcc attggtgttg tgggtgttaa aatgtccgca gttgatggcc        540
agagacaggt tggagttggg tatgtggatt ccatacagag gaaactagga ctgtgtgaat        600
tccctgataa tgatcagttc tccaatcttg aggctctcct catccagatt ggaccaaagg        660
aatgtgtttt acccggagga gagactgctg gagacatggg gaaactgaga cagataattc        720
aaagaggagg aattctgatc acagaaagaa aaaaagctga cttttccaca aaagacattt        780
atcaggacct caaccggttg ttgaaaggca aaaagggaga gcagatgaat agtgctgtat        840
tgccagaaat ggagaatcag gttgcagttt catcactgtc tgcggtaatc aagtttttag        900
aactcttatc agatgattcc aactttggac agtttgaact gactactttt gacttcagcc        960
agtatatgaa attggatatt gcagcagtca gagcccttaa cctttttcag ggttctgttg       1020
aagataccac tggctctcag tctctggctg ccttgctgaa taagtgtaaa acccctcaag       1080
gacaaagact tgttaaccag tggattaagc agcctctcat ggataagaac agaatagagg       1140
agagattgaa tttagtggaa gcttttgtag aagatgcaga attgaggcag actttacaag       1200
aagatttact tcgtcgattc ccagatctta accgacttgc caagaagttt caaagacaag       1260
cagcaaactt acaagattgt taccgactct atcagggtat aaatcaacta cctaatgtta       1320
tacaggctct ggaaaaacat gaaggaaaac accagaaatt attgttggca gtttttgtga       1380
ctcctcttac tgatcttcgt tctgacttct ccaagtttca ggaaatgata gaaacaactt       1440
tagatatgga tcaggtggaa aaccatgaat tccttgtaaa accttcattt gatcctaatc       1500
tcagtgaatt aagagaaata atgaatgact tggaaaagaa gatgcagtca acattaataa       1560
gtgcagccag agatcttggc ttggaccctg gcaaacagat taaactggat tccagtgcac       1620
agtttggata ttactttcgt gtaacctgta aggaagaaaa agtccttcgt aacaataaaa       1680
actttagtac tgtagatatc cagaagaatg gtgttaaatt taccaacagc aaattgactt       1740
ctttaaatga agagtatacc aaaaataaaa cagaatatga agaagcccag gatgccattg       1800
ttaaagaaat tgtcaatatt tcttcaggct atgtagaacc aatgcagaca ctcaatgatg       1860
tgttagctca gctagatgct gttgtcagct ttgctcacgt gtcaaatgga gcacctgttc       1920
catatgtacg accagccatt ttggagaaag gacaaggaag aattatatta aaagcatcca       1980
ggcatgcttg tgttgaagtt caagatgaaa ttgcatttat tcctaatgac gtatactttg       2040
```

-continued

```
aaaaagataa acagatgttc cacatcatta ctggccccaa tatgggaggt aaatcaacat      2100
atattcgaca aactggggtg atagtactca tggcccaaat tgggtgtttt gtgccatgtg      2160
agtcagcaga agtgtccatt gtggactgca tcttagcccg agtaggggct ggtgacagtc      2220
aattgaaagg agtctccacg ttcatggctg aaatgttgga aactgcttct atcctcaggt      2280
ctgcaaccaa agattcatta ataatcatag atgaattggg aagaggaact tctacctacg      2340
atggatttgg gttagcatgg gctatatcag aatacattgc aacaaagatt ggtgcttttt      2400
gcatgtttgc aacccatttt catgaactta ctgccttggc caatcagata ccaactgtta      2460
ataatctaca tgtcacagca ctcaccactg aagagacctt aactatgctt tatcaggtga      2520
agaaaggtgt ctgtgatcaa agttttggga ttcatgttgc agagcttgct aatttcccta      2580
agcatgtaat agagtgtgct aaacagaaag ccctggaact tgaggagttt cagtatattg      2640
gagaatcgca aggatatgat atcatggaac cagcagcaaa gaagtgctat ctggaaagag      2700
agcaaggtga aaaaattatt caggagttcc tgtccaaggt gaaacaaatg ccctttactg      2760
aaatgtcaga agaaaacatc acaataaagt taaaacagct aaaagctgaa gtaatagcaa      2820
agaataatag ctttgtaaat gaaatcattt cacgaataaa agttactacg tgaaaaatcc      2880
cagtaatgga atgaaggtaa tattgataag ctattgtctg taatagtttt atattgtttt      2940
atattaaccc tttttccata gtgttaactg tcagtgccca tgggctatca acttaataag      3000
atatttagta atattttact ttgaggacat tttcaaagat tttattttg aaaaatgaga      3060
gctgtaactg aggactgttt gcaattgaca taggcaataa taagtgatgt gctgaatttt      3120
ataaataaaa tcatgtagtt tgtgg                                          3145
```

MLH1 (human) (SEQ ID NO:13)

```
MSFVAGVIRR LDETVVNRIA AGEVIQRPAN AIKEMIENCL DAKSTSIQVI VKEGGLKLIQ       60
IQDNGTGIRK EDLDIVCERF TTSKLQSFED LASISTYGFR GEALASISHV AHVTITTKTA      120
DGKCAYRASY SDGKLKAPPK PCAGNQGTQI TVEDLFYNIA TRRKALKNPS EEYGKILEVV      180
GRYSVHNAGI SFSVKKQGET VADVRTLPNA STVDNIRSIF GNAVSRELIE IGCEDKTLAF      240
KMNGYISNAN YSVKKCIFLL FINHRLVEST SLRKAIETVY AAYLPKNTHP FLYLSLEISP      300
QNVDVNVHPT KMEVHFLHEE SILERVQQHI ESKLLGSNSS RMYFTQTLLP GLAGPSGEMV      360
KSTTSLTSSS TSGSSDKVYA HQMVRTDSRE QKLDAFLQPL SKPLSSQPQA IVTEDKTDIS      420
SGRARQQDEE MLELPAPAEV AAKNQSLEGD TTKGTSEMSE KRGPTSSNPR KRHREDSDVE      480
MVEDDSRKEM TAACTPRRRI INLTSVLSLQ EEINEQGHEV LREMLHNHSF VGCVNPQWAL      540
AQHQTKLYLL NTTKLSEELF YQILIYDFAN FGVLRLSEPA PLFDLAMLAL DSPESGWTEE      600
DGPKEGLAEY IVEFLKKKAE MLADYFSLEI DEEGNLIGLP LLIDNYVPPL EGLPIFILRL      660
ATEVNWDEEK ECFESLSKEC AMFYSIRKQY ISEESTLSGQ QSEVPGSIPN SWKWTVEHIV      720
YKALRSHILP PKHFTEDGNI LQLANLPDLY KVFERC                                756
```

MLH1 (human) (SEQ ID NO:14)

```
cttggctctt ctggcgccaa aatgtcgttc gtggcagggg ttattcggcg gctggacgag        60
acagtggtga accgcatcgc ggcgggggaa gttatccagc ggccagctaa tgctatcaaa       120
gagatgattg agaactgttt agatgcaaaa tccacaagta ttcaagtgat tgttaaagag       180
ggaggcctga agttgattca gatccaagac aatggcaccg ggatcaggaa agaagatctg       240
gatattgtat gtgaaaggtt cactactagt aaactgcagt cctttgagga tttagccagt       300
atttctacct atggctttcg aggtgaggct ttggccagca taagccatgt ggctcatgtt       360
```

-continued

```
actattacaa cgaaaacagc tgatggaaag tgtgcataca gagcaagtta ctcagatgga     420
aaactgaaag cccctcctaa accatgtgct ggcaatcaag ggacccagat cacggtggag     480
gaccttttt acaacatagc cacgaggaga aaagctttaa aaaatccaag tgaagaatat      540
gggaaaattt tggaagttgt tggcaggtat tcagtacaca atgcaggcat tagtttctca     600
gttaaaaaac aaggagagac agtagctgat gttaggacac tacccaatgc ctcaaccgtg     660
gacaatattc gctccatctt tggaaatgct gttagtcgag aactgataga aattggatgt     720
gaggataaaa ccctagcctt caaaatgaat ggttacatat ccaatgcaaa ctactcagtg     780
aagaagtgca tcttcttact cttcatcaac catcgtctgg tagaatcaac ttccttgaga     840
aaagccatag aaacagtgta tgcagcctat ttgcccaaaa acacacaccc attcctgtac     900
ctcagtttag aaatcagtcc ccagaatgtg gatgttaatg tgcaccccac aaagcatgaa     960
gttcacttcc tgcacgagga gagcatcctg gagcgggtgc agcagcacat cgagagcaag    1020
ctcctgggct ccaattcctc caggatgtac ttcacccaga ctttgctacc aggacttgct    1080
ggcccctctg ggagatggt taaatccaca acaagtctga cctcgtcttc tacttctgga     1140
agtagtgata aggtctatgc ccaccagatg gttcgtacag attcccggga acagaagctt    1200
gatgcatttc tgcagcctct gagcaaaccc ctgtccagtc agccccaggc cattgtcaca    1260
gaggataaga cagatatttc tagtggcagg gctaggcagc aagatgagga gatgcttgaa    1320
ctcccagccc ctgctgaagt ggctgccaaa aatcagagct tggagggga tacaacaaag     1380
gggacttcag aaatgtcaga gaagagagga cctacttcca gcaaccccag aaagagacat    1440
cgggaagatt ctgatgtgga aatggtggaa gatgattccc gaaaggaaat gactgcagct    1500
tgtacccccc ggagaaggat cattaacctc actagtgttt tgagtctcca ggaagaaatt    1560
aatgagcagg gacatgaggt tctccgggag atgttgcata accactcctt cgtgggctgt    1620
gtgaatcctc agtgggcctt ggcacagcat caaaccaagt tataccttct caacaccacc    1680
aagcttagtg aagaactgtt ctaccagata ctcatttatg attttgccaa ttttggtgtt    1740
ctcaggttat cggagccagc accgctcttt gaccttgcca tgcttgcctt agatagtcca    1800
gagagtggct ggacagagga agatggtccc aaagaaggac ttgctgaata cattgttgag    1860
tttctgaaga agaaggctga gatgcttgca gactatttct ctttggaaat tgatgaggaa    1920
gggaacctga ttggattacc ccttctgatt gacaactatg tgccccttt ggagggactg      1980
cctatcttca ttcttcgact agccactgag gtgaattggg acgaagaaaa ggaatgtttt    2040
gaaagcctca gtaaagaatg cgctatgttc tattccatcc ggaagcagta catatctgag    2100
gagtcgaccc tctcaggcca gcagagtgaa gtgcctggct ccattccaaa ctcctggaag    2160
tggactgtgg aacacattgt ctataaagcc ttgcgctcac acattctgcc tcctaaacat    2220
ttcacagaag atggaaatat cctgcagctt gctaacctgc ctgatctata caaagtcttt    2280
gagaggtgtt aaatatggtt atttatgcac tgtgggatgt gttcttcttt ctctgtattc    2340
cgatacaaag tgttgtatca aagtgtgata tacaaagtgt accaacataa gtgttggtag    2400
cacttaagac ttatacttgc cttctgatag tattccttta tacacagtgg attgattata    2460
aataaataga tgtgtcttaa cata                                           2484
```

hPMS2-134 (human) (SEQ ID NO:15)

```
MERAESSSTE PAKAIKPIDR KSVHQICSGQ VVLSLSTAVK ELVENSLDAG ATNIDLKLKD      60
YGVDLIEVSD NGCGVEEENF EGLTLKHHTS KIQEFADLTQ VETFGFRGEA LSSLCALSDV     120
TISTCHASAK VGT                                                        133
```

-continued hPMS2-134 (human cDNA) (SEQ ID NO:16)

```
cgaggcggat cgggtgttgc atccatggag cgagctgaga gctcgagtac agaacctgct    60

aaggccatca aacctattga tcggaagtca gtccatcaga tttgctctgg gcaggtggta   120

ctgagtctaa gcactgcggt aaaggagtta gtagaaaaca gtctggatgc tggtgccact   180

aatattgatc taaagcttaa ggactatgga gtggatctta ttgaagtttc agacaatgga   240

tgtggggtag aagaagaaaa cttcgaaggc ttaactctga aacatcacac atctaagatt   300

caagagtttg ccgacctaac tcaggttgaa acttttggct ttcgggggga agctctgagc   360

tcactttgtg cactgagcga tgtcaccatt tctacctgcc acgcatcggc gaaggttgga   420

acttga                                                              426
```

For further information on the background of the invention the following references may be consulted, each of which is incorporated herein by reference in its entirety:

1. Glaser, V. (1996) Can ReoPro repolish tarnished monoclonal therapeutics? *Nat. Biotechol.* 14:1216–1217.
2. Weiner, L. M. (1999) Monoclonal antibody therapy of cancer. *Semin. Oncol.* 26:43–51.
3. Saez-Llorens, X. E. et al. (1998) Safety and pharmacokinetics of an intramuscular humanized monoclonal antibody to respiratory syncytial virus in premature infants and infants with bronchopulmonary dysplasia *Pediat. Infect. Dis. J.* 17:787–791.
4. Shield, C. F. et al. (1996) A cost-effective analysis of OKT3 induction therapy in cadaveric kidney transplantation. *Am J. Kidney Dis.* 27:855–864.
5. Khazaeli, M. B. et al. (1994) Human immune response to monoclonal antibodies. *J. Immunother.* 15:42–52.
6. Emery, S. C. and W. J. Harris "Strategies for humanizing antibodies" In: ANTIBODY ENGINEERING C. A. K. Borrebaeck (Ed.) Oxford University Press, N.Y. 1995, pp. 159–183.
7. U.S. Pat. No. 5,530,101to Queen and Selick.
8. Reff, M. E. (1993) High-level production of recombinant immunoglobulins in mammalian cells. *Curr. Opin. Biotechnol.* 4:573–576.
9. Neuberger, M. and M. Gruggermann, (1997) Monoclonal antibodies. Mice perform a human repertoire. *Nature* 386:25–26.
10. Fiedler, U. and U. Conrad (1995) High-level production and long-term storage of engineered antibodies in transgenic tobacco seeds. *Bio/Technology,* 13:1090–1093.
11. Baker S. M. et al. (1995) Male defective in the DNA mismatch repair gene PMS2 exhibit abnormal chromosome synapsis in meiosis. *Cell* 82:309–319.
12. Bronner, C. E. et al. (1994) Mutation in the DNA mismatch repair gene homologue hMLH1 is associated with hereditary non-polyposis colon cancer. *Nature* 368:258–261.
13. de Wind N. et al. (1995) Inactivation of the mouse Msh2 gene results in mismatch repair deficiency, methylation tolerance, hyperrecombination, and predisposition to cancer. *Cell* 82:321–300.
14. Drummond, J. T. et al. (1995) Isolation of an hMSH2-p160 heterodimer that restores mismatch repair to tumor cells. *Science* 268:1909–1912.
15. Modrich, P. (1994) Mismatch repair, genetic stability, and cancer. *Science* 266:1959–1960.
16. Nicolaides, N. C. et al. (1998) A Naturally Occurring hPMS2 Mutation Can Confer a Dominant Negative Mutator Phenotype. *Mol. Cell. Biol.* 18:1635–1641.
17. Prolla, T. A. et al. (1994) MLH1, PMS1, and MSH2 Interaction during the initiation of DNA mismatch repair in yeast. *Science* 264:1091–1093.
18. Strand, M. et al. (1993) Destabilization of tracts of simple repetitive DNA in yeast by mutations affecting DNA mismatch repair. *Nature* 365:274–276.
19. Su, S. S., R. S. Lahue, K. G. Au, and P. Modrich (1988) Mispair specificity of methyl directed DNA mismatch corrections in vitro. *J. Biol. Chem.* 263:6829–6835.
20. Parsons, R. et al. (1993) Hypermutability and mismatch repair deficiency in RER tumor cells. *Cell* 75:1227–1236.
21. Papadopoulos, N. et al. (1993) Mutation of a mutL homolog is associated with hereditary colon cancer. *Science* 263:1625–1629.
22. Perucho, M. (1996) Cancer of the microsatellite mutator phenotype. *Biol. Chem.* 377:675–684.
23. Nicolaides N. C., K. W. Kinzler , and B. Vogelstein (1995) Analysis of the 5' region of PMS2 reveals heterogenous transcripts and a novel overlapping gene. *Genomics* 29:329–334.
24. Nicolaides, N. C. et al. (1995) Genomic organization of the human PMS2 gene family. *Genomics* 30:195–206.
25. Palombo, F. et al. (1994) Mismatch repair and cancer. *Nature* 36:417.
26. Eshleman J. R. and S. D. Markowitz (1996) Mismatch repair defects in human carcinogenesis. *Hum. Mol. Genet.* 5:1489–494.
27. Liu, T. et al. (2000) Microsatellite instability as a predictor of a mutation in a DNA mismatch repair gene in familial colorectal cancer. *Genes Chromosomes Cancer* 27:17–25.
28. Nicolaides, N. C. et al. (1992) The Jun family members, c-JUN and JUND, transactivate the human c-myb promoter via an Ap1 like element. *J. Biol. Chem.* 267:19665–19672.
29. Shields, R. L. et al. (1995) Anti-IgE monoclonal antibodies that inhibit allergen-specific histamine release. *Int. Arch. Allergy Immunol.* 107:412–413.
30. Frigerio L. et al. (2000) Assembly, secretion, and vacuolar delivery of a hybrid immunoglobulin in plants. *Plant Physiol.* 123:1483–1494.
31. Bignami M, (2000) Unmasking a killer: DNA 0(6)-methylguanine and the cytotoxicity of methylating agents. *Mutat. Res.* 462:71–82.
32. Drummond. J. T. et al. (1996) Cisplatin and adriamycin resistance are associated with MutLa and mismatch repair deficiency in an ovarian tumor cell line. *J. Biol. Chem.* 271 :9645–19648.
33. Galio. L. et al. (1999) ATP hydrolysis-dependent formation of a dynamic ternary nucleoprotein complex with MutS and MutL. *Nucl. Acids. Res.* 27:2325–23231.

The above disclosure generally describes the present invention. A more complete understanding can be obtained by reference to the following specific examples which are provided herein for purposes of illustration only, and are not intended to limit the scope of the invention.

EXAMPLE 1

Stable Expression of Dominant Negative MMR Genes in Hybridoma Cells

It has been previously shown by Nicolaides et al. (Nicolaides et al. (1998) A Naturally Occurring hPMS2 Mutation Can Confer a Dominant Negative Mutator Phenotype *Mol. Cell. Biol.* 18:1635–1641) that the expression of a dominant negative allele in an otherwise MMR proficient cell could render these host cells MMR deficient. The creation of MMR deficient cells can lead to the generation of genetic alterations throughout the entire genome of a host organisms offspring, yielding a population of genetically altered offspring or siblings that may produce biochemicals with altered properties. This patent application teaches of the use of dominant negative MMR genes in antibody-producing cells, including but not limited to rodent hybridomas, human hybridomas, chimeric rodent cells producing human immunoglobulin gene products, human cells expressing immunoglobulin genes, mammalian cells producing single chain antibodies, and prokaryotic cells producing mammalian immunoglobulin genes or chimeric immunoglobulin molecules such as those contained within single-chain antibodies. The cell expression systems described above that are used to produce antibodies are well known by those skilled in the art of antibody therapeutics.

To demonstrate the ability to create MMR defective hybridomas using dominant negative alleles of MMR genes, we first transfected a mouse hybridoma cell line that is known to produce and antibody directed against the human IgE protein with an expression vector containing the human PMS2 (cell line referred to as HBPMS2), the previously published dominant negative PMS2 mutant referred herein as PMS134 (cell line referred to as HB134), or with no insert (cell line referred to as HBvec). The results showed that the PMS134 mutant could indeed exert a robust dominant negative effect, resulting in biochemical and genetic manifestations of MMR deficiency. Unexpectedly was the finding that the full length PMS2 also resulted in a lower MMR activity while no effect was seen in cells containing the empty vector. A brief description of the methods is provided below.

The MMR proficient mouse H36 hybridoma cell line was transfected with various hPMS2 expression plasmids plus reporter constructs for assessing MMR activity. The MMR genes were cloned into the pEF expression vector, which contains the elongation factor promoter upstream of the cloning site followed by a mammalian polyadenylation signal. This vector also contains the NEOr gene that allows for selection of cells retaining this plasmid. Briefly, cells were transfected with 1 $\mu$g of each vector using polyliposomes following the manufacturer's protocol (Life Technologies). Cells were then selected in 0.5 mg/ml of G418 for 10 days and G418 resistant cells were pooled together to analyze for gene expression. The PEF construct contains an intron that separates the exon 1 of the EF gene from exon 2. which is juxtaposed to the 5' end of the polylinker cloning site. This allows for a rapid reverse transcriptase polymerase chain reaction (RT-PCR) screen for cells expressing the spliced products. At day 17, 100,000 cells were isolated and their RNA extracted using the trizol method as previously described (Nicolaides N. C., Kinzler. K. W., and Vogelstein, B. (1995) Analysis of the 5' region of PMS2 reveals heterogeneous transcripts and a novel overlapping gene. *Genomics* 29:329–334). RNAs were reverse transcribed using Superscript II (Life Technologies) and PCR amplified using a sense primer located in exon 1 of the EF gene (5'-ttt cgc aac ggg ttt gcc g-3') (SEQ ID NO: 17) and an antisense primer (5'-gtt tca gag tta agc ctt cg-3') (SEQ ID NO: 18) centered at nt 283 of the published human PMS2 cDNA, which will detect both the full length as well as the PMS134 gene expression. Reactions were carried out using buffers and conditions as previously described (Nicolaides. N. C. et al. (1995) Genomic organization of the human PMS2 gene family. *Genomics* 30:195–206), using tile following amplification parameters: 94° C. for 30 sec. 52° C. for 2 min. 72° C. for 2 min. for 30 cycles. Reactions were analyzed on agarose gels. FIG. 1 shows a representative example of PMS expression in stably transduced H36 cells.

Expression of the protein encoded by these genes were confirmed via western blot using a polyclonal antibody directed to the first 20 amino acids located in the N-terminus of the protein following the procedures previously described (data not shown) (Nicolaides et al. (1998) A Naturally Occurring hPMS2 Mutation Can Confer a Dominant Negative Mutator Phenotype. *Mol. Cell. Biol.* 18:1635–1641.

EXAMPLE 2 hPMS134 Causes a Defect in MMR Activity and Hypermutability in Hybridoma Cells

A hallmark of MMR deficiency is the generation of unstable microsatellite repeats in the genome of host cells. This phenotype is referred to as microsatellite instability (MI) (Modrich, P. (1994) Mismatch repair, genetic stability, and cancer *Science* 266:1959–1960; Palombo, F., et al. (1994) Mismatch repair and cancer *Nature* 36:417). MI consists of deletions and/or insertions within repetitive mono-, di- and/or tri nucleotide repetitive sequences throughout the entire genome of a host cell. Extensive genetic analysis eukaryotic cells have found that the only biochemical defect that is capable of producing MI is defective MMR (Strand, M., et al. (1993) Destabilization of tracts of simple repetitive DNA in yeast by mutations affecting DNA mismatch repair *Nature* 365:274–276; Perucho, M. (1996) Cancer of the microsatellite mutator phenotype. *Biol Chem.* 377:675–684; Eshleman J. R., and Markowitz, S. D. (1996) Mismatch repair defects in human carcinogenesis. *Hum. Mol. Genet.* 5:1489–494). In light of this unique feature that defective MMR has on promoting MI, it is now used as a biochemical marker to survey for lack of MMR activity within host cells (Perucho, M. (1996) Cancer of the microsatellite mutator phenotype. *Biol Chem.* 377:675–684; Eshleman J. R., and Markowitz, S. D. (1996) Mismatch repair defects in human carcinogenesis. *Hum. Mol. Genet.* 5:1489–494; Liu, T., et al. (2000) Microsatellite instability as a predictor of a mutation in a DNA mismatch repair gene in familial colorectal cancer *Genes Chromosomes Cancer* 27:17–25).

A method used to detect MMR deficiency in eukaryotic cells is to employ a reporter gene that has a polynucleotide repeat inserted within the coding region that disrupts its reading frame due to a frame shift. In the case where MMR is defective, the reporter gene will acquire random mutations (i.e. insertions and/or deletions) within the polynucleotide repeat yielding clones that contain a reporter with an open reading frame. We have employed the use of an MMR-sensitive reporter gene to measure for MMR activity in HBvec, HBPMS2, and HBPMS134 cells. The reporter construct used the pCAR-OF, which contains a hygromycin resistance (HYG) gene plus a β-galactosidase gene containing a 29 bp out-of-frame poly-CA tract at the 5' end of its coding region. The pCAR-OF reporter would not generate β-galactosidase activity unless a frame-restoring mutation (i.e., insertion or deletion) arose following transfection. HBvec, HBPMS2, and HB134 cells were each transfected with pCAR-OF vector in duplicate reactions following the protocol described in Example 1. Cells were selected in 0.5 mg/ml G418 and 0.5 mg/ml HYG to select for cells retaining both the MMR effector and the pCAR-OF reporter plasmids. All cultures transfected with the pCAR vector resulted in a similar number of HYG/G418 resistant cells. Cultures were then expanded and tested for β-galactosidase activity in situ as well as by biochemical analysis of cell extracts. For in situ analysis, 100,000 cells were harvested and fixed in 1% gluteraldehyde, washed in phosphate buffered saline solution and incubated in 1 ml of X-gal substrate solution [0.15 M NaCl, 1 mM $MgCl_2$, 3.3 mM $K_4Fe(CN)_6$, 3.3 mM $K_3Fe(CN)_6$, 0.2% X-Gal] in 24 well plates for 2 hours at 37° C. Reactions were stopped in 500 mM sodium bicarbonate solution and transferred to microscope slides for analysis. Three fields of 200 cells each were counted for blue (β-galactosidase positive cells) or white (β-galactosidase negative cells) to assess for MMR inactivation. Table 1 shows the results from these studies. While no β-galactosidase positive cells were observed in HBvec cells, 10% of the cells per field were β-galactosidase positive in HB134 cultures and 2% of the cells per field were β-galactosidase positive in HBPMS2 cultures.

Figure 2:
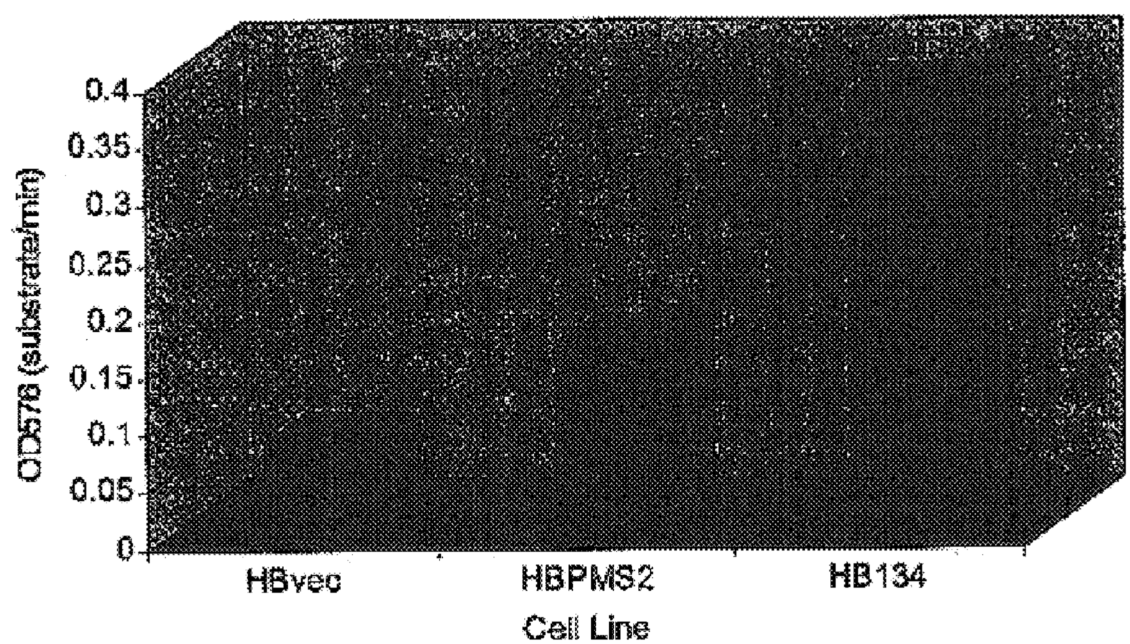
FIG. 2. Creation of genetically hypermutable hybridoma cells. Dominant negative MMR gene alleles were expressed in cells expressing a MMR-sensitive reporter gene. Dominant negative alleles such as PMS134 and the expression of MMR genes from other species results in antibody producer cells with a hypermutable phenotype that can be used to produce genetically altered immunoglobulin genes with enhanced biochemical features as well as lines with increased Ig expression and/or secretion. Values shown represent the amount of converted CPRG substrate which is reflective of the amount of function galactosidase contained within the cell from genetic alterations within the pCAR-OF reporter gene. Higher amounts of β-galactosidase activity reflect a higher mutation rate due to defective MMR.

Cell extracts were prepared from the above cultures to measure β-galactosidase using a quantitative biochemical assay as previously described (Nicolaides et al. (1998) A Naturally Occurring hPMS2 Mutation Can Confer a Dominant Negative Mutator Phenotype *Mol. Cell. Biol.* 18:1635–1641; Nicolaides, N. C., et al. (1992) The Jun family members, c-JUN and JUND, transactivate the human c-myb promoter via an Ap1 like element. *J. Biol. Chem.* 267:19665–19672). Briefly, 100,000 cells were collected, centrifuged and resuspended in 200 μls of 0.25M Tris, pH 8.0. Cells were lysed by freeze/thawing three times and supernatants collected after microfugation at 14,000 rpms to remove cell debris. Protein content was determined by spectrophotometric analysis at $OD^{280}$. For biochemical assays, 20 μg of protein was added to buffer containing 45 mM 2-mercaptoethanol, 1 nM $MgCl_2$, 0.1 M $NaPO_4$ and 0.6 mg/ml Chlorophenol red-β-D-galactopyranoside (CPRG, Boehringer Mannheim). Reactions were incubated for 1 hour, terminated by the addition of 0.5 M $Na_2CO_3$, and analyzed by spectrophotometry at 576 nm. H36 cell lysates were used to subtract out background. FIG. 2 shows the β-galactosidase activity in extracts from the various cell lines. As shown, the HB134 cells produced the highest amount of β-galactosidase, while no activity was found in the HBvec cells containing the pCAR-OF. These data demonstrate the ability to generate MMR defective hybridoma cells using dominant negative MMR gene alleles.

Table 1. β-galactosidase expression of HBvec, HBPMS2 and HB134 cells transfected with pCAR-OF reporter vectors. Cells were transfected with the pCAR-OF β-galactosidase reporter plasmid. Transfected cells were selected in hygromycin and G418, expanded and stained with X-gal solution to measure for β-galactosidase activity (blue colored cells). 3 fields of 200 cells each were analyzed by microscopy. The results below represent the mean +/−standard deviation of these experiments.

TABLE 1

| CELL LINE | # BLUE CELLS |
|---|---|
| HBvec | 0 +/− 0 |
| HBPMS2 | 4 +/− 1 |
| HB134 | 20 +/− 3 |

EXAMPLE 3

Figure 3:
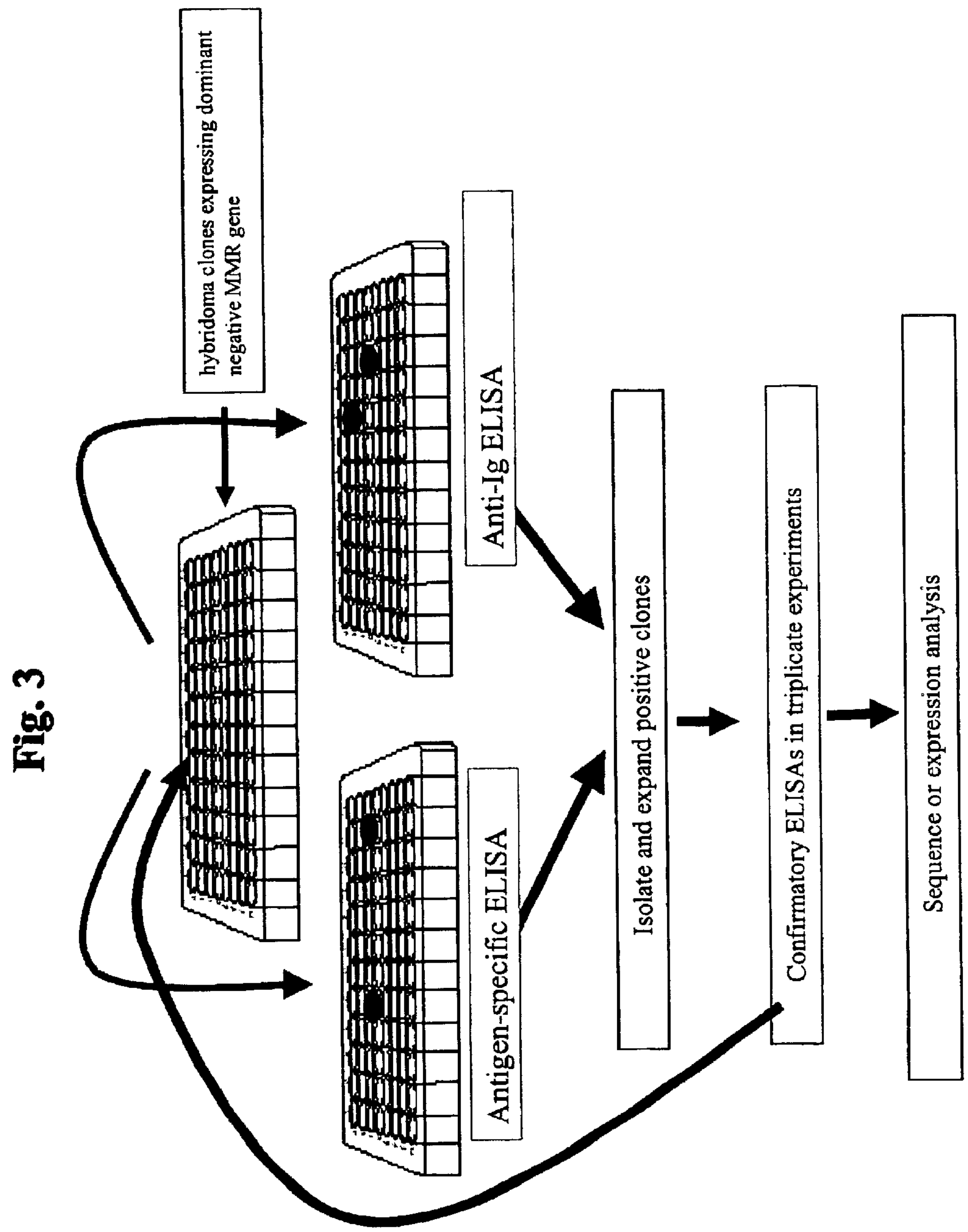
FIG. 3. Screening method for identifying antibody-producing cells containing antibodies with increased binding activity and/or increased expression/secretion FIG. 4. Generation of a genetically altered antibody with an increased binding activity. Shown are ELISA values from 96-well plates, screened for antibodies specific to hIgE. Two clones with a high binding value were found in HB134 cultures.
Figure 4:
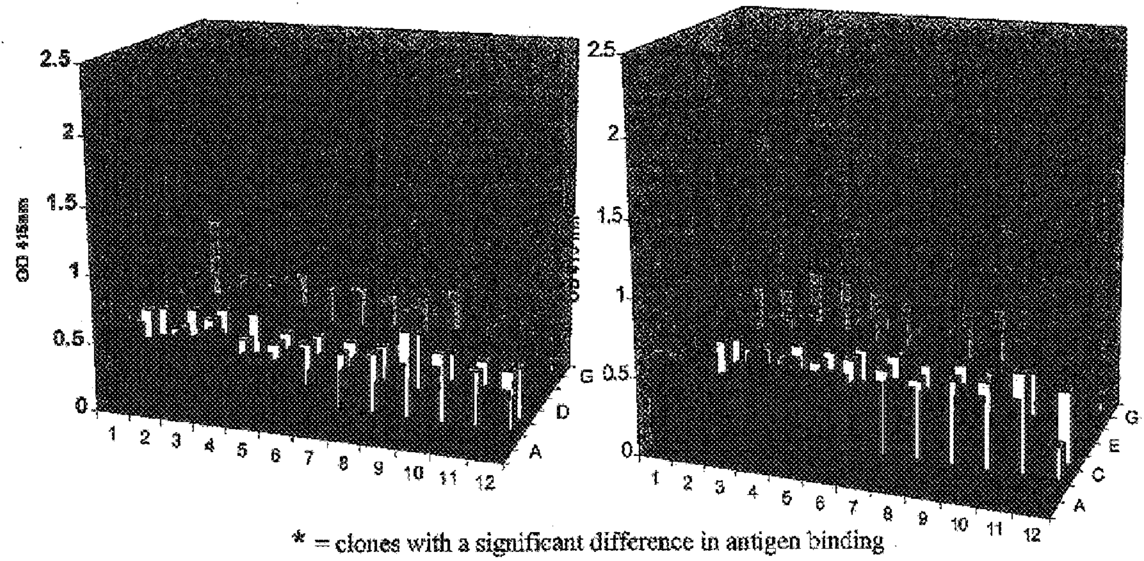

Screening Strategy to Identify Hybridoma Clones Producing Antibodies with Higher Binding Affinities and/or Increased Immunoglobulin Production An application of the methods presented within this document is the use of MMR deficient hybridomas or other immunoglobulin producing cells to create genetic alterations within an immunoglobulin gene that will yield antibodies with altered biochemical properties. An illustration of this application is demonstrated within this example whereby the HB134 hybridoma (see Example 1), which is a MMR-defective cell line that produces an anti-human immunoglobulin type E (hIgE) MAb, is grown for 20 generations and clones are isolated in 96-well plates and screened for hIgE binding. FIG. 3 outlines the screening procedure to identify clones that produce high affinity MAbs, which is presumed to be due to an alteration within the light or heavy chain variable region of the protein. The assay employs the use of a plate Enzyme Linked Immunosorbant Assay (ELISA) to screen for clones that produce high-affinity MAbs. 96-well plates containing single cells from HBvec or HB134 pools are grown for 9 days in growth medium (RPMI 1640 plus 10% fetal bovine serum) plus 0.5 mg/ml G418 to ensure clones retain the expression vector. After 9 days, plates are screened using an hIgE plate ELISA, whereby a 96 well plate is coated with 50 μls of a 1 μg/ml hIgE solution for 4 hours at 4° C. Plates are washed 3 times in calcium and magnesium free phosphate buffered saline solution ($PBS^{-/-}$) and blocked in 100 μls of $PBS^{-/-}$ with 5% dry milk for 1 hour at room temperature. Wells are rinsed and incubated with 100 μls of a PBS solution containing a 1:5 dilution of conditioned medium from each cell clone for 2 hours. Plates are then washed 3 times with $PBS^{-/-}$ and incubated for 1 hour at room temperature with 50 μls of a $PBS^{-\,-}$solution containing 1:3000 dilution of a sheep anti-mouse horse radish peroxidase (HRP) conjugated secondary antibody. Plates are then washed 3 times with $PBS^{-\,-}$ and incubated with 50 μls of TMB-HRP substrate (BioRad) for 15 minutes at room temperature to detect amount of antibody produced by each clone. Reactions are stopped by adding 50 μls of 500 mM sodium bicarbonate and analyzed by OD at 415 nm using a BioRad plate reader. Clones exhibiting an enhanced signal over background cells (H36 control cells) are then isolated and expanded into 10 ml cultures for additional characterization and confirmation of ELISA data in triplicate experiments. ELISAs are also performed on conditioned (CM) from the same clones to measure total Ig production within the conditioned medium of each well. Clones that produce an increased ELISA signal and have increased antibody levels are then further analyzed for variants that over-express and/or over-secrete antibodies as described in Example 4. Analysis of five 96-well plates each from HBvec or HB134 cells have found that a significant number of clones with a higher Optical Density (OD) value is observed in the MMR-defective HB134 cells as compared to the HBvec controls. FIG. 4 shows a representative example of HB134 clones producing antibodies that bind to specific antigen (in this case IgE) with a higher affinity. FIG. 4 provides raw data from the analysis of 96 wells of HBvec (left graph) or HB134 (right graph) which shows 2 clones from the HB134 plate to have a higher OD reading due to 1) genetic alteration of the antibody variable domain that leads to an increased binding to IgE antigen, or 2) genetic alteration of a cell host that leads to over-production/secretion of the antibody molecule. Anti-Ig ELISA found that the two clones, shown in FIG. 4 have Ig levels within their CM similar to the surrounding wells exhibiting ower OD values. These data suggest that a genetic alteration occurred within the antigen binding domain of the antibody which in turn allows for higher binding to antigen.

Clones that produced higher OD values as determined by ELISA were further analyzed at the genetic level to confirm that mutations within the light or heavy chain variable region have occurred that lead to a higher binding affinity hence yielding to a stronger ELISA signal. Briefly, 100,000 cells are harvested and extracted for RNA using the Triazol method as described above. RNAs are reverse transcribed using Superscript I as suggested by the manufacturer (Life Technology) and PCR amplified for the antigen binding sites contained within the variable light and heavy chains. Because of the heterogeneous nature of these genes, the following degenerate primers are used to amplify light and heavy chain alleles from the parent H36 strain.

Light chain sense: 5'-GGA TTT TCA GGT GCA GAT TTT CAG-3' (SEQ ID NO:1)

Light chain antisense: 5'-ACT GGA TGG TGG GAA GAT GGA-3'(SEQ ID NO:2)

Heavy chain sense: 5'-A(G/T) GTN (A/C)AG CTN CAG (C/G)AG TC-3' (SEQ ID NO:3)

Heavy chain antisense: 5'-TNC CTT G(A/G)C CCC AGT A(G/A)(A/T)C-3' (SEQ ID NO:4)

PCR reactions using degenerate oligonucleotides are carried out at 94° C. for 30 sec, 52° C. for 1 min, and 72° C. for 1 min for 35 cycles. Products are analyzed on agarose gels. Products of the expected molecular weights are purified from the gels by Gene Clean (Bio 101), cloned into T-tailed vectors, and sequenced to identify the wild type sequence of the variable light and heavy chains. Once the wild type sequence has been determined, non-degenerate primers were made for RT-PCR amplification of positive HB134 clones. Both the light and heavy chains were amplified, gel purified and sequenced using the corresponding sense and antisense primers. The sequencing of RT-PCR products gives representative sequence data of the endogenous immunoglobulin gene and not due to PCR induced mutations. Sequences from clones were then compared to the wild type sequence for sequence comparison. An example of the ability to create in vivo mutations within an immunoglobulin light or heavy chain is shown in FIG. 5, where HB134 clone 92 was identified by ELISA to have an increased signal for hIgE. The light chain was amplified using specific sense and antisense primers. The light chain was RTPCR amplified and the resulting product was purified and analyzed on an automated ABI377 sequencer. As shown in clone A, a residue-4 upstream of the CDR region 3 had a genetic change from ACT to TCT, which results in a Thr to Ser change within the framework region just preceding the CDR#3. In clone B, a residue-6 upstream of the CDR region had a genetic change from CCC to CTC, which results in a Pro to Leu change within framework region preceding CDR#2.

The ability to generate random mutations in immunoglobulin genes or chimeric immunoglobulin genes is not limited to hybridomas. Nicolaides et al. (Nicolaides et al. (1998) A Naturally Occurring hPMS2 Mutation Can Confer a Dominant Negative Mutator Phenotype *Mol. Cell. Biol.* 18:1635–1641) has previously shown the ability to generate hypermutable hamster cells and produce mutations within an endogenous gene. A common method for producing humanized antibodies is to graft CDR sequences from a MAb (produced by immunizing a rodent host) onto a human Ig backbone, and transfection of the chimeric genes into Chinese Hamster Ovary (CHO) cells whih in turn produce a functional Ab that is secreted by the CHO cells (Shields, R. L., et al. (1995) Anti-IgE monoclonal antibodies that inhibit allergen-specific histamine release. *Int. Arch. Allergy Immunol.* 107:412–413). The methods described within this application are also useful for generating genetic alterations within Ig genes or chimeric Igs transfected within host cells such as rodent cell lines, plants, yeast and prokaryotes (Frigerio L, et al. (2000) Assembly, secretion, and vacuolar delivery of a hybrid immunoglobulin in plants. *Plant Physiol.* 123:1483–1494).

These data demonstrate the ability to generate hypermutable hybridomas, or other Ig producing host cells that can be grown and selected, to identify structurally altered immunoglobulins yielding antibodies with enhanced biochemical properties, including but not limited to increased antigen binding affinity. Moreover, hypermutable clones that contain missense mutations within the immunoglobulin gene that result in an amino acid change or changes can be then further characterized for in vivo stability, antigen clearance, on-off binding to antigens, etc. Clones can also be further expanded for subsequent rounds of in vivo mutations and can be screened using the strategy listed above.

The use of chemical mutagens to produce genetic mutations in cells or whole organisms are limited due to the toxic effects that these agents have on “normal” cells. The use of chemical mutagens such as MNU in MMR defective organisms is much more tolerable yielding to a 10 to 100 fold increase in genetic mutation over MMR deficiency alone (Bignami M, (2000) Unmasking a killer: DNA O(6)-methylguanine and the cytotoxicity of methylating agents. *Mutat. Res.* 462:71–82). This strategy allows for the use of chemical mutagens to be used in MMR-defective Ab producing cells as a method for increasing additional mutations within immunoglobulin genes or chimeras that may yield functional Abs with altered biochemical properties such as enhanced binding affinity to antigen, etc.

EXAMPLE 4

Generation of Antibody Producing Cells with Enhanced Antibody Production

Analysis of clones from H36 and HB134 following the screening strategy listed above has identified a significant number of clones that produce enhanced amounts of antibody into the medium. While a subset of these clones gave higher Ig binding data as determined by ELISA as a consequence of mutations within the antigen binding domains contained in the variable regions, others were found to contain “enhanced” antibody production. A summary of the clones producing enhanced amounts of secreted MAb is shown in TABLE 2, where a significant number of clones from HB134 cells were found to produce enhanced Ab production within the conditioned medium as compared to 1136 control cells.

TABLE 2. Generation of hybridoma cells producing high levels of antibody. HB134 clones were assayed by ELISA for elevated Ig levels. Analysis of 480 clones showed that a significant number of clones had elevated MAb product levels in their CM. Quantification showed that several of these clones produced greater than 500 ngs/ml of MAb due to either enhanced expression and/or secretion as compared to clones from the H36 cell line.

TABLE 2

Production of MAb in CM from H36 and HB134 clones.

| Cell Line | % clones > 400 ng/ml | % clones > 500 ng/ml |
|---|---|---|
| H36 | 1/480 = 0.2% | 0/480 = 0% |
| HB134 | 50/480 = 10% | 8/480 = 1.7% |

Figure 6:
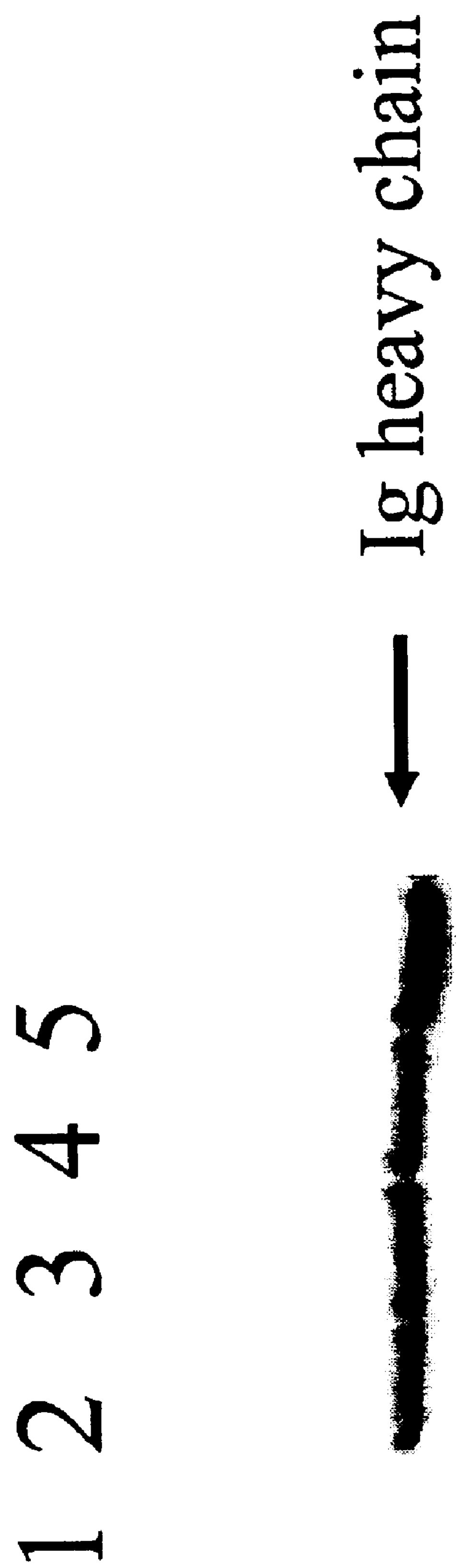
FIG. 6. Generation of MMR-defective clones with enhanced steady state Ig protein levels. A Western blot of heavy chain immunglobulins from HB 134 clones with high levels of MAb (>500 ngs/ml) within the conditioned medium shows that a subset of clones express higher steady state levels of immunoglobulins (Ig). The H36 cell line was used as a control to measure steady state levels in the parental strain. Lane 1: fibroblast cells (negative control)
Figure 2:
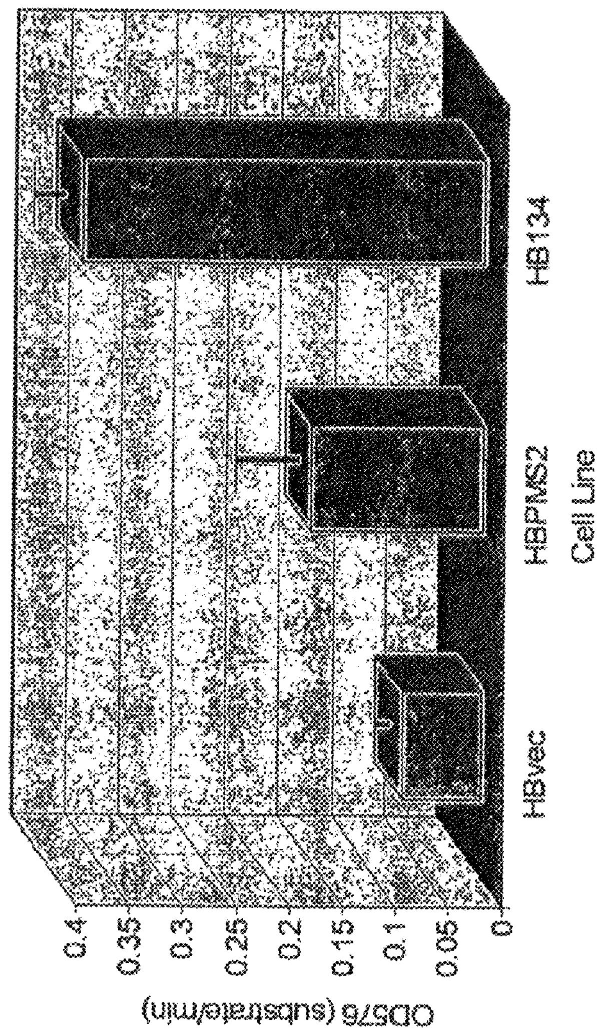
Figure 4:
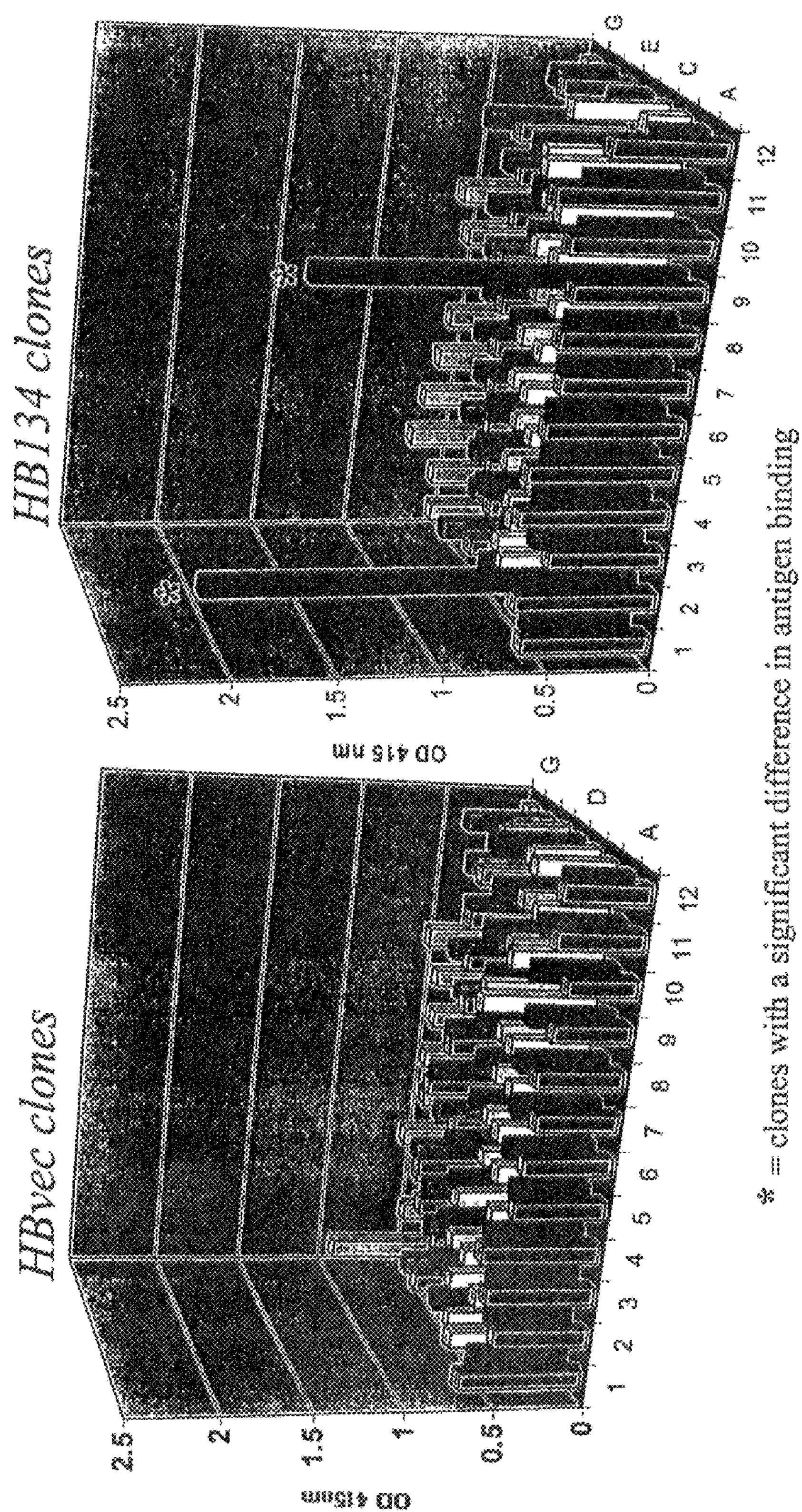

Cellular analysis of HB134 clones with higher MAb levels within the conditioned medium (CM) were analyzed to determine if the increased production was simply due to genetic alterations at the Ig locus that may lead to over-expression of the polypeptides forming the antibody, or due to enhanced secretion due to a genetic alteration affecting secretory pathway mechanisms. To address this issue, we expanded three HB134 clones that had increased levels of antibody within their CM. 10,000 cells were prepared for western blot analysis to assay for intracellular steady state Ig protein levels (FIG. 6). In addition, H36 cells were used as a standard reference (Lane 2) and a rodent fibroblast (Lane 1) was used as an Ig negative control. Briefly, cells were pelleted by centrifugation and lysed directly in 300 $\mu$l of SDS lysis buffer (60 mM Tris, pH 6.8, 2% SDS, 10% glycerol, 0.1 M 2-mercaptoethanol, 0.001% bromophenol blue) and boiled for 5 minutes. Lysate proteins were separated by electrophoresis on 4–12% NuPAGE gels (for analysis of Ig heavy chain. Gels were electroblotted onto Immobilon-P (Millipore) in 48 mM Tris base, 40 mM glycine, 0.0375% SDS, 20% methanol and blocked at room temperature for 1 hour in Tris-buffered saline (TBS) plus 0.05% Tween-20 and 5% condensed milk. Filters were probed with a 1:10,000 dilution of sheep anti-mouse horseradish peroxidase conjugated monoclonal antibody in TBS buffer and detected by chemiluminescence using Supersignal substrate (Pierce). Experiments were repeated in duplicates to ensure reproducibility. FIG. 6 shows a representative analysis where a subset of clones had enhanced Ig production which accounted for increased Ab production (Lane 5) while others had a similar steady state level as the control sample, yet had higher levels of Ab within the CM. These data suggest a mechanism whereby a subset of HB134 clones contained a genetic alteration that in turn produces elevated secretion of antibody.

The use of chemical mutagens to produce genetic mutations in cells or whole organisms are limited due to the toxic effects that these agents have on "normal" cells. The use of chemical mutagens such as MNU in MMR defective organisms is much more tolerable yielding to a 10 to 100 fold increase in genetic mutation over MMR deficiency alone (Bignami M, (2000) Unmasking a killer: DNA O(6)-methylguanine and the cytotoxicity of methylating agents. *Mutat. Res.* 462:71–82). This strategy allows for the use of chemical mutagens to be used in MMR-defective Ab producing cells as a method for increasing additional mutations within immunoglobulin genes or chimeras that may yield functional Abs with altered biochemical properties such as enhanced binding affinity to antigen, etc.

EXAMPLE 5

Establishment of Genetic Stability in Hybridoma Cells with New Output Trait

The initial steps of MMR are dependent on two protein complexes, called MutSα and MutLα (Nicolaides et al. (1998) A Naturally Occurring hPMS2 Mutation Can Confer a Dominant Negative Mutator Phenotype. *Mol. Cell. Biol.* 18:1635–1641). Dominant negative MMR alleles are able to perturb the formation of these complexes with downstream biochemicals involved in the excision and polymerization of nucleotides comprising the "corrected" nucleotides. Examples from this application show the ability of a truncated MMR allele (PMS134) as well as a full length human PMS2 when expressed in a hybridoma cell line is capable of blocking MMR resulting in a hypermutable cell line that gains genetic alterations throughout its entire genome per cell division. Once a cell line is produced that contains genetic alterations within genes encoding for an antibody, a single chain antibody, over expression of immunoglobulin genes and/or enhanced secretion of antibody, it is desirable to restore the genomic integrity of the cell host. This can be achieved by the use of inducible vectors whereby dominant negative MMR genes are cloned into such vectors, introduced into Ab producing cells and the cells are cultured in the presence of inducer molecules and/or conditions. Inducible vectors include but are not limited to chemical regulated promoters such as the steroid inducible MMTV, tetracycline regulated promoters, temperature sensitive MMR gene alleles, and temperature sensitive promoters.

The results described above lead to several conclusions. First, expression of hPMS2 and PMS134 results in an increase in microsatellite instability in hybridoma cells. That this elevated microsatellite instability is due to MMR deficiency was proven by evaluation of extracts from stably transduced cells. The expression of PMS134 results in a polar defect in MMR, which was only observed using heteroduplexes designed to test repair from the 5'direction (no significant defect in repair from the 3' direction was observed in the same extracts) (Nicolaides et al. (1998) A Naturally Occurring hPMS2 Mutation Can Confer a Dominant Negative Mutator Phenotype. *Mol. Cell. Biol.* 18:1635–1641). Interestingly, cells deficient in hMLH1 also have a polar defect in MMR, but in this case preferentially affecting repair from the 3' direction (Drummond, J. T, et al. (1996) Cisplatin and adriamycin resistance are associated with MutLa and mismatch repair deficiency in an ovarian tumor cell line. *J Biol. Chem.* 271:9645–19648). It is known from previous studies in both prokaryotes and eukaryotes that the separate enzymatic components mediate repair from the two different directions. Our results, in combination with those of Drummond et al. (Shields, R. L., et al. (1995) Anti-IgE monoclonal antibodies that inhibit allergen-specific histamine release. *Int. Arch Allergy Immunol.* 107:412–413), strongly suggest a model in which 5' repair is primarily dependent on hPMS2 while 3' repair is primarily dependent on hMLH1. It is easy to envision how the dimeric complex between PMS2 and MLH1might set up this directionality. The combined results also demonstrate that a defect in directional MMR is sufficient to produce a MMR defective phenotype and suggests that any MMR gene allele is useful to produce genetically altered hybridoma cells, or a cell line that is producing Ig gene products. Moreover, the use of such MMR alleles will be useful for generating genetically altered Ig polypeptides with altered biochemical properties as well as cell hosts that produce enhanced amounts of antibody molecules.

Another method that is taught in this application is that ANY method used to block MMR can be performed to generate hypermutablility in an antibody-producing cell that can lead to genetically altered antibodies with enhanced biochemical features such as but not limited to increased antigen binding, enhanced pharmacokinetic profiles, etc.

These processes can also to be used to generate antibody producer cells that have increased Ig expression as shown in Example 4, FIG. 6 and/or increased antibody secretion as shown in Table 2.

Figure 5A:
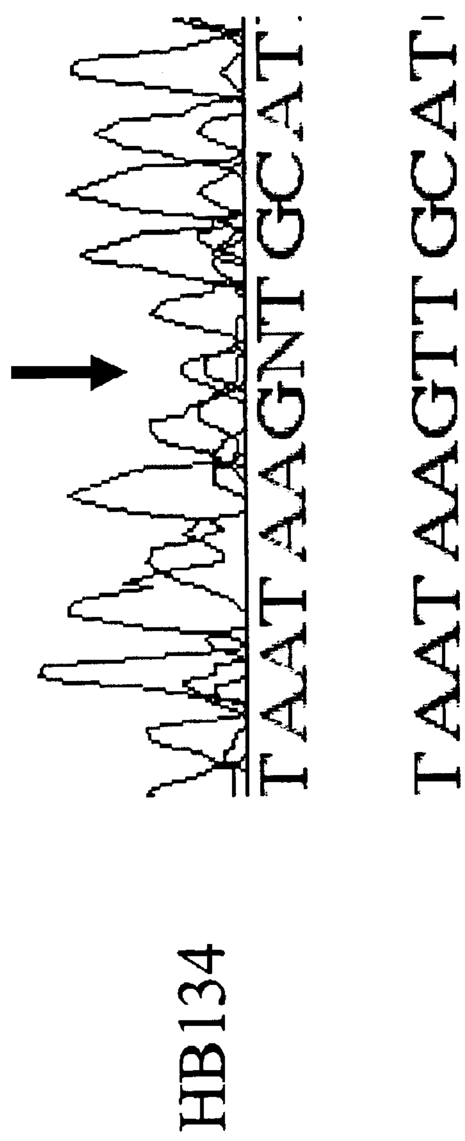
FIG. 5A. Sequence alteration within variable chain of an antibody (a mutation within the light chain variable region in MMR-defective HB134 antibody producer cells). Arrows indicate the nucleotide at which a mutation occurred in a subset of cells from a clone derived from HB134 cells. The HB134 sequence (SEQ ID NO:19) is shown as the top line and the parental H36 sequence (SEQ ID NO:20) is shown above and below the sequence tracing. The change results in a Thr to Ser change within the light chain variable region. The coding sequence is in the antisense direction.
Figure 5A:
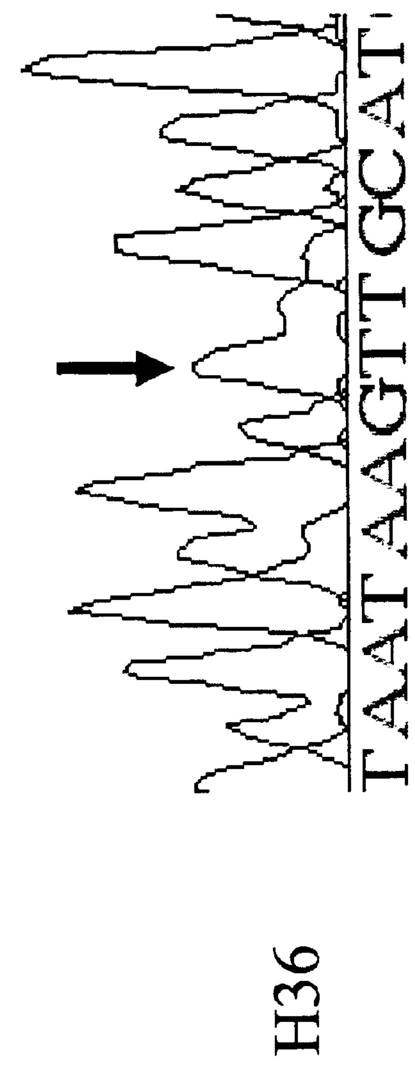
Figure 5B:
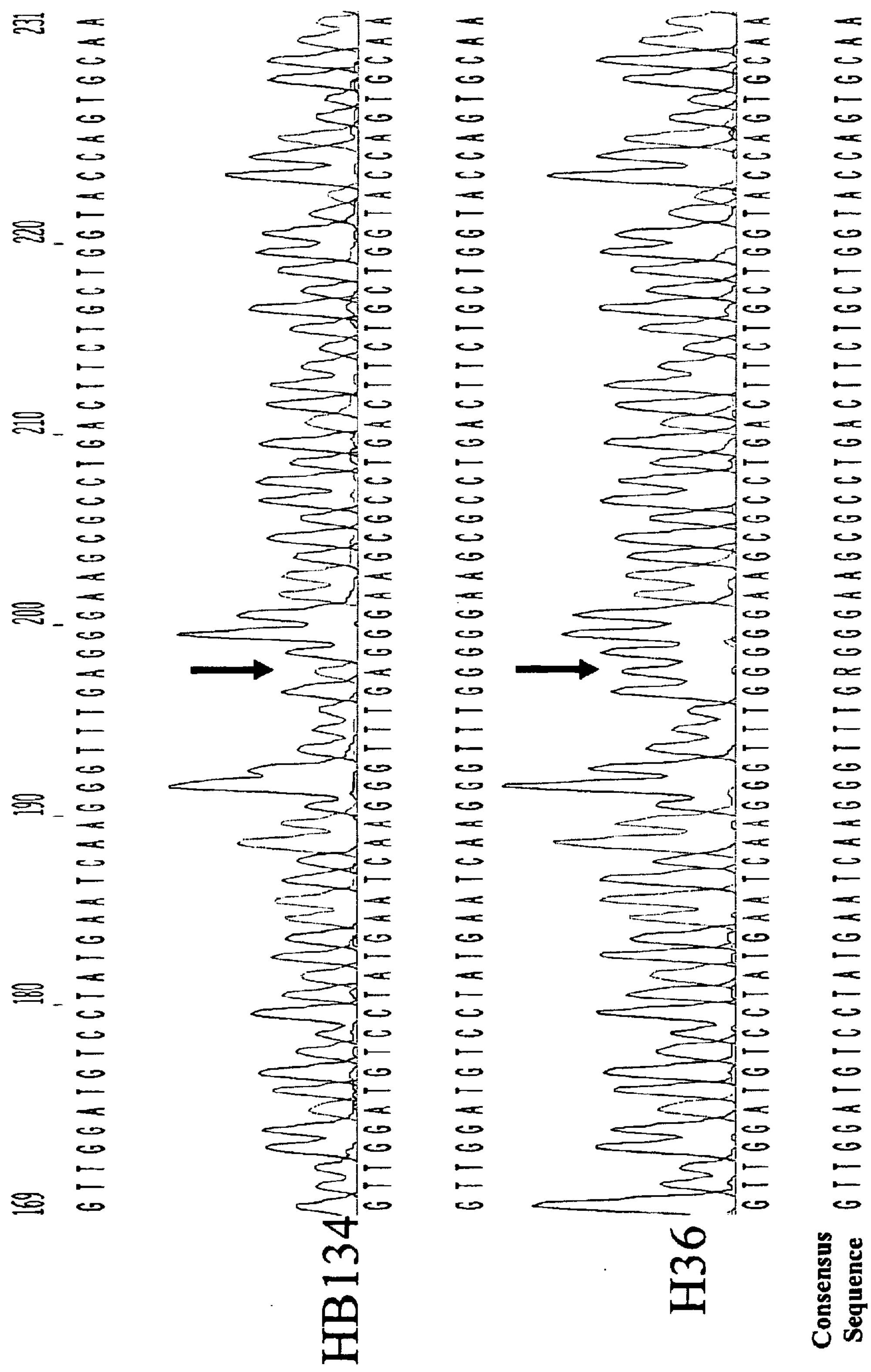
FIG. 5B. Sequence alteration within variable chain of an antibody (a mutation within the light chain variable region in MMR-defective HB134 antibody producer cells). The HB134 sequence (SEQ ID NO:21) is shown above and below the tracing for the HB134 sequence, and the parental H36 sequence (SEQ ID NO:22) is shown above and below the H36 sequence tracing. A consensus sequence (SEQ ID NO:23) is shown at the bottom of the figure. Arrows indicate the nucleotide at which a mutation occurred in a subset of cells from a clone derived from HB134 cells. The change results in a Pro to Leu change within the light chain variable region.

In addition, we demonstrate the utility of blocking MMR in antibody producing cells to increase genetic alterations within lg genes that may lead to altered biochemical features such as, but not limited to, increased antigen binding affinities (FIG. 5A and 5B). The blockade of MMR in such cells can be through the use of dominant negative MMR gene alleles from any species including bacteria, yeast, protozoa, insects, rodents, primates, mammalian cells, and man. Blockade of MMR can also be generated through the use of antisense RNA or deoxynucleotides directed to any of the genes involved in the MMR biochemical pathway. Blockade of MMR can be through the use of polypeptides that interfere with subunits of the MMR complex including but not limited to antibodies. Finally, the blockade of MMR may be through the use chemicals such as but not limited to nonhydrolyzable ATP analogs, which have been shown to block MMR (Galio, L, et al. (1999) ATP hydrolysis-dependent formation of a dynamic ternary nucleoprotein complex with MutS and MutL. *Nucl. Acids Res.* 27:2325–23231).

We claim:

1. A method for making a hypermutable, antibody-producing cell in vitro, comprising introducing into a cell that produces antibodies a polynucleotide comprising a dominant negative allele of a mismatch repair gene, wherein said dominant negative allele is a truncation mutant of a PMS2, wherein said antibody-producing cell becomes hypermutable.

2. The method of claim 1 wherein said polynucleotide is introduced by transfection of a suspension of cells in vitro.

3. The method of claim 1 wherein said mismatch repair gene is human PMS2.

4. The method of claim 1 wherein said allele comprises a truncation mutation at codon 134.

5. The method of claim 4 wherein said truncation mutation is a thymidine at nucleotide 424 of wild-type PMS2.

6. The method of claim 1 wherein an immunoglobulin gene is co-introduced into said cell, whereby said cell produces said antibodies.

7. A homogeneous culture of isolated, hypermutable, mammalian cells wherein said cells produce antibodies and comprise a dominant negative allele of a mismatch repair gene, wherein said dominant negative allele encodes a truncation mutant of a PMS2 protein.

8. The culture of isolated, hypermutable, mammalian cells of claim 7 wherein the mismatch repair gene is human PMS2.

9. The culture of isolated, hypermutable, mammalian cells of claim 7 wherein the cells express a protein consisting of the first 133 amino acids of hPMS2.

10. An isolated, hypermutable, antibody-producing cell produced by the method of claim 1.

11. An isolated, hypermutable, antibody-producing cell produced by the method of claim 3.

12. The method of claim 1 further comprising the step restoring genetic stability of said hypermutable cell.

13. An isolated, genetically stable, mutated antibody-producing cell produced by the method of claim 12, wherein said isolated, genetically stable, mutated antibody-producing cell produces an antibody having increased affinity for antigen relative to said antibody-producing cell prior to introduction of said dominant negative allele of said mismatch repair gene, wherein said dominant negative allele of said PMS2 mismatch repair gene of said polynucleotide is inactivated.

14. A homogeneous culture of the isolated, genetically stable, antibody-producing cells of claim 13.

15. The method of claim 6 further comprising the step restoring genetic stability of said hypermutable cell.

16. An isolated, genetically stable, mutated antibody-producing cell produced by the method of claim 15, wherein said isolated, genetically stable, mutated antibody-producing cell produces an antibody having increased affinity for antigen relative to said antibody-producing cell prior to introduction of said dominant negative allele of said mismatch repair gene, wherein said dominant negative allele of said PMS2 mismatch repair gene of said polynucleotide is inactivated.

17. A homogeneous culture of the isolated, genetically stable, mutated antibody-producing cells of claim 16.

18. An isolated, genetically stable, mutated antibody-producing cell produced by the method of claim 12, wherein said isolated, genetically stable, mutated antibody-producing cell produces an increased titer of antibody relative to said antibody-producing cell prior to introduction of said dominant negative allele of said mismatch repair gene, wherein said dominant negative allele of said PMS2 mismatch repair gene of said polynucleotide is inactivated.

19. A homogeneous culture of the isolated, genetically stable, mutated antibody-producing cells of claim 18.

20. An isolated, genetically stable, mutated antibody-producing cell produced by the method of claim 15, wherein said isolated, genetically stable, mutated antibody-producing cell produces an increased titer of antibody relative to said antibody-producing cell prior to introduction of said dominant negative allele of said mismatch repair gene, wherein said dominant negative allele of said PMS2 mismatch repair gene of said polynucleotide is inactivated.

21. A homogeneous culture of the isolated, genetically stable, mutated antibody-producing cells of claim 20.

* * * * *

UNITED STATES PATENT AND TRADEMARK OFFICE

CERTIFICATE OF CORRECTION

PATENT NO. : 6,808,894 B1
APPLICATION NO. : 09/707468
DATED : October 26, 2004
INVENTOR(S) : Nicholas C. Nicolaides, Luigi Grasso and Philip M. Sass It is certified that error appears in the above-identified patent and that said Letters Patent is hereby corrected as shown below:

Item (56), References Cited, OTHER PUBLICATIONS:
"Yu, Y. et al.," reference, please delete "induccs" and insert -- induces -- therefor.
"Hoang J., et al.," reference, please delete "Lnes"," and insert -- Lines", -- therefor.
"Khazaeli, M.B. et al.," reference, please delete ""Huamn" and insert -- "Human -- therefor.
"Nicolaides, N.C., "A naturally occurring hPMS2 mutation..." reference, please delete "nutator" and insert -- mutator -- therefor.
Item (56), References Cited, OTHER PUBLICATIONS:
"Su, S., et al.," reference, please delete "J. Biologicl Chemistyr," and insert -- J. Biological Chemistry, -- therefor.
"Vora, K.A. et al.," reference, please delete "Medicien," and insert -- Medicine, -- therefor.
"Wheeler, J.M.D., et al.," reference, please delete "J. Med. Gent.," and insert -- J. Med. Genet., -- therefor.

In the Drawings,
Delete drawing sheets 2 of 7 and 4 of 7, substitute replacement sheets for Figures 2 and 4 are attached to better show the clarity and detail.

Column 3,
Line 13, please delete "hut" and insert -- but -- therefor.
Line 50, please delete "MSH2," therefor.
Line 60, please delete "MSH2," therefor.

Column 4,
Line 63, please delete "polyeptides" and insert -- polypeptides -- therefor.

Column 6,
Line 25, please delete "galactosidase" and insert -- β-galactosidase -- therefor.
Line 31, after "expression/secretion", please insert -- . -- therefor.

Column 8,
Line 4, please delete "can he" and insert -- can be -- therefor.
Line 10, after "itself", please insert -- . -- therefor.

Column 27,
Line 39, please delete "5,530,101to" and insert -- 5,530,101 to -- therefor.
Line 59, please delete "82:321-300." and insert -- 82:321-330. -- therefor.

UNITED STATES PATENT AND TRADEMARK OFFICE

CERTIFICATE OF CORRECTION

PATENT NO. : 6,808,894 B1
APPLICATION NO. : 09/707468
DATED : October 26, 2004
INVENTOR(S) : Nicholas C. Nicolaides, Luigi Grasso and Philip M. Sass It is certified that error appears in the above-identified patent and that said Letters Patent is hereby corrected as shown below:

Column 28,
Line 28, please delete "RER" and insert -- $RER^+$ -- therefor.
Line 58, please delete "0(6)-" and insert -- O(6)- -- therefor.
Line 65, please delete "Galio. L. et al." and insert -- Galio, L. et al. -- therefor.
Line 67, please delete "27:2325-23231." and insert -- 27:2325-2331. -- therefor.

Column 29,
Line 36, please delete "and" and insert -- an -- therefor.
Line 61, please delete "PEF" and insert -- pEF -- therefor.
Line 63, please delete "2." and insert -- 2, -- therefor.

Column 30,
Line 1, please delete "Kinzler." and insert -- Kinzler, -- therefor.
Line 12, please delete "(Nicolaides." and insert -- (Nicolaides, -- therefor.
Line 14, please delete "tile" and insert -- the -- therefor.

Column 31,
Line 47, please delete "1 nM" and insert -- 1 mM -- therefor.

Column 32,
Line 45, please delete "$PBS^{- -}$" and insert -- $PBS^{-/-}$ -- therefor.
Line 48, please delete "$PBS^{- -}$" and insert -- $PBS^{-/-}$ -- therefor.

Column 33,
Line 11, please delete "ower" and insert -- lower -- therefor.
Line 22, please delete "Superscript I" and insert -- Superscript II -- therefor.
Line 57, please delete "RTPCR" and insert -- RT-PCR -- therefor.
Line 62, please delete "residue-6" and insert -- residue -6 -- therefor.

Column 34,
Line 10, please delete "whih" and insert -- which -- therefor.
Line 64, please delete "1136" and insert -- H36 -- therefor.

Column 36,
Line 32, please delete "5'direction" and insert -- 5' direction -- therefor.
Line 42, please delete "271:9645-19648)." and insert -- 271:19645-19648). -- therefor.
Line 52, please delete "MLH1might" and insert -- MLH1 might -- therefor.

UNITED STATES PATENT AND TRADEMARK OFFICE

CERTIFICATE OF CORRECTION

PATENT NO. : 6,808,894 B1
APPLICATION NO. : 09/707468
DATED : October 26, 2004
INVENTOR(S) : Nicholas C. Nicolaides, Luigi Grasso and Philip M. Sass It is certified that error appears in the above-identified patent and that said Letters Patent is hereby corrected as shown below:

Column 38,
Line 12, please delete "27:2325-23231)." and insert -- 27:2325-2331). -- therefor.

Signed and Sealed this

Ninth Day of December, 2008

JON W. DUDAS
*Director of the United States Patent and Trademark Office*

UNITED STATES PATENT AND TRADEMARK OFFICE

CERTIFICATE OF CORRECTION

PATENT NO. : 6,808,894 B1 
APPLICATION NO. : 09/707468
DATED : October 26, 2004
INVENTOR(S) : Nicholas C. Nicolaides, Luigi Grasso and Philip M. Sass It is certified that error appears in the above-identified patent and that said Letters Patent is hereby corrected as shown below:

Title Page,
Item (56), References Cited, U.S. PATENT DOCUMENTS, please insert the following reference:
-- 5,885,827 3/1999 Wabl et al. 435/320.1 --.

OTHER PUBLICATIONS, please insert the following references:
-- Allen, D., et al., "MutS mediates heteroduplex loop formation by a translocation mechanism," EMBO J., 1997, 16(14), 4467-4476.
Baker, S.M., et al., "Male mice defective in the DNA mismatch repair gene PMS2 exhibit abnormal chromosome synapsis in meiosis," Cell, 1995, 82, 309-319.
Bell, C.J. et al., "Assignment of 30 microsatellite loci to the linkage map of arabidopsis,"
Genomics, 1994, 19, 137-144.
Bignami M., "Unmasking a Killer: DNA $O^6$-methylguanine and the Cytotoxicity of Methylating Agents", Mutat. Res., 2000, 462, 71-82.
Bjornson, K., et al., "Modulation of MutS ATP hydrolysis by DNA cofactors," Biochemistry, 2000, 39, 3176-3183.
Bronner, C.E., et al., "Mutation in the DNA mismatch repair gene homologue hMLH1 is associated with hereditary non-polyposis colon cancer," Nature, 1994, 368, 258-261.
de Wind, N., et al., "Inactivation of the mouse Msh2 gene results in mismatch repair deficiency, methylation tolerance, hyperrecombination, and predisposition to cancer," Cell, 1995, 82, 321-330.
Drummond, J.T., et al., "Isolation of an hMSH2-p160 heterodimer that restores DNA mismatch repair to tumor cells," Science, 1995, 268, 1909-1912.
Drummond, J.T. et al., "Cisplatin and adriamycin resistance are associated with mutLα and mismatch repair deficiency in an ovarian tumor cell line," J. Biological Chemistry, 1996, 271(33), 19645-19648. --.

UNITED STATES PATENT AND TRADEMARK OFFICE

CERTIFICATE OF CORRECTION

PATENT NO. : 6,808,894 B1
APPLICATION NO. : 09/707468
DATED : October 26, 2004
INVENTOR(S) : Nicholas C. Nicolaides, Luigi Grasso and Philip M. Sass It is certified that error appears in the above-identified patent and that said Letters Patent is hereby corrected as shown below:

Title Page,
Item (56), References Cited, OTHER PUBLICATIONS, please insert the following references:
-- Edelmann, W., et al., "Meiotic pachytene arrest in MLH1-deficient mice," Cell, 1996, 85, 1125-1134.
Emery, S.C. and Harris, W.J., "Strategies for Humanizing Antibodies" In C.A.K. Borrebaeck (Ed.) ANTIBODY ENGINEERING. Oxford University Press, N.Y. 1995; pp. 159-183.
Eshleman, J.R., et al., "Mismatch repair defects in human carcinogenesis," Human Molecular Genetics, 1996, 5, 1489-1494.
Rulicke et al., Special review series-gene manipulation and integrative physiology, pp. 589-600, 1996.
Bishop Chromosomal insertion of foreign DNA, pp. 607-619, 1996.
Polejaeva et al., New advances in somatic cell nuclear transfer application in transgenesis, pp. 117-126, 2000.
Anderson, Human gene therapy, pp. 25-30, 1998. --.

Item (56), References Cited, OTHER PUBLICATIONS:
"Yu, Y. et al.," reference, please delete "induccs" and insert -- induces -- therefor.
"Hoang J., et al.," reference, please delete "Lnes"," and insert -- Lines", -- therefor.
"Khazaeli, M.B. et al.," reference, please delete ""Huamn" and insert -- "Human -- therefor.
"Nicolaides, N.C., "A naturally occurring hPMS2 mutation..." reference, please delete "nutator" and insert -- mutator -- therefor.

Signed and Sealed this

Second Day of June, 2009

JOHN DOLL
*Acting Director of the United States Patent and Trademark Office*

```
                    SEQUENCE LISTING

<160> NUMBER OF SEQ ID NOS: 23

<210> SEQ ID NO 1
<211> LENGTH: 24
<212> TYPE: DNA
<213> ORGANISM: Artificial Sequence
<220> FEATURE:
<223> OTHER INFORMATION: Oligonucleotide primer

<400> SEQUENCE: 1

ggattttcag gtgcagattt tcag                                            24


<210> SEQ ID NO 2
<211> LENGTH: 21
<212> TYPE: DNA
<213> ORGANISM: Artificial Sequence
<220> FEATURE:
<223> OTHER INFORMATION: Oligonucleotide primer

<400> SEQUENCE: 2

actggatggt gggaagatgg a                                               21


<210> SEQ ID NO 3
<211> LENGTH: 19
<212> TYPE: DNA
<213> ORGANISM: Artificial Sequence
<220> FEATURE:
<223> OTHER INFORMATION: Oligonucleotide primer
<220> FEATURE:
<221> NAME/KEY: misc_feature
<222> LOCATION: (5)..(5)
<223> OTHER INFORMATION: A or G or C or T/U
<220> FEATURE:
<221> NAME/KEY: misc_feature
<222> LOCATION: (11)..(11)
<223> OTHER INFORMATION: A or G or C or T/U

<400> SEQUENCE: 3

akgtnmagct ncagsagtc                                                  19


<210> SEQ ID NO 4
<211> LENGTH: 19
<212> TYPE: DNA
<213> ORGANISM: Artificial Sequence
<220> FEATURE:
<223> OTHER INFORMATION: Oligonucleotide primer
<220> FEATURE:
<221> NAME/KEY: misc_feature
<222> LOCATION: (2)..(2)
<223> OTHER INFORMATION: A or G or C or T/U

<400> SEQUENCE: 4

tnccttgrcc ccagtarwc                                                  19
```

<210> SEQ ID NO 5
<211> LENGTH: 859
<212> TYPE: PRT
<213> ORGANISM: Mus musculus

<400> SEQUENCE: 5

```
Met Glu Gln Thr Glu Gly Val Ser Thr Glu Cys Ala Lys Ala Ile Lys
1               5                   10                  15

Pro Ile Asp Gly Lys Ser Val His Gln Ile Cys Ser Gly Gln Val Ile
            20                  25                  30

Leu Ser Leu Ser Thr Ala Val Lys Glu Leu Ile Glu Asn Ser Val Asp
        35                  40                  45

Ala Gly Ala Thr Thr Ile Asp Leu Arg Leu Lys Asp Tyr Gly Val Asp
    50                  55                  60

Leu Ile Glu Val Ser Asp Asn Gly Cys Gly Val Glu Glu Glu Asn Phe
65                  70                  75                  80

Glu Gly Leu Ala Leu Lys His His Thr Ser Lys Ile Gln Glu Phe Ala
                85                  90                  95

Asp Leu Thr Gln Val Glu Thr Phe Gly Phe Arg Gly Glu Ala Leu Ser
            100                 105                 110

Ser Leu Cys Ala Leu Ser Asp Val Thr Ile Ser Thr Cys His Gly Ser
        115                 120                 125

Ala Ser Val Gly Thr Arg Leu Val Phe Asp His Asn Gly Lys Ile Thr
    130                 135                 140

Gln Lys Thr Pro Tyr Pro Arg Pro Lys Gly Thr Thr Val Ser Val Gln
145                 150                 155                 160

His Leu Phe Tyr Thr Leu Pro Val Arg Tyr Lys Glu Phe Gln Arg Asn
                165                 170                 175

Ile Lys Lys Glu Tyr Ser Lys Met Val Gln Val Leu Gln Ala Tyr Cys
            180                 185                 190

Ile Ile Ser Ala Gly Val Arg Val Ser Cys Thr Asn Gln Leu Gly Gln
        195                 200                 205

Gly Lys Arg His Ala Val Val Cys Thr Ser Gly Thr Ser Gly Met Lys
    210                 215                 220

Glu Asn Ile Gly Ser Val Phe Gly Gln Lys Gln Leu Gln Ser Leu Ile
225                 230                 235                 240

Pro Phe Val Gln Leu Pro Pro Ser Asp Ala Val Cys Glu Glu Tyr Gly
                245                 250                 255

Leu Ser Thr Ser Gly Arg His Lys Thr Phe Ser Thr Phe Arg Ala Ser
            260                 265                 270

Phe His Ser Ala Arg Thr Ala Pro Gly Gly Val Gln Gln Thr Gly Ser
        275                 280                 285

Phe Ser Ser Ser Ile Arg Gly Pro Val Thr Gln Gln Arg Ser Leu Ser
    290                 295                 300

Leu Ser Met Arg Phe Tyr His Met Tyr Asn Arg His Gln Tyr Pro Phe
305                 310                 315                 320

Val Val Leu Asn Val Ser Val Asp Ser Glu Cys Val Asp Ile Asp Val
                325                 330                 335

Thr Pro Asp Lys Arg Gln Ile Leu Leu Gln Glu Glu Lys Leu Leu Leu
            340                 345                 350

Ala Val Leu Lys Thr Ser Leu Ile Gly Met Phe Asp Ser Asp Ala Asn
        355                 360                 365

Lys Leu Asn Val Asn Gln Gln Pro Leu Leu Asp Val Glu Gly Asn Leu
```

-continued

```
    370                 375                 380

Val Lys Leu His Thr Ala Glu Leu Glu Lys Pro Val Pro Gly Lys Gln
385                 390                 395                 400

Asp Asn Ser Pro Ser Leu Lys Ser Thr Ala Asp Glu Lys Arg Val Ala
                405                 410                 415

Ser Ile Ser Arg Leu Arg Glu Ala Phe Ser Leu His Pro Thr Lys Glu
            420                 425                 430

Ile Lys Ser Arg Gly Pro Glu Thr Ala Glu Leu Thr Arg Ser Phe Pro
        435                 440                 445

Ser Glu Lys Arg Gly Val Leu Ser Ser Tyr Pro Ser Asp Val Ile Asp
    450                 455                 460

Tyr Arg Gly Leu Arg Gly Ser Gln Asp Lys Leu Val Ser Pro Thr Asp
465                 470                 475                 480

Ser Pro Gly Asp Cys Met Asp Arg Glu Lys Ile Glu Lys Asp Ser Gly
                485                 490                 495

Leu Ser Ser Thr Ser Ala Gly Ser Glu Glu Phe Ser Thr Pro Glu
            500                 505                 510

Val Ala Ser Ser Phe Ser Ser Asp Tyr Asn Val Ser Ser Leu Glu Asp
        515                 520                 525

Arg Pro Ser Gln Glu Thr Ile Asn Cys Gly Asp Leu Asp Cys Arg Pro
    530                 535                 540

Pro Gly Thr Gly Gln Ser Leu Lys Pro Glu Asp His Gly Tyr Gln Cys
545                 550                 555                 560

Lys Ala Leu Pro Leu Ala Arg Leu Ser Pro Thr Asn Ala Lys Arg Phe
                565                 570                 575

Lys Thr Glu Glu Arg Pro Ser Asn Val Asn Ile Ser Gln Arg Leu Pro
            580                 585                 590

Gly Pro Gln Ser Thr Ser Ala Ala Glu Val Asp Val Ala Ile Lys Met
        595                 600                 605

Arg Met Lys Gln Leu Gln His Leu Lys Ala Gln Asn Lys His Glu Leu
    610                 615                 620

Arg Met Lys Gln Leu Gln His Leu Lys Ala Gln Asn Lys His Glu Leu
625                 630                 635                 640

Ser Tyr Arg Lys Phe Arg Ala Lys Ile Cys Pro Gly Glu Asn Gln Ala
                645                 650                 655

Ala Glu Asp Glu Leu Arg Lys Glu Ile Ser Lys Ser Met Phe Ala Glu
            660                 665                 670

Met Glu Ile Leu Gly Gln Phe Asn Leu Gly Phe Ile Val Thr Lys Leu
        675                 680                 685

Lys Glu Asp Leu Phe Leu Val Asp Gln His Ala Ala Asp Glu Lys Tyr
    690                 695                 700

Asn Phe Glu Met Leu Gln Gln His Thr Val Leu Gln Ala Gln Arg Leu
705                 710                 715                 720

Ile Thr Pro Gln Thr Leu Asn Leu Thr Ala Val Asn Glu Ala Val Leu
                725                 730                 735

Ile Glu Asn Leu Glu Ile Phe Arg Lys Asn Gly Phe Asp Phe Val Ile
            740                 745                 750

Asp Glu Asp Ala Pro Val Thr Glu Arg Ala Lys Leu Ile Ser Leu Pro
        755                 760                 765

Thr Ser Lys Asn Trp Thr Phe Gly Pro Gln Asp Ile Asp Glu Leu Ile
    770                 775                 780

Phe Met Leu Ser Asp Ser Pro Gly Val Met Cys Arg Pro Ser Arg Val
785                 790                 795                 800
```

```
Arg Gln Met Phe Ala Ser Arg Ala Cys Arg Lys Ser Val Met Ile Gly
                805                 810                 815

Thr Ala Leu Asn Ala Ser Glu Met Lys Lys Leu Ile Thr His Met Gly
            820                 825                 830

Glu Met Asp His Pro Trp Asn Cys Pro His Gly Arg Pro Thr Met Arg
        835                 840                 845

His Val Ala Asn Leu Asp Val Ile Ser Gln Asn
    850                 855


<210> SEQ ID NO 6
<211> LENGTH: 3056
<212> TYPE: DNA
<213> ORGANISM: Mus musculus

<400> SEQUENCE: 6

gaattccggt gaaggtcctg aagaatttcc agattcctga gtatcattgg aggagacaga     60

taacctgtcg tcaggtaacg atggtgtata tgcaacagaa atgggtgttc ctggagacgc    120

gtcttttccc gagagcggca ccgcaactct cccgcggtga ctgtgactgg aggagtcctg    180

catccatgga gcaaaccgaa ggcgtgagta cagaatgtgc taaggccatc aagcctattg    240

atgggaagtc agtccatcaa atttgttctg ggcaggtgat actcagttta agcaccgctg    300

tgaaggagtt gatagaaaat agtgtagatg ctggtgctac tactattgat ctaaggctta    360

aagactatgg ggtggacctc attgaagttt cagacaatgg atgtggggta gaagaagaaa    420

actttgaagg tctagctctg aaacatcaca catctaagat tcaagagttt gccgacctca    480

cgcaggttga aactttcggc tttcgggggg aagctctgag ctctctgtgt gcactaagtg    540

atgtcactat atctacctgc cacgggtctg caagcgttgg gactcgactg gtgtttgacc    600

ataatgggaa aatcacccag aaaactccct acccccgacc taaaggaacc acagtcagtg    660

tgcagcactt attttataca ctacccgtgc gttacaaaga gtttcagagg aacattaaaa    720

aggagtattc caaaatggtg caggtcttac aggcgtactg tatcatctca gcaggcgtcc    780

gtgtaagctg cactaatcag ctcggacagg ggaagcggca cgctgtggtg tgcacaagcg    840

gcacgtctgg catgaaggaa aatatcgggt ctgtgtttgg ccagaagcag ttgcaaagcc    900

tcattccttt tgttcagctg ccccctagtg acgctgtgtg tgaagagtac ggcctgagca    960

cttcaggacg ccacaaaacc ttttctacgt ttcgggcttc atttcacagt gcacgcacgg   1020

cgccgggagg agtgcaacag acaggcagtt tttcttcatc aatcagaggc cctgtgaccc   1080

agcaaaggtc tctaagcttg tcaatgaggt tttatcacat gtataaccgg catcagtacc   1140

catttgtcgt ccttaacgtt tccgttgact cagaatgtgt ggatattaat gtaactccag   1200

ataaaaggca aattctacta caagaagaga agctattgct ggccgtttta aagacctcct   1260

tgataggaat gtttgacagt gatgcaaaca agcttaatgt caaccagcag ccactgctag   1320

atgttgaagg taacttagta aagctgcata ctgcagaact agaaaagcct gtgccaggaa   1380

agcaagataa ctctccttca ctgaagagca cagcagacga gaaaagggta gcatccatct   1440

ccaggctgag agaggccttt tctcttcatc ctactaaaga gatcaagtct aggggtccag   1500

agactgctga actgacacgg agttttccaa gtgagaaaag gggcgtgtta tcctcttatc   1560

cttcagacgt catctcttac agaggcctcc gtggctcgca ggacaaattg gtgagtccca   1620

cggacagccc tggtgactgt atggacagag agaaaataga aaaagactca gggctcagca   1680

gcacctcagc tggctctgag gaagagttca gcaccccaga agtggccagt agctttagca   1740
```

-continued gtgactataa cgtgagctcc ctagaagaca gaccttctca ggaaaccata aactgtggtg 1800
acctggactg ccgtcctcca ggtacaggac agtccttgaa gccagaagac catggatatc 1860
aatgcaaagc tctacctcta gctcgtctgt cacccacaaa tgccaagcgc ttcaagacag 1920
aggaaagacc ctcaaatgtc aacatttctc aaagattgcc tggtcctcag agcacctcag 1980
cagctgaggt cgatgtagcc ataaaaatga ataagagaat cgtgctcctc gagttctctc 2040
tgagttctct agctaagcga atgaagcagt tacagcacct aaaggcgcag aacaaacatg 2100
aactgagtta cagaaaattt agggccaaga tttgccctgg agaaaaccaa gcagcagaag 2160
atgaactcag aaaagagatt agtaaatcga tgtttgcaga gatggagatc ttgggtcagt 2220
ttaacctggg atttatagta accaaactga aagaggacct cttcctggtg gaccagcatg 2280
ctgcggatga gaagtacaac tttgagatgc tgcagcagca cacggtgctc caggcgcaga 2340
ggctcatcac accccagact ctgaacttaa ctgctgtcaa tgaagctgta ctgatagaaa 2400
atctggaaat attcagaaag aatggctttg actttgtcat tgatgaggat gctccagtca 2460
ctgaaagggc taaattgatt tccttaccaa ctagtaaaaa ctggaccttt ggaccccaag 2520
atatagatga actgatcttt atgttaagtg acagccctgg ggtcatgtgc cggccctcac 2580
gagtcagaca gatgtttgct tccagagcct gtcggaagtc agtgatgatt ggaacggcgc 2640
tcaatgcgag cgagatgaag aagctcatca cccacatggg tgagatggac cacccctgga 2700
actgccccca cggcaggcca accatgaggc acgttgccaa tctggatgtc atctctcaga 2760
actgacacac cccttgtagc atagagttta ttacagattg ttcggtttgc aaagagaagg 2820
ttttaagtaa tctgattatc gttgtacaaa aattagcatg ctgctttaat gtactggatc 2880
catttaaaag cagtgttaag gcaggcatga tggagtgttc ctctagctca gctacttggg 2940
tgatccggtg ggagctcatg tgagcccagg actttgagac cactccgagc cacattcatg 3000
agactcaatt caaggacaaa aaaaaaaaga tatttttgaa gccttttaaa aaaaaa 3056

<210> SEQ ID NO 7
<211> LENGTH: 862
<212> TYPE: PRT
<213> ORGANISM: Homo sapiens

<400> SEQUENCE: 7

Met Glu Arg Ala Glu Ser Ser Ser Thr Glu Pro Ala Lys Ala Ile Lys
1 5 10 15

Pro Ile Asp Arg Lys Ser Val His Gln Ile Cys Ser Gly Gln Val Val
20 25 30

Leu Ser Leu Ser Thr Ala Val Lys Glu Leu Val Glu Asn Ser Leu Asp
35 40 45

Ala Gly Ala Thr Asn Ile Asp Leu Lys Leu Lys Asp Tyr Gly Val Asp
50 55 60

Leu Ile Glu Val Ser Asp Asn Gly Cys Gly Val Glu Glu Glu Asn Phe
65 70 75 80

Glu Gly Leu Thr Leu Lys His His Thr Ser Lys Ile Gln Glu Phe Ala
85 90 95

Asp Leu Thr Gln Val Glu Thr Phe Gly Phe Arg Gly Glu Ala Leu Ser
100 105 110

Ser Leu Cys Ala Leu Ser Asp Val Thr Ile Ser Thr Cys His Ala Ser
115 120 125

Ala Lys Val Gly Thr Arg Leu Met Phe Asp His Asn Gly Lys Ile Ile
130 135 140

-continued

```
Gln Lys Thr Pro Tyr Pro Arg Pro Arg Gly Thr Thr Val Ser Val Gln
145                 150                 155                 160

Gln Leu Phe Ser Thr Leu Pro Val Arg His Lys Glu Phe Gln Arg Asn
                165                 170                 175

Ile Lys Lys Glu Tyr Ala Lys Met Val Gln Val Leu His Ala Tyr Cys
            180                 185                 190

Ile Ile Ser Ala Gly Ile Arg Val Ser Cys Thr Asn Gln Leu Gly Gln
        195                 200                 205

Gly Lys Arg Gln Pro Val Val Cys Thr Gly Gly Ser Pro Ser Ile Lys
    210                 215                 220

Glu Asn Ile Gly Ser Val Phe Gly Gln Lys Gln Leu Gln Ser Leu Ile
225                 230                 235                 240

Pro Phe Val Gln Leu Pro Pro Ser Asp Ser Val Cys Glu Glu Tyr Gly
                245                 250                 255

Leu Ser Cys Ser Asp Ala Leu His Asn Leu Phe Tyr Ile Ser Gly Phe
            260                 265                 270

Ile Ser Gln Cys Thr His Gly Val Gly Arg Ser Ser Thr Asp Arg Gln
        275                 280                 285

Phe Phe Phe Ile Asn Arg Arg Pro Cys Asp Pro Ala Lys Val Cys Arg
    290                 295                 300

Leu Val Asn Glu Val Tyr His Met Tyr Asn Arg His Gln Tyr Pro Phe
305                 310                 315                 320

Val Val Leu Asn Ile Ser Val Asp Ser Glu Cys Val Asp Ile Asn Val
                325                 330                 335

Thr Pro Asp Lys Arg Gln Ile Leu Leu Gln Glu Glu Lys Leu Leu Leu
            340                 345                 350

Ala Val Leu Lys Thr Ser Leu Ile Gly Met Phe Asp Ser Asp Val Asn
        355                 360                 365

Lys Leu Asn Val Ser Gln Gln Pro Leu Leu Asp Val Glu Gly Asn Leu
    370                 375                 380

Ile Lys Met His Ala Ala Asp Leu Glu Lys Pro Met Val Glu Lys Gln
385                 390                 395                 400

Asp Gln Ser Pro Ser Leu Arg Thr Gly Glu Glu Lys Lys Asp Val Ser
                405                 410                 415

Ile Ser Arg Leu Arg Glu Ala Phe Ser Leu Arg His Thr Thr Glu Asn
            420                 425                 430

Lys Pro His Ser Pro Lys Thr Pro Glu Pro Arg Arg Ser Pro Leu Gly
        435                 440                 445

Gln Lys Arg Gly Met Leu Ser Ser Ser Thr Ser Gly Ala Ile Ser Asp
    450                 455                 460

Lys Gly Val Leu Arg Pro Gln Lys Glu Ala Val Ser Ser Ser His Gly
465                 470                 475                 480

Pro Ser Asp Pro Thr Asp Arg Ala Glu Val Glu Lys Asp Ser Gly His
                485                 490                 495

Gly Ser Thr Ser Val Asp Ser Glu Gly Phe Ser Ile Pro Asp Thr Gly
            500                 505                 510

Ser His Cys Ser Ser Glu Tyr Ala Ala Ser Ser Pro Gly Asp Arg Gly
        515                 520                 525

Ser Gln Glu His Val Asp Ser Gln Glu Lys Ala Pro Glu Thr Asp Asp
    530                 535                 540

Ser Phe Ser Asp Val Asp Cys His Ser Asn Gln Glu Asp Thr Gly Cys
545                 550                 555                 560

Lys Phe Arg Val Leu Pro Gln Pro Thr Asn Leu Ala Thr Pro Asn Thr
```

-continued

```
            565                 570                 575

Lys Arg Phe Lys Lys Glu Glu Ile Leu Ser Ser Ser Asp Ile Cys Gln
        580                 585                 590

Lys Leu Val Asn Thr Gln Asp Met Ser Ala Ser Gln Val Asp Val Ala
    595                 600                 605

Val Lys Ile Asn Lys Lys Val Val Pro Leu Asp Phe Ser Met Ser Ser
    610                 615                 620

Leu Ala Lys Arg Ile Lys Gln Leu His His Glu Ala Gln Gln Ser Glu
625                 630                 635                 640

Gly Glu Gln Asn Tyr Arg Lys Phe Arg Ala Lys Ile Cys Pro Gly Glu
                645                 650                 655

Asn Gln Ala Ala Glu Asp Glu Leu Arg Lys Glu Ile Ser Lys Thr Met
            660                 665                 670

Phe Ala Glu Met Glu Ile Ile Gly Gln Phe Asn Leu Gly Phe Ile Ile
        675                 680                 685

Thr Lys Leu Asn Glu Asp Ile Phe Ile Val Asp Gln His Ala Thr Asp
    690                 695                 700

Glu Lys Tyr Asn Phe Glu Met Leu Gln Gln His Thr Val Leu Gln Gly
705                 710                 715                 720

Gln Arg Leu Ile Ala Pro Gln Thr Leu Asn Leu Thr Ala Val Asn Glu
                725                 730                 735

Ala Val Leu Ile Glu Asn Leu Glu Ile Phe Arg Lys Asn Gly Phe Asp
            740                 745                 750

Phe Val Ile Asp Glu Asn Ala Pro Val Thr Glu Arg Ala Lys Leu Ile
        755                 760                 765

Ser Leu Pro Thr Ser Lys Asn Trp Thr Phe Gly Pro Gln Asp Val Asp
    770                 775                 780

Glu Leu Ile Phe Met Leu Ser Asp Ser Pro Gly Val Met Cys Arg Pro
785                 790                 795                 800

Ser Arg Val Lys Gln Met Phe Ala Ser Arg Ala Cys Arg Lys Ser Val
                805                 810                 815

Met Ile Gly Thr Ala Leu Asn Thr Ser Glu Met Lys Lys Leu Ile Thr
            820                 825                 830

His Met Gly Glu Met Asp His Pro Trp Asn Cys Pro His Gly Arg Pro
        835                 840                 845

Thr Met Arg His Ile Ala Asn Leu Gly Val Ile Ser Gln Asn
    850                 855                 860


<210> SEQ ID NO 8
<211> LENGTH: 2771
<212> TYPE: DNA
<213> ORGANISM: Homo sapiens

<400> SEQUENCE: 8

cgaggcggat cgggtgttgc atccatggag cgagctgaga gctcgagtac agaacctgct      60

aaggccatca aacctattga tcggaagtca gtccatcaga tttgctctgg gcaggtggta     120

ctgagtctaa gcactgcggt aaaggagtta gtagaaaaca gtctggatgc tggtgccact     180

aatattgatc taaagcttaa ggactatgga gtggatctta ttgaagtttc agacaatgga     240

tgtggggtag aagaagaaaa cttcgaaggc ttaactctga aacatcacac atctaagatt     300

caagagtttg ccgacctaac tcaggttgaa acttttggct ttcgggggga agctctgagc     360

tcactttgtg cactgagcga tgtcaccatt tctacctgcc acgcatcggc gaaggttgga     420

actcgactga tgtttgatca caatgggaaa attatccaga aaacccccta cccccgcccc     480
```

```
agagggacca cagtcagcgt gcagcagtta ttttccacac tacctgtgcg ccataaggaa    540
tttcaaagga atattaagaa ggagtatgcc aaaatggtcc aggtcttaca tgcatactgt    600
atcatttcag caggcatccg tgtaagttgc accaatcagc ttggacaagg aaaacgacag    660
cctgtggtat gcacaggtgg aagccccagc ataaaggaaa atatcggctc tgtgtttggg    720
cagaagcagt tgcaaagcct cattcctttt gttcagctgc cccctagtga ctccgtgtgt    780
gaagagtacg gtttgagctg ttcggatgct ctgcataatc tttttacat ctcaggtttc    840
atttcacaat gcacgcatgg agttggaagg agttcaacag acagacagtt tttctttatc    900
aaccggcggc cttgtgaccc agcaaaggtc tgcagactcg tgaatgaggt ctaccacatg    960
tataatcgac accagtatcc atttgttgtt cttaacattt ctgttgattc agaatgcgtt   1020
gatatcaatg ttactccaga taaaaggcaa attttgctac aagaggaaaa gcttttgttg   1080
gcagttttaa agacctcttt gataggaatg tttgatagtg atgtcaacaa gctaaatgtc   1140
agtcagcagc cactgctgga tgttgaaggt aacttaataa aaatgcatgc agcggatttg   1200
gaaaagccca tggtagaaaa gcaggatcaa tccccttcat taaggactgg agaagaaaaa   1260
aaagacgtgt ccatttccag actgcgagag gccttttctc ttcgtcacac aacagagaac   1320
aagcctcaca gcccaaagac tccagaacca agaaggagcc ctctaggaca gaaaaggggt   1380
atgctgtctt ctagcacttc aggtgccatc tctgacaaag gcgtcctgag acctcagaaa   1440
gaggcagtga gttccagtca cggacccagt gaccctacgg acagagcgga ggtggagaag   1500
gactcggggc acggcagcac ttccgtggat tctgaggggt tcagcatccc agacacgggc   1560
agtcactgca gcagcgagta tgcggccagc tccccagggg acaggggctc gcaggaacat   1620
gtggactctc aggagaaagc gcctgaaact gacgactctt tttcagatgt ggactgccat   1680
tcaaaccagg aagataccgg atgtaaattt cgagttttgc ctcagccaac taatctcgca   1740
accccaaaca caaagcgttt taaaaaagaa gaaattcttt ccagttctga catttgtcaa   1800
aagttagtaa atactcagga catgtcagcc tctcaggttg atgtagctgt gaaaattaat   1860
aagaaagttg tgcccctgga cttttctatg agttctttag ctaaacgaat aaagcagtta   1920
catcatgaag cacagcaaag tgaaggggaa cagaattaca ggaagtttag ggcaaagatt   1980
tgtcctggag aaaatcaagc agccgaagat gaactaagaa aagagataag taaaacgatg   2040
tttgcagaaa tggaaatcat tggtcagttt aacctgggat ttataataac caaactgaat   2100
gaggatatct tcatagtgga ccagcatgcc acggacgaga agtataactt cgagatgctg   2160
cagcagcaca ccgtgctcca ggggcagagg ctcatagcac ctcagactct caacttaact   2220
gctgttaatg aagctgttct gatagaaaat ctggaaatat ttagaaagaa tggctttgat   2280
tttgttatcg atgaaaatgc tccagtcact gaaagggcta aactgatttc cttgccaact   2340
agtaaaaact ggaccttcgg accccaggac gtcgatgaac tgatcttcat gctgagcgac   2400
agccctgggg tcatgtgccg gccttcccga gtcaagcaga tgtttgcctc cagagcctgc   2460
cggaagtcgg tgatgattgg gactgctctt aacacaagcg agatgaagaa actgatcacc   2520
cacatggggg agatggacca cccctggaac tgtccccatg gaaggccaac catgagacac   2580
atcgccaacc tgggtgtcat ttctcagaac tgaccgtagt cactgtatgg aataattggt   2640
tttatcgcag atttttatgt tttgaaagac agagtcttca ctaacctttt ttgttttaaa   2700
atgaaacctg ctacttaaaa aaaatacaca tcacacccat ttaaaagtga tcttgagaac   2760
cttttcaaac c                                                        2771
```

```
<210> SEQ ID NO 9
<211> LENGTH: 932
<212> TYPE: PRT
<213> ORGANISM: Homo sapiens

<400> SEQUENCE: 9

Met Lys Gln Leu Pro Ala Ala Thr Val Arg Leu Leu Ser Ser Ser Gln
1               5                   10                  15

Ile Ile Thr Ser Val Val Ser Val Val Lys Glu Leu Ile Glu Asn Ser
            20                  25                  30

Leu Asp Ala Gly Ala Thr Ser Val Asp Val Lys Leu Glu Asn Tyr Gly
        35                  40                  45

Phe Asp Lys Ile Glu Val Arg Asp Asn Gly Glu Gly Ile Lys Ala Val
    50                  55                  60

Asp Ala Pro Val Met Ala Met Lys Tyr Tyr Thr Ser Lys Ile Asn Ser
65                  70                  75                  80

His Glu Asp Leu Glu Asn Leu Thr Thr Tyr Gly Phe Arg Gly Glu Ala
                85                  90                  95

Leu Gly Ser Ile Cys Cys Ile Ala Glu Val Leu Ile Thr Thr Arg Thr
            100                 105                 110

Ala Ala Asp Asn Phe Ser Thr Gln Tyr Val Leu Asp Gly Ser Gly His
        115                 120                 125

Ile Leu Ser Gln Lys Pro Ser His Leu Gly Gln Gly Thr Thr Val Thr
    130                 135                 140

Ala Leu Arg Leu Phe Lys Asn Leu Pro Val Arg Lys Gln Phe Tyr Ser
145                 150                 155                 160

Thr Ala Lys Lys Cys Lys Asp Glu Ile Lys Lys Ile Gln Asp Leu Leu
                165                 170                 175

Met Ser Phe Gly Ile Leu Lys Pro Asp Leu Arg Ile Val Phe Val His
            180                 185                 190

Asn Lys Ala Val Ile Trp Gln Lys Ser Arg Val Ser Asp His Lys Met
        195                 200                 205

Ala Leu Met Ser Val Leu Gly Thr Ala Val Met Asn Asn Met Glu Ser
    210                 215                 220

Phe Gln Tyr His Ser Glu Glu Ser Gln Ile Tyr Leu Ser Gly Phe Leu
225                 230                 235                 240

Pro Lys Cys Asp Ala Asp His Ser Phe Thr Ser Leu Ser Thr Pro Glu
                245                 250                 255

Arg Ser Phe Ile Phe Ile Asn Ser Arg Pro Val His Gln Lys Asp Ile
            260                 265                 270

Leu Lys Leu Ile Arg His His Tyr Asn Leu Lys Cys Leu Lys Glu Ser
        275                 280                 285

Thr Arg Leu Tyr Pro Val Phe Phe Leu Lys Ile Asp Val Pro Thr Ala
    290                 295                 300

Asp Val Asp Val Asn Leu Thr Pro Asp Lys Ser Gln Val Leu Leu Gln
305                 310                 315                 320

Asn Lys Glu Ser Val Leu Ile Ala Leu Glu Asn Leu Met Thr Thr Cys
                325                 330                 335

Tyr Gly Pro Leu Pro Ser Thr Asn Ser Tyr Glu Asn Asn Lys Thr Asp
            340                 345                 350

Val Ser Ala Ala Asp Ile Val Leu Ser Lys Thr Ala Glu Thr Asp Val
        355                 360                 365

Leu Phe Asn Lys Val Glu Ser Ser Gly Lys Asn Tyr Ser Asn Val Asp
    370                 375                 380
```

-continued

```
Thr Ser Val Ile Pro Phe Gln Asn Asp Met His Asn Asp Glu Ser Gly
385                 390                 395                 400

Lys Asn Thr Asp Asp Cys Leu Asn His Gln Ile Ser Ile Gly Asp Phe
                405                 410                 415

Gly Tyr Gly His Cys Ser Ser Glu Ile Ser Asn Ile Asp Lys Asn Thr
            420                 425                 430

Lys Asn Ala Phe Gln Asp Ile Ser Met Ser Asn Val Ser Trp Glu Asn
        435                 440                 445

Ser Gln Thr Glu Tyr Ser Lys Thr Cys Phe Ile Ser Ser Val Lys His
    450                 455                 460

Thr Gln Ser Glu Asn Gly Asn Lys Asp His Ile Asp Glu Ser Gly Glu
465                 470                 475                 480

Asn Glu Glu Glu Ala Gly Leu Glu Asn Ser Ser Glu Ile Ser Ala Asp
                485                 490                 495

Glu Trp Ser Arg Gly Asn Ile Leu Lys Asn Ser Val Gly Glu Asn Ile
            500                 505                 510

Glu Pro Val Lys Ile Leu Val Pro Glu Lys Ser Leu Pro Cys Lys Val
        515                 520                 525

Ser Asn Asn Asn Tyr Pro Ile Pro Glu Gln Met Asn Leu Asn Glu Asp
    530                 535                 540

Ser Cys Asn Lys Lys Ser Asn Val Ile Asp Asn Lys Ser Gly Lys Val
545                 550                 555                 560

Thr Ala Tyr Asp Leu Leu Ser Asn Arg Val Ile Lys Lys Pro Met Ser
                565                 570                 575

Ala Ser Ala Leu Phe Val Gln Asp His Arg Pro Gln Phe Leu Ile Glu
            580                 585                 590

Asn Pro Lys Thr Ser Leu Glu Asp Ala Thr Leu Gln Ile Glu Glu Leu
        595                 600                 605

Trp Lys Thr Leu Ser Glu Glu Glu Lys Leu Lys Tyr Glu Glu Lys Ala
    610                 615                 620

Thr Lys Asp Leu Glu Arg Tyr Asn Ser Gln Met Lys Arg Ala Ile Glu
625                 630                 635                 640

Gln Glu Ser Gln Met Ser Leu Lys Asp Gly Arg Lys Lys Ile Lys Pro
                645                 650                 655

Thr Ser Ala Trp Asn Leu Ala Gln Lys His Lys Leu Lys Thr Ser Leu
            660                 665                 670

Ser Asn Gln Pro Lys Leu Asp Glu Leu Leu Gln Ser Gln Ile Glu Lys
        675                 680                 685

Arg Arg Ser Gln Asn Ile Lys Met Val Gln Ile Pro Phe Ser Met Lys
    690                 695                 700

Asn Leu Lys Ile Asn Phe Lys Lys Gln Asn Lys Val Asp Leu Glu Glu
705                 710                 715                 720

Lys Asp Glu Pro Cys Leu Ile His Asn Leu Arg Phe Pro Asp Ala Trp
                725                 730                 735

Leu Met Thr Ser Lys Thr Glu Val Met Leu Leu Asn Pro Tyr Arg Val
            740                 745                 750

Glu Glu Ala Leu Leu Phe Lys Arg Leu Leu Glu Asn His Lys Leu Pro
        755                 760                 765

Ala Glu Pro Leu Glu Lys Pro Ile Met Leu Thr Glu Ser Leu Phe Asn
    770                 775                 780

Gly Ser His Tyr Leu Asp Val Leu Tyr Lys Met Thr Ala Asp Asp Gln
785                 790                 795                 800
```

-continued

```
Arg Tyr Ser Gly Ser Thr Tyr Leu Ser Asp Pro Arg Leu Thr Ala Asn
            805                 810                 815

Gly Phe Lys Ile Lys Leu Ile Pro Gly Val Ser Ile Thr Glu Asn Tyr
            820                 825                 830

Leu Glu Ile Glu Gly Met Ala Asn Cys Leu Pro Phe Tyr Gly Val Ala
        835                 840                 845

Asp Leu Lys Glu Ile Leu Asn Ala Ile Leu Asn Arg Asn Ala Lys Glu
    850                 855                 860

Val Tyr Glu Cys Arg Pro Arg Lys Val Ile Ser Tyr Leu Glu Gly Glu
865                 870                 875                 880

Ala Val Arg Leu Ser Arg Gln Leu Pro Met Tyr Leu Ser Tyr Glu Asp
            885                 890                 895

Ile Gln Asp Ile Ile Tyr Arg Met Lys His Gln Phe Gly Asn Glu Ile
            900                 905                 910

Lys Glu Cys Val His Gly Arg Pro Phe Phe His His Leu Thr Tyr Leu
        915                 920                 925

Pro Glu Thr Thr
    930
```

<210> SEQ ID NO 10
<211> LENGTH: 3063
<212> TYPE: DNA
<213> ORGANISM: Homo sapiens

<400> SEQUENCE: 10

```
ggcacgagtg gctgcttgcg gctagtggat ggtaattgcc tgcctcgcgc tagcagcaag     60

ctgctctgtt aaaagcgaaa atgaaacaat tgcctgcggc aacagttcga ctcctttcaa    120

gttctcagat catcacttcg gtggtcagtg ttgtaaaaga gcttattgaa aactccttgg    180

atgctggtgc cacaagcgta gatgttaaac tggagaacta tggatttgat aaaattgagg    240

tgcgagataa cggggagggt atcaaggctg ttgatgcacc tgtaatggca atgaagtact    300

acacctcaaa aataaatagt catgaagatc ttgaaaattt gacaacttac ggttttcgtg    360

gagaagcctt ggggtcaatt tgttgtatag ctgaggtttt aattacaaca agaacggctg    420

ctgataattt tagcacccag tatgttttag atggcagtgg ccacatactt tctcagaaac    480

cttcacatct tggtcaaggt acaactgtaa ctgctttaag attatttaag aatctacctg    540

taagaaagca gttttactca actgcaaaaa aatgtaaaga tgaaataaaa aagatccaag    600

atctcctcat gagctttggt atccttaaac ctgacttaag gattgtcttt gtacataaca    660

aggcagttat ttggcagaaa agcagagtat cagatcacaa gatggctctc atgtcagttc    720

tggggactgc tgttatgaac aatatggaat cctttcagta ccactctgaa gaatctcaga    780

tttatctcag tggatttctt ccaaagtgtg atgcagacca ctctttcact agtctttcaa    840

caccagaaag aagtttcatc ttcataaaca gtcgaccagt acatcaaaaa gatatcttaa    900

agttaatccg acatcattac aatctgaaat gcctaaagga atctactcgt ttgtatcctg    960

ttttctttct gaaaatcgat gttcctacag ctgatgttga tgtaaattta acaccagata   1020

aaagccaagt attattacaa aataaggaat ctgttttaat tgctcttgaa aatctgatga   1080

cgacttgtta tggaccatta cctagtacaa attcttatga aaataataaa acagatgttt   1140

ccgcagctga catcgttctt agtaaaacag cagaaacaga tgtgcttttt aataaagtgg   1200

aatcatctgg aaagaattat tcaaatgttg atacttcagt cattccattc caaaatgata   1260

tgcataatga tgaatctgga aaaaacactg atgattgttt aaatcaccag ataagtattg   1320
```

-continued

```
gtgactttgg ttatggtcat tgtagtagtg aaatttctaa cattgataaa aacactaaga   1380

atgcatttca ggacatttca atgagtaatg tatcatggga gaactctcag acggaatata   1440

gtaaaacttg ttttataagt tccgttaagc acacccagtc agaaaatggc aataaagacc   1500

atatagatga gagtggggaa aatgaggaag aagcaggtct tgaaaactct tcggaaattt   1560

ctgcagatga gtggagcagg ggaaatatac ttaaaaattc agtgggagag aatattgaac   1620

ctgtgaaaat tttagtgcct gaaaaaagtt taccatgtaa agtaagtaat aataattatc   1680

caatccctga acaaatgaat cttaatgaag attcatgtaa caaaaaatca aatgtaatag   1740

ataataaatc tggaaaagtt acagcttatg atttacttag caatcgagta atcaagaaac   1800

ccatgtcagc aagtgctctt tttgttcaag atcatcgtcc tcagtttctc atagaaaatc   1860

ctaagactag tttagaggat gcaacactac aaattgaaga actgtggaag acattgagtg   1920

aagaggaaaa actgaaatat gaagagaagg ctactaaaga cttggaacga tacaatagtc   1980

aaatgaagag agccattgaa caggagtcac aaatgtcact aaaagatggc agaaaaaaga   2040

taaaacccac cagcgcatgg aatttggccc agaagcacaa gttaaaaacc tcattatcta   2100

atcaaccaaa acttgatgaa ctccttcagt cccaaattga aaaaagaagg agtcaaaata   2160

ttaaaatggt acagatcccc ttttctatga aaaacttaaa aataaatttt aagaaacaaa   2220

acaaagttga cttagaagag aaggatgaac cttgcttgat ccacaatctc aggtttcctg   2280

atgcatggct aatgacatcc aaaacagagg taatgttatt aaatccatat agagtagaag   2340

aagccctgct atttaaaaga cttcttgaga atcataaact tcctgcagag ccactggaaa   2400

agccaattat gttaacagag agtcttttta atggatctca ttatttagac gttttatata   2460

aaatgacagc agatgaccaa agatacagtg gatcaactta cctgtctgat cctcgtctta   2520

cagcgaatgg tttcaagata aaattgatac caggagtttc aattactgaa aattacttgg   2580

aaatagaagg aatggctaat tgtctcccat tctatggagt agcagattta aaagaaattc   2640

ttaatgctat attaaacaga aatgcaaagg aagtttatga atgtagacct cgcaaagtga   2700

taagttattt agagggagaa gcagtgcgtc tatccagaca attacccatg tacttatcaa   2760

aagaggacat ccaagacatt atctacagaa tgaagcacca gtttggaaat gaaattaaag   2820

agtgtgttca tggtcgccca tttttcatc atttaaccta tcttccagaa actacatgat   2880

taaatatgtt taagaagatt agttaccatt gaaattggtt ctgtcataaa acagcatgag   2940

tctggtttta aattatcttt gtattatgtg tcacatggtt attttttaaa tgaggattca   3000

ctgacttgtt tttatattga aaaaagttcc acgtattgta gaaaacgtaa ataaactaat   3060

aac                                                                 3063
```

<210> SEQ ID NO 11
<211> LENGTH: 934
<212> TYPE: PRT
<213> ORGANISM: Homo sapiens

<400> SEQUENCE: 11

```
Met Ala Val Gln Pro Lys Glu Thr Leu Gln Leu Glu Ser Ala Ala Glu
1               5                   10                  15

Val Gly Phe Val Arg Phe Phe Gln Gly Met Pro Glu Lys Pro Thr Thr
            20                  25                  30

Thr Val Arg Leu Phe Asp Arg Gly Asp Phe Tyr Thr Ala His Gly Glu
        35                  40                  45

Asp Ala Leu Leu Ala Ala Arg Glu Val Phe Lys Thr Gln Gly Val Ile
    50                  55                  60
```

-continued

```
Lys Tyr Met Gly Pro Ala Gly Ala Lys Asn Leu Gln Ser Val Val Leu
65                  70                  75                  80

Ser Lys Met Asn Phe Glu Ser Phe Val Lys Asp Leu Leu Leu Val Arg
                85                  90                  95

Gln Tyr Arg Val Glu Val Tyr Lys Asn Arg Ala Gly Asn Lys Ala Ser
            100                 105                 110

Lys Glu Asn Asp Trp Tyr Leu Ala Tyr Lys Ala Ser Pro Gly Asn Leu
        115                 120                 125

Ser Gln Phe Glu Asp Ile Leu Phe Gly Asn Asn Asp Met Ser Ala Ser
    130                 135                 140

Ile Gly Val Val Gly Val Lys Met Ser Ala Val Asp Gly Gln Arg Gln
145                 150                 155                 160

Val Gly Val Gly Tyr Val Asp Ser Ile Gln Arg Lys Leu Gly Leu Cys
                165                 170                 175

Glu Phe Pro Asp Asn Asp Gln Phe Ser Asn Leu Glu Ala Leu Leu Ile
            180                 185                 190

Gln Ile Gly Pro Lys Glu Cys Val Leu Pro Gly Gly Glu Thr Ala Gly
        195                 200                 205

Asp Met Gly Lys Leu Arg Gln Ile Ile Gln Arg Gly Gly Ile Leu Ile
    210                 215                 220

Thr Glu Arg Lys Lys Ala Asp Phe Ser Thr Lys Asp Ile Tyr Gln Asp
225                 230                 235                 240

Leu Asn Arg Leu Leu Lys Gly Lys Lys Gly Glu Gln Met Asn Ser Ala
                245                 250                 255

Val Leu Pro Glu Met Glu Asn Gln Val Ala Val Ser Ser Leu Ser Ala
            260                 265                 270

Val Ile Lys Phe Leu Glu Leu Leu Ser Asp Asp Ser Asn Phe Gly Gln
        275                 280                 285

Phe Glu Leu Thr Thr Phe Asp Phe Ser Gln Tyr Met Lys Leu Asp Ile
    290                 295                 300

Ala Ala Val Arg Ala Leu Asn Leu Phe Gln Gly Ser Val Glu Asp Thr
305                 310                 315                 320

Thr Gly Ser Gln Ser Leu Ala Ala Leu Leu Asn Lys Cys Lys Thr Pro
                325                 330                 335

Gln Gly Gln Arg Leu Val Asn Gln Trp Ile Lys Gln Pro Leu Met Asp
            340                 345                 350

Lys Asn Arg Ile Glu Glu Arg Leu Asn Leu Val Glu Ala Phe Val Glu
        355                 360                 365

Asp Ala Glu Leu Arg Gln Thr Leu Gln Glu Asp Leu Leu Arg Arg Phe
    370                 375                 380

Pro Asp Leu Asn Arg Leu Ala Lys Lys Phe Gln Arg Gln Ala Ala Asn
385                 390                 395                 400

Leu Gln Asp Cys Tyr Arg Leu Tyr Gln Gly Ile Asn Gln Leu Pro Asn
                405                 410                 415

Val Ile Gln Ala Leu Glu Lys His Glu Gly Lys His Gln Lys Leu Leu
            420                 425                 430

Leu Ala Val Phe Val Thr Pro Leu Thr Asp Leu Arg Ser Asp Phe Ser
        435                 440                 445

Lys Phe Gln Glu Met Ile Glu Thr Thr Leu Asp Met Asp Gln Val Glu
    450                 455                 460

Asn His Glu Phe Leu Val Lys Pro Ser Phe Asp Pro Asn Leu Ser Glu
465                 470                 475                 480
```

-continued

```
Leu Arg Glu Ile Met Asn Asp Leu Glu Lys Lys Met Gln Ser Thr Leu
                485                 490                 495

Ile Ser Ala Ala Arg Asp Leu Gly Leu Asp Pro Gly Lys Gln Ile Lys
            500                 505                 510

Leu Asp Ser Ser Ala Gln Phe Gly Tyr Tyr Phe Arg Val Thr Cys Lys
        515                 520                 525

Glu Glu Lys Val Leu Arg Asn Asn Lys Asn Phe Ser Thr Val Asp Ile
    530                 535                 540

Gln Lys Asn Gly Val Lys Phe Thr Asn Ser Lys Leu Thr Ser Leu Asn
545                 550                 555                 560

Glu Glu Tyr Thr Lys Asn Lys Thr Glu Tyr Glu Glu Ala Gln Asp Ala
                565                 570                 575

Ile Val Lys Glu Ile Val Asn Ile Ser Ser Gly Tyr Val Glu Pro Met
            580                 585                 590

Gln Thr Leu Asn Asp Val Leu Ala Gln Leu Asp Ala Val Val Ser Phe
        595                 600                 605

Ala His Val Ser Asn Gly Ala Pro Val Pro Tyr Val Arg Pro Ala Ile
    610                 615                 620

Leu Glu Lys Gly Gln Gly Arg Ile Ile Leu Lys Ala Ser Arg His Ala
625                 630                 635                 640

Cys Val Glu Val Gln Asp Glu Ile Ala Phe Ile Pro Asn Asp Val Tyr
                645                 650                 655

Phe Glu Lys Asp Lys Gln Met Phe His Ile Ile Thr Gly Pro Asn Met
            660                 665                 670

Gly Gly Lys Ser Thr Tyr Ile Arg Gln Thr Gly Val Ile Val Leu Met
        675                 680                 685

Ala Gln Ile Gly Cys Phe Val Pro Cys Glu Ser Ala Glu Val Ser Ile
    690                 695                 700

Val Asp Cys Ile Leu Ala Arg Val Gly Ala Gly Asp Ser Gln Leu Lys
705                 710                 715                 720

Gly Val Ser Thr Phe Met Ala Glu Met Leu Glu Thr Ala Ser Ile Leu
                725                 730                 735

Arg Ser Ala Thr Lys Asp Ser Leu Ile Ile Ile Asp Glu Leu Gly Arg
            740                 745                 750

Gly Thr Ser Thr Tyr Asp Gly Phe Gly Leu Ala Trp Ala Ile Ser Glu
        755                 760                 765

Tyr Ile Ala Thr Lys Ile Gly Ala Phe Cys Met Phe Ala Thr His Phe
    770                 775                 780

His Glu Leu Thr Ala Leu Ala Asn Gln Ile Pro Thr Val Asn Asn Leu
785                 790                 795                 800

His Val Thr Ala Leu Thr Thr Glu Glu Thr Leu Thr Met Leu Tyr Gln
                805                 810                 815

Val Lys Lys Gly Val Cys Asp Gln Ser Phe Gly Ile His Val Ala Glu
            820                 825                 830

Leu Ala Asn Phe Pro Lys His Val Ile Glu Cys Ala Lys Gln Lys Ala
        835                 840                 845

Leu Glu Leu Glu Glu Phe Gln Tyr Ile Gly Glu Ser Gln Gly Tyr Asp
    850                 855                 860

Ile Met Glu Pro Ala Ala Lys Lys Cys Tyr Leu Glu Arg Glu Gln Gly
865                 870                 875                 880

Glu Lys Ile Ile Gln Glu Phe Leu Ser Lys Val Lys Gln Met Pro Phe
                885                 890                 895

Thr Glu Met Ser Glu Glu Asn Ile Thr Ile Lys Leu Lys Gln Leu Lys
```

-continued

```
          900                 905                 910

Ala Glu Val Ile Ala Lys Asn Asn Ser Phe Val Asn Glu Ile Ile Ser
        915                 920                 925

Arg Ile Lys Val Thr Thr
    930


<210> SEQ ID NO 12
<211> LENGTH: 3145
<212> TYPE: DNA
<213> ORGANISM: Homo sapiens

<400> SEQUENCE: 12

ggcgggaaac agcttagtgg gtgtggggtc gcgcattttc ttcaaccagg aggtgaggag     60

gtttcgacat ggcggtgcag ccgaaggaga cgctgcagtt ggagagcgcg gccgaggtcg    120

gcttcgtgcg cttctttcag ggcatgccgg agaagccgac caccacagtg cgccttttcg    180

accggggcga cttctatacg gcgcacggcg aggacgcgct gctggccgcc cgggaggtgt    240

tcaagaccca gggggtgatc aagtacatgg ggccggcagg agcaaagaat ctgcagagtg    300

ttgtgcttag taaaatgaat tttgaatctt ttgtaaaaga tcttcttctg gttcgtcagt    360

atagagttga agtttataag aatagagctg gaaataaggc atccaaggag aatgattggt    420

atttggcata taaggcttct cctggcaatc tctctcagtt tgaagacatt ctctttggta    480

acaatgatat gtcagcttcc attggtgttg tgggtgttaa aatgtccgca gttgatggcc    540

agagacaggt tggagttggg tatgtggatt ccatacagag gaaactagga ctgtgtgaat    600

tccctgataa tgatcagttc tccaatcttg aggctctcct catccagatt ggaccaaagg    660

aatgtgtttt acccggagga gagactgctg gagacatggg gaaactgaga cagataattc    720

aaagaggagg aattctgatc acagaaagaa aaaaagctga cttttccaca aaagacattt    780

atcaggacct caaccggttg ttgaaaggca aaaagggaga gcagatgaat agtgctgtat    840

tgccagaaat ggagaatcag gttgcagttt catcactgtc tgcggtaatc aagtttttag    900

aactcttatc agatgattcc aactttggac agtttgaact gactactttt gacttcagcc    960

agtatatgaa attggatatt gcagcagtca gagcccttaa cctttttcag ggttctgttg   1020

aagataccac tggctctcag tctctggctg ccttgctgaa taagtgtaaa acccctcaag   1080

gacaaagact tgttaaccag tggattaagc agcctctcat ggataagaac agaatagagg   1140

agagattgaa tttagtggaa gcttttgtag aagatgcaga attgaggcag actttacaag   1200

aagatttact tcgtcgattc ccagatctta accgacttgc caagaagttt caaagacaag   1260

cagcaaactt acaagattgt taccgactct atcagggtat aaatcaacta cctaatgtta   1320

tacaggctct ggaaaaacat gaaggaaaac accagaaatt attgttggca gtttttgtga   1380

ctcctcttac tgatcttcgt tctgacttct ccaagtttca ggaaatgata gaaacaactt   1440

tagatatgga tcaggtggaa aaccatgaat tccttgtaaa accttcattt gatcctaatc   1500

tcagtgaatt aagagaaata atgaatgact tggaaaagaa gatgcagtca acattaataa   1560

gtgcagccag agatcttggc ttggaccctg gcaaacagat taaactggat tccagtgcac   1620

agtttggata ttactttcgt gtaacctgta aggaagaaaa agtccttcgt aacaataaaa   1680

actttagtac tgtagatatc cagaagaatg gtgttaaatt taccaacagc aaattgactt   1740

ctttaaatga agagtatacc aaaaataaaa cagaatatga agaagcccag gatgccattg   1800

ttaaagaaat tgtcaatatt tcttcaggct atgtagaacc aatgcagaca ctcaatgatg   1860

tgttagctca gctagatgct gttgtcagct ttgctcacgt gtcaaatgga gcacctgttc   1920
```

```
catatgtacg accagccatt ttggagaaag gacaaggaag aattatatta aaagcatcca   1980

ggcatgcttg tgttgaagtt caagatgaaa ttgcatttat tcctaatgac gtatactttg   2040

aaaaagataa acagatgttc cacatcatta ctggccccaa tatgggaggt aaatcaacat   2100

atattcgaca aactggggtg atagtactca tggcccaaat tgggtgtttt gtgccatgtg   2160

agtcagcaga agtgtccatt gtggactgca tcttagcccg agtaggggct ggtgacagtc   2220

aattgaaagg agtctccacg ttcatggctg aaatgttgga aactgcttct atcctcaggt   2280

ctgcaaccaa agattcatta ataatcatag atgaattggg aagaggaact tctacctacg   2340

atggatttgg gttagcatgg gctatatcag aatacattgc aacaaagatt ggtgcttttt   2400

gcatgtttgc aacccatttt catgaactta ctgccttggc caatcagata ccaactgtta   2460

ataatctaca tgtcacagca ctcaccactg aagagacctt aactatgctt tatcaggtga   2520

agaaaggtgt ctgtgatcaa agttttggga ttcatgttgc agagcttgct aatttcccta   2580

agcatgtaat agagtgtgct aaacagaaag ccctggaact tgaggagttt cagtatattg   2640

gagaatcgca aggatatgat atcatggaac cagcagcaaa gaagtgctat ctggaaagag   2700

agcaaggtga aaaaattatt caggagttcc tgtccaaggt gaaacaaatg ccctttactg   2760

aaatgtcaga agaaaacatc acaataaagt taaaacagct aaaagctgaa gtaatagcaa   2820

agaataatag ctttgtaaat gaaatcattt cacgaataaa agttactacg tgaaaaatcc   2880

cagtaatgga atgaaggtaa tattgataag ctattgtctg taatagtttt atattgtttt   2940

atattaaccc tttttccata gtgttaactg tcagtgccca tgggctatca acttaataag   3000

atatttagta atattttact ttgaggacat tttcaaagat ttttattttg aaaaatgaga   3060

gctgtaactg aggactgttt gcaattgaca taggcaataa taagtgatgt gctgaatttt   3120

ataaataaaa tcatgtagtt tgtgg                                         3145
```

<210> SEQ ID NO 13
<211> LENGTH: 756
<212> TYPE: PRT
<213> ORGANISM: Homo sapiens

<400> SEQUENCE: 13

```
Met Ser Phe Val Ala Gly Val Ile Arg Arg Leu Asp Glu Thr Val Val
1               5                   10                  15

Asn Arg Ile Ala Ala Gly Glu Val Ile Gln Arg Pro Ala Asn Ala Ile
            20                  25                  30

Lys Glu Met Ile Glu Asn Cys Leu Asp Ala Lys Ser Thr Ser Ile Gln
        35                  40                  45

Val Ile Val Lys Glu Gly Gly Leu Lys Leu Ile Gln Ile Gln Asp Asn
    50                  55                  60

Gly Thr Gly Ile Arg Lys Glu Asp Leu Asp Ile Val Cys Glu Arg Phe
65                  70                  75                  80

Thr Thr Ser Lys Leu Gln Ser Phe Glu Asp Leu Ala Ser Ile Ser Thr
                85                  90                  95

Tyr Gly Phe Arg Gly Glu Ala Leu Ala Ser Ile Ser His Val Ala His
            100                 105                 110

Val Thr Ile Thr Thr Lys Thr Ala Asp Gly Lys Cys Ala Tyr Arg Ala
        115                 120                 125

Ser Tyr Ser Asp Gly Lys Leu Lys Ala Pro Pro Lys Pro Cys Ala Gly
    130                 135                 140

Asn Gln Gly Thr Gln Ile Thr Val Glu Asp Leu Phe Tyr Asn Ile Ala
```

-continued

```
145                 150                 155                 160

Thr Arg Arg Lys Ala Leu Lys Asn Pro Ser Glu Glu Tyr Gly Lys Ile
                165                 170                 175

Leu Glu Val Val Gly Arg Tyr Ser Val His Asn Ala Gly Ile Ser Phe
            180                 185                 190

Ser Val Lys Lys Gln Gly Glu Thr Val Ala Asp Val Arg Thr Leu Pro
        195                 200                 205

Asn Ala Ser Thr Val Asp Asn Ile Arg Ser Ile Phe Gly Asn Ala Val
    210                 215                 220

Ser Arg Glu Leu Ile Glu Ile Gly Cys Glu Asp Lys Thr Leu Ala Phe
225                 230                 235                 240

Lys Met Asn Gly Tyr Ile Ser Asn Ala Asn Tyr Ser Val Lys Lys Cys
                245                 250                 255

Ile Phe Leu Leu Phe Ile Asn His Arg Leu Val Glu Ser Thr Ser Leu
            260                 265                 270

Arg Lys Ala Ile Glu Thr Val Tyr Ala Ala Tyr Leu Pro Lys Asn Thr
        275                 280                 285

His Pro Phe Leu Tyr Leu Ser Leu Glu Ile Ser Pro Gln Asn Val Asp
    290                 295                 300

Val Asp Val His Pro Thr Lys His Glu Val His Phe Leu His Glu Glu
305                 310                 315                 320

Ser Ile Leu Glu Arg Val Gln Gln His Ile Glu Ser Lys Leu Leu Gly
                325                 330                 335

Ser Asn Ser Ser Arg Met Tyr Phe Thr Gln Thr Leu Leu Pro Gly Leu
            340                 345                 350

Ala Gly Pro Ser Gly Glu Met Val Lys Ser Thr Thr Ser Leu Thr Ser
        355                 360                 365

Ser Ser Thr Ser Gly Ser Ser Asp Lys Val Tyr Ala His Gln Met Val
    370                 375                 380

Arg Thr Asp Ser Arg Glu Gln Leu Lys Asp Ala Phe Leu Gln Pro Leu
385                 390                 395                 400

Ser Lys Pro Leu Ser Ser Gln Pro Gln Ala Ile Val Thr Glu Asp Lys
                405                 410                 415

Thr Asp Ile Ser Ser Gly Arg Ala Arg Gln Gln Asp Glu Glu Met Leu
            420                 425                 430

Glu Leu Pro Ala Pro Ala Glu Val Ala Ala Lys Asn Gln Ser Leu Glu
        435                 440                 445

Gly Asp Thr Thr Lys Gly Thr Ser Glu Met Ser Glu Lys Arg Gly Pro
    450                 455                 460

Thr Ser Ser Asn Pro Arg Lys Arg His Arg Glu Asp Ser Asp Val Glu
465                 470                 475                 480

Met Val Glu Asp Asp Ser Arg Lys Glu Met Thr Ala Ala Cys Thr Pro
                485                 490                 495

Arg Arg Arg Ile Ile Asn Leu Thr Ser Val Leu Ser Leu Gln Glu Glu
            500                 505                 510

Ile Asn Glu Gln Gly His Glu Val Leu Arg Glu Met Leu His Asn His
        515                 520                 525

Ser Phe Val Gly Cys Val Asn Pro Gln Trp Ala Leu Ala Gln His Gln
    530                 535                 540

Thr Lys Leu Tyr Leu Leu Asn Thr Thr Lys Leu Ser Glu Glu Leu Phe
545                 550                 555                 560

Tyr Gln Ile Leu Ile Tyr Asp Phe Ala Asn Phe Gly Val Leu Arg Leu
                565                 570                 575
```

-continued

```
Ser Glu Pro Ala Pro Leu Phe Asp Leu Ala Met Leu Ala Leu Asp Ser
            580                 585                 590

Pro Glu Ser Gly Trp Thr Glu Glu Asp Gly Pro Lys Glu Gly Leu Ala
        595                 600                 605

Glu Tyr Ile Val Glu Phe Leu Lys Lys Lys Ala Glu Met Leu Ala Asp
    610                 615                 620

Tyr Phe Ser Leu Glu Ile Asp Glu Glu Gly Asn Leu Ile Gly Leu Pro
625                 630                 635                 640

Leu Leu Ile Asp Asn Tyr Val Pro Pro Leu Glu Gly Leu Pro Ile Phe
                645                 650                 655

Ile Leu Arg Leu Ala Thr Glu Val Asn Trp Asp Glu Glu Lys Glu Cys
            660                 665                 670

Phe Glu Ser Leu Ser Lys Glu Cys Ala Met Phe Tyr Ser Ile Arg Lys
        675                 680                 685

Gln Tyr Ile Ser Glu Glu Ser Thr Leu Ser Gly Gln Gln Ser Glu Val
    690                 695                 700

Pro Gly Ser Ile Pro Asn Ser Trp Lys Trp Thr Val Glu His Ile Val
705                 710                 715                 720

Tyr Lys Ala Leu Arg Ser His Ile Leu Pro Pro Lys His Phe Thr Glu
                725                 730                 735

Asp Gly Asn Ile Leu Gln Leu Ala Asn Leu Pro Asp Leu Tyr Lys Val
            740                 745                 750

Phe Glu Arg Cys
        755
```

<210> SEQ ID NO 14
<211> LENGTH: 2484
<212> TYPE: DNA
<213> ORGANISM: Homo sapiens

<400> SEQUENCE: 14

```
cttggctctt ctggcgccaa aatgtcgttc gtggcagggg ttattcggcg gctggacgag      60

acagtggtga accgcatcgc ggcgggggaa gttatccagc ggccagctaa tgctatcaaa     120

gagatgattg agaactgttt agatgcaaaa tccacaagta ttcaagtgat tgttaaagag     180

ggaggcctga agttgattca gatccaagac aatggcaccg ggatcaggaa agaagatctg     240

gatattgtat gtgaaaggtt cactactagt aaactgcagt cctttgagga tttagccagt     300

atttctacct atggctttcg aggtgaggct ttggccagca taagccatgt ggctcatgtt     360

actattacaa cgaaaacagc tgatggaaag tgtgcataca gagcaagtta ctcagatgga     420

aaactgaaag cccctcctaa accatgtgct ggcaatcaag ggacccagat cacggtggag     480

gaccttttt acaacatagc cacgaggaga aaagctttaa aaaatccaag tgaagaatat      540

gggaaaattt tggaagttgt tggcaggtat tcagtacaca atgcaggcat tagtttctca     600

gttaaaaaac aaggagagac agtagctgat gttaggacac tacccaatgc ctcaaccgtg     660

gacaatattc gctccatctt tggaaatgct gttagtcgag aactgataga aattggatgt     720

gaggataaaa ccctagcctt caaaatgaat ggttacatat ccaatgcaaa ctactcagtg     780

aagaagtgca tcttcttact cttcatcaac catcgtctgg tagaatcaac ttccttgaga     840

aaagccatag aaacagtgta tgcagcctat ttgcccaaaa acacacaccc attcctgtac     900

ctcagtttag aaatcagtcc ccagaatgtg gatgttaatg tgcaccccac aaagcatgaa     960

gttcacttcc tgcacgagga gagcatcctg gagcgggtgc agcagcacat cgagagcaag    1020
```

-continued

```
ctcctgggct ccaattcctc caggatgtac ttcacccaga ctttgctacc aggacttgct   1080

ggcccctctg gggagatggt taaatccaca acaagtctga cctcgtcttc tacttctgga   1140

agtagtgata aggtctatgc ccaccagatg gttcgtacag attcccggga acagaagctt   1200

gatgcatttc tgcagcctct gagcaaaccc ctgtccagtc agccccaggc cattgtcaca   1260

gaggataaga cagatatttc tagtggcagg gctaggcagc aagatgagga gatgcttgaa   1320

ctcccagccc ctgctgaagt ggctgccaaa aatcagagct tggagggggga tacaacaaag  1380

gggacttcag aaatgtcaga gaagagagga cctacttcca gcaaccccag aaagagacat   1440

cgggaagatt ctgatgtgga aatggtggaa gatgattccc gaaaggaaat gactgcagct   1500

tgtacccccc ggagaaggat cattaacctc actagtgttt tgagtctcca ggaagaaatt   1560

aatgagcagg gacatgaggt tctccgggag atgttgcata accactcctt cgtgggctgt   1620

gtgaatcctc agtgggcctt ggcacagcat caaaccaagt tataccttct caacaccacc   1680

aagcttagtg aagaactgtt ctaccagata ctcatttatg attttgccaa ttttggtgtt   1740

ctcaggttat cggagccagc accgctcttt gaccttgcca tgcttgcctt agatagtcca   1800

gagagtggct ggacagagga agatggtccc aaagaaggac ttgctgaata cattgttgag   1860

tttctgaaga agaaggctga gatgcttgca gactatttct ctttggaaat tgatgaggaa   1920

gggaacctga ttggattacc ccttctgatt gacaactatg tgcccccttt ggagggactg   1980

cctatcttca ttcttcgact agccactgag gtgaattggg acgaagaaaa ggaatgtttt   2040

gaaagcctca gtaaagaatg cgctatgttc tattccatcc ggaagcagta catatctgag   2100

gagtcgaccc tctcaggcca gcagagtgaa gtgcctggct ccattccaaa ctcctggaag   2160

tggactgtgg aacacattgt ctataaagcc ttgcgctcac acattctgcc tcctaaacat   2220

ttcacagaag atggaaatat cctgcagctt gctaacctgc ctgatctata caaagtcttt   2280

gagaggtgtt aaatatggtt atttatgcac tgtgggatgt gttcttcttt ctctgtattc   2340

cgatacaaag tgttgtatca aagtgtgata tacaaagtgt accaacataa gtgttggtag   2400

cacttaagac ttatacttgc cttctgatag tattccttta tacacagtgg attgattata   2460

aataaataga tgtgtcttaa cata                                          2484
```

```
<210> SEQ ID NO 15
<211> LENGTH: 133
<212> TYPE: PRT
<213> ORGANISM: Homo sapiens

<400> SEQUENCE: 15

Met Glu Arg Ala Glu Ser Ser Ser Thr Glu Pro Ala Lys Ala Ile Lys
1               5                   10                  15

Pro Ile Asp Arg Lys Ser Val His Gln Ile Cys Ser Gly Gln Val Val
            20                  25                  30

Leu Ser Leu Ser Thr Ala Val Lys Glu Leu Val Glu Asn Ser Leu Asp
        35                  40                  45

Ala Gly Ala Thr Asn Ile Asp Leu Lys Leu Lys Asp Tyr Gly Val Asp
    50                  55                  60

Leu Ile Glu Val Ser Asp Asn Gly Cys Gly Val Glu Glu Glu Asn Phe
65                  70                  75                  80

Glu Gly Leu Thr Leu Lys His His Thr Ser Lys Ile Gln Glu Phe Ala
                85                  90                  95

Asp Leu Thr Gln Val Glu Thr Phe Gly Phe Arg Gly Glu Ala Leu Ser
            100                 105                 110
```

-continued

```
Ser Leu Cys Ala Leu Ser Asp Val Thr Ile Ser Thr Cys His Ala Ser
        115                 120                 125

Ala Lys Val Gly Thr
    130
```

<210> SEQ ID NO 16
<211> LENGTH: 426
<212> TYPE: DNA
<213> ORGANISM: Homo sapiens

<400> SEQUENCE: 16

```
cgaggcggat cgggtgttgc atccatggag cgagctgaga gctcgagtac agaacctgct      60

aaggccatca aacctattga tcggaagtca gtccatcaga tttgctctgg gcaggtggta     120

ctgagtctaa gcactgcggt aaaggagtta gtagaaaaca gtctggatgc tggtgccact     180

aatattgatc taaagcttaa ggactatgga gtggatctta ttgaagtttc agacaatgga     240

tgtggggtag aagaagaaaa cttcgaaggc ttaactctga aacatcacac atctaagatt     300

caagagtttg ccgacctaac tcaggttgaa acttttggct ttcgggggga agctctgagc     360

tcactttgtg cactgagcga tgtcaccatt tctacctgcc acgcatcggc gaaggttgga     420

acttga                                                                426
```

<210> SEQ ID NO 17
<211> LENGTH: 19
<212> TYPE: DNA
<213> ORGANISM: Artificial Sequence
<220> FEATURE:
<223> OTHER INFORMATION: Oligonucleotide primer

<400> SEQUENCE: 17

```
tttcgcaacg ggtttgccg                                                   19
```

<210> SEQ ID NO 18
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 18

```
gtttcagagt taagccttcg                                                  20
```

<210> SEQ ID NO 19
<211> LENGTH: 13
<212> TYPE: DNA
<213> ORGANISM: Human immunoglobulin E light chain
<220> FEATURE:
<221> NAME/KEY: misc_feature
<222> LOCATION: (6)..(6)
<223> OTHER INFORMATION: n is a, c, g, or t

<400> SEQUENCE: 19

```
tacgtngaat aat                                                         13
```

<210> SEQ ID NO 20
<211> LENGTH: 13
<212> TYPE: DNA
<213> ORGANISM: Human immunoglobulin E light chain

<400> SEQUENCE: 20

```
tacgttgaat aat                                                         13
```

-continued

```
<210> SEQ ID NO 21
<211> LENGTH: 63
<212> TYPE: DNA
<213> ORGANISM: Human immunoglobulin E light chain

<400> SEQUENCE: 21

aacgtgacca tggtcgtctt cagtccgcga agggagtttg ggaactaagt atcctgtagg     60

ttg                                                                   63


<210> SEQ ID NO 22
<211> LENGTH: 63
<212> TYPE: DNA
<213> ORGANISM: Human immunoglobulin E light chain

<400> SEQUENCE: 22

aacgtgacca tggtcgtctt cagtccgcga aggggggtttg ggaactaagt atcctgtagg     60

ttg                                                                   63


<210> SEQ ID NO 23
<211> LENGTH: 63
<212> TYPE: DNA
<213> ORGANISM: Human immunoglobulin E light chain

<400> SEQUENCE: 23

aacgtgacca tggtcgtctt cagtccgcga agggrgtttg ggaactaagt atcctgtagg     60

ttg                                                                   63
```